United States Patent
Gray et al.

(10) Patent No.: US 11,814,379 B2
(45) Date of Patent: Nov. 14, 2023

(54) CYANO QUINOLINE AMIDE COMPOUNDS AS HER2 INHIBITORS AND METHODS OF USE

(71) Applicant: DANA-FARBER CANCER INSTITUTE, INC., Boston, MA (US)

(72) Inventors: Nathanael S. Gray, Boston, MA (US); Jaebong Jang, Boston, MA (US); Pasi Janne, Needham, MA (US); Jieun Son, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 85 days.

(21) Appl. No.: 16/973,276

(22) PCT Filed: Jun. 14, 2019

(86) PCT No.: PCT/US2019/037327
§ 371 (c)(1),
(2) Date: Dec. 8, 2020

(87) PCT Pub. No.: WO2019/241715
PCT Pub. Date: Dec. 19, 2019

(65) Prior Publication Data
US 2021/0355119 A1    Nov. 18, 2021

Related U.S. Application Data

(60) Provisional application No. 62/684,949, filed on Jun. 14, 2018.

(51) Int. Cl.
| | |
|---|---|
| C07D 215/54 | (2006.01) |
| C07D 401/12 | (2006.01) |
| C07D 471/04 | (2006.01) |
| C07D 487/04 | (2006.01) |
| A61P 35/00 | (2006.01) |
| C07D 417/12 | (2006.01) |

(52) U.S. Cl.
CPC ............ C07D 471/04 (2013.01); A61P 35/00 (2018.01); C07D 215/54 (2013.01); C07D 401/12 (2013.01); C07D 417/12 (2013.01); C07D 487/04 (2013.01)

(58) Field of Classification Search
CPC .. C07D 215/54; C07D 401/12; C07D 471/04; C07D 487/04
See application file for complete search history.

(56) References Cited

U.S. PATENT DOCUMENTS

| | | | |
|---|---|---|---|
| 2010/0240649 A1 | 9/2010 | Zhang | |
| 2015/0126537 A1 | 5/2015 | Zhang | |
| 2020/0190091 A1* | 6/2020 | Xia | ........................ C07C 257/12 |

FOREIGN PATENT DOCUMENTS

| | | |
|---|---|---|
| EP | 3677583 A1 | 7/2020 |
| WO | 2013053206 A1 | 4/2013 |
| WO | 2013173254 A1 | 11/2013 |
| WO | 2014177038 A1 | 11/2014 |

OTHER PUBLICATIONS

Tsou H-R et al, Optimization of 6,7-Disubstituted-4-(arylamino)quinoline-3-carbonitriles as Orally Active, Irreversible Inhibitors of HEGFR-2 Kinase Activitiy, Journal of Medicinal Chemistry, American Chemical Society, US, vol. 48, Jan. 27, 2005, pp. 1107-1131.
Caterina Carmi et al., Clinical Perspectives of Irreversible Tyrosine Kinase Inhibitors in Cancer, Biochemical Pharmacology, vol. 84, No. 11, Dec. 1, 2012, pp. 1388-1399.
Tsou H-R et al, 6-Substititued-4-(3-Bromphenylamino)Quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity, Journal of Medicinal Chemistry, American Chemical Society, US, vol. 44, No. 17, Jan. 1, 2001, pp. 2719-2734.
PCT Application No. PCT/US2019/037327, International Search Report and Written Opinion, dated Sep. 30, 2019, 10 pages.

* cited by examiner

*Primary Examiner* — Brian E McDowell
(74) *Attorney, Agent, or Firm* — Lathrop GPM LLP; Brian C. Trinque; Nicole Sassu

(57) ABSTRACT

The application relates to a compound having Formula I:

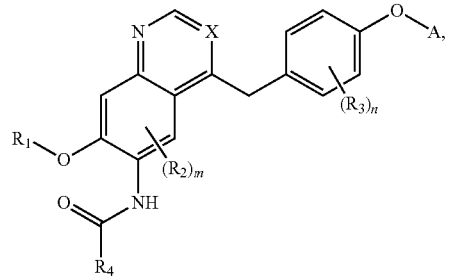

which modulates the activity of HER2 and/or a mutant thereof, a pharmaceutical composition comprising the compound, and a method of treating or preventing a disease in which HER2 and/or a mutant thereof plays a role.

19 Claims, 6 Drawing Sheets

CYANO QUINOLINE AMIDE COMPOUNDS AS HER2 INHIBITORS AND METHODS OF USE

RELATED APPLICATIONS

This application is a 35 U.S.C. § 371 filing of International Patent Application No. PCT/US2019/037327, filed Jun. 14, 2019, which claims priority to U.S. Provisional Application No. 62/684,949, filed on Jun. 14, 2018, the contents of which are hereby incorporated by reference in their entireties.

BACKGROUND

Human epidermal growth factor receptor 2 (HER2) is a member of the human epidermal growth factor receptor family. Aberrant HER2 expression or activity is one of the major causes of many cancers such as breast cancer, lung cancer, gastrointestinal cancer, and ovarian cancer. The most common malignancy and second leading cause of cancer-related death in women is breast cancer. Amplification of the HER2 gene, overexpression of the HER2 protein, or both occur in approximately 15-25% of breast cancers, which are classified as HER2-positive. In addition, HER2 mutations, which mainly consist of exon 20 insertion mutations, have been reported in approximately 1-4% of NSCLC patients. Phase I and II clinical data demonstrated that patients harboring HER2 mutations partially responded to treatment with afatinib, neratinib, or dacomitinib. Although patients with HER2 insYVMA have reported durable responses to afatinib as a single agent, a recent phase II trial of dacomitinib showed no response in all 13 patients with HER2 insYVMA (A775_G776insYVMA), which represents up to 80% of HER2 mutations in lung cancers.

Thus, novel inhibitors of HER2 are desired. Further, compounds possessing activity against HER2 mutations are needed, as they may have extended utility in treating tumors harboring such mutations.

SUMMARY

The present application features a class of novel small molecule compounds that inhibit human epidermal growth factor receptor 2 (HER2). In some embodiments, the compounds are capable of modulating (e.g., inhibiting or decreasing the activity of) HER2 that is resistant to other drugs, e.g., HER2 with one or more mutations.

In one aspect, the present application relates to a compound of Formula I:

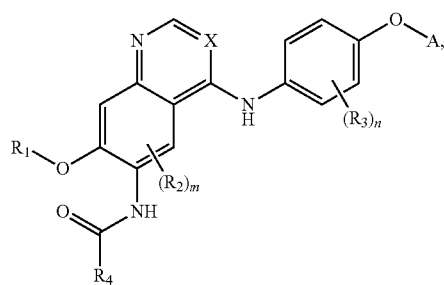

(I)

or a pharmaceutically acceptable salt or solvate thereof, wherein A, X, $R_1$, m, $R_2$, n, $R_3$, and $R_4$ are each described herein in detail below.

In another aspect, the present application relates to a pharmaceutical composition comprising a compound of Formula I, or a pharmaceutically acceptable salt or solvate thereof, and a pharmaceutically acceptable carrier.

In another aspect, the present application relates to a kit comprising a compound of the present application, or a pharmaceutically acceptable salt or solvate thereof.

In another aspect, the present application relates to a method of modulating (e.g., inhibiting or decreasing the activity of) HER2 or a mutant thereof, comprising administering to a subject in need thereof an effective amount of a compound of the present application, or a pharmaceutically acceptable salt or solvate thereof.

In another aspect, the present application relates to a method of treating or preventing a disease or disorder, such as a kinase mediated disease or disorder, comprising administering to a subject in need thereof an effective amount of a compound of the present application, or a pharmaceutically acceptable salt or solvate thereof.

In another aspect, the present application relates to a method of treating or preventing a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel), comprising administering to a subject in need thereof an effective amount of a compound of the present application, or a pharmaceutically acceptable salt or solvate thereof.

In another aspect, the present application relates to a method of treating or preventing cancer, wherein the cancer cell comprises a mutant HER2, comprising administering to a subject in need thereof an effective amount of a compound of the present application, or a pharmaceutically acceptable salt or solvate thereof.

In another aspect, the present application relates to a method of treating or preventing a disease or disorder, such as a kinase mediated disease or disorder, in a subject in need thereof, wherein the subject is identified as being in need of modulation (e.g., inhibition or decrease of the activity) of HER2 or a mutant thereof for the treatment or prevention of the disease or disorder, comprising administering to the subject an effective amount of a compound of the present application, or a pharmaceutically acceptable salt or solvate thereof.

In another aspect, the present application relates to a compound of the present application, or a pharmaceutically acceptable salt or solvate thereof, for modulating (e.g., inhibiting or decreasing the activity of) HER2 or a mutant thereof; for treating or preventing a disease or disorder, such as a kinase mediated disease or disorder; for treating or preventing a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for treating or preventing cancer, wherein the cancer cell comprises a mutant HER2; or for treating or preventing a disease or disorder, such as a kinase mediated disease or disorder in a subject identified as being in need of modulation (e.g., inhibition or decrease of the activity) of HER2 or a mutant thereof for the treatment or prevention of the disease or disorder.

In another aspect, the present application relates to a compound of the present application, or a pharmaceutically acceptable salt or solvate thereof, for use in the modulation (e.g., inhibition or decrease of the activity) of HER2 or a mutant thereof; in the treatment or prevention of a disease or disorder, such as a kinase mediated disease or disorder: in the treatment or prevention of a disease or disorder resistant to a HER2 targeted therapy (e.g., a therapy with afatinib, neratinib, and/or dacomitinib, trastuzumab and/or chemotherapy, with lapatinib and/or taxane, with neratinib and/or paclitaxel, or with trastuzumab and/or paclitaxel); in the treatment or prevention of cancer, wherein the cancer cell comprises a mutant HER2; or in the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

In another aspect, the present application relates to use of a compound of the present application, or a pharmaceutically acceptable salt or solvate thereof, in the modulation (e.g., inhibition or decrease of the activity) of HER2 or a mutant thereof; in the treatment or prevention of a disease or disorder, such as a kinase mediated disease or disorder; in the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); in the treatment or prevention of cancer, wherein the cancer cell comprises a mutant HER2; or in the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

In another aspect, the present application relates to a compound of the present application, or a pharmaceutically acceptable salt or solvate thereof, for use in the manufacture of a medicament for the modulation (e.g., inhibition or decrease of the activity) of HER2 or a mutant thereof; for the treatment or prevention of a disease or disorder, such as a kinase mediated disease or disorder; for the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for the treatment or prevention of cancer, wherein the cancer cell comprises a mutant HER2; or for the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

In another aspect, the present application relates to use of a compound of the present application, or a pharmaceutically acceptable salt or solvate thereof, in the manufacture of a medicament for the modulation (e.g., inhibition or decrease of the activity) of HER2 or a mutant thereof; for the treatment or prevention of a disease or disorder, such as a kinase mediated disease or disorder; for the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for the treatment or prevention of cancer, wherein the cancer cell comprises a mutant HER2; or for the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

The details of the application are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference.

DETAILED DESCRIPTION

Compounds of the Application

Figure 1A:
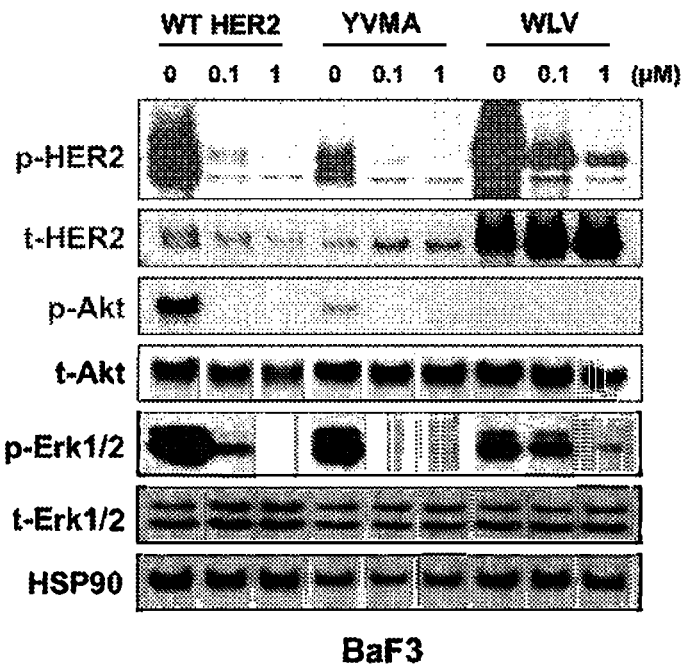
FIG. 1A is a Western blot showing the effects of Compound 1 on HER2 phosphorylation and its downstream signaling components at the indicated concentrations in Ba/F3 cells expressing wild-type HER2, HER2 InsYVMA mutant ("YVMA"), or HER2 InsWLV mutant ("WLV"), treated with Compound 1 for 6 hours.

The present application relates to a compound of Formula I:

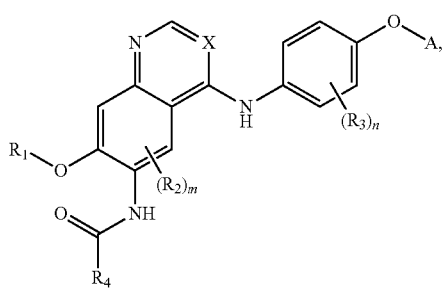

or a pharmaceutically acceptable salt or solvate thereof, wherein:

A is naphthyl or bicyclic heteroaryl comprising two 5- or 6-membered rings and 1-4 heteroatoms selected from N, O, and S, and is optionally substituted with one or more $R_4$;

each $R_4$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino;

X is N or C—CN;

$R_1$ is $C_1$-$C_6$ alkyl or $(CH_2)_{1-3}$-heterocyclyl comprising one 5- or 6-membered ring and 1-3 heteroatoms selected N and O and at least one N, wherein the alkyl is optionally substituted with one or more $R_B'$ and the heterocyclyl is optionally substituted with one or more $R_B$;

m is 0, 1, or 2;

each $R_2$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, di-$C_1$-$C_6$ alkylamino, or NHC(O)$R_5$;

n is 0, 1, 2, 3 or 4;

each $R_3$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino;

$R_4$ and $R_5$ are each independently $C_2$-$C_4$ alkenyl optionally substituted with one or more $R_x$;

each $R_x$ is independently $NH_2$, $C_1$-$C_3$ alkylamino, di-$C_1$-$C_3$ alkylamino, or heterocyclyl comprising a 4- to 7-membered ring and 1-3 heteroatoms selected from N, O, and S, wherein the heterocyclyl is optionally substituted with one or more substituents independently selected from halogen, OH, and C(O)($C_1$-$C_3$) alkyl;

each $R_B'$ is independently $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino; and each $R_B$ is independently $C_1$-$C_6$ alkyl, $C_1$-$C_6$ haloalkyl, or $R_B'$, wherein when A is 4-quinolinyl and n is 1, then $R_3$ is not halogen.

(I-1) In one embodiment, A is naphthyl optionally substituted with one or more $R_4$. In one embodiment, A is naphthyl.

(I-2) In one embodiment, A is bicyclic heteroaryl comprising two 5- or 6-membered rings and 1-4 heteroatoms selected from N, O, and S, and is optionally substituted with one or more $R_4$. In one embodiment, A is bicyclic heteroaryl comprising one 5-membered ring and one 6-membered ring. In one embodiment, A is bicyclic heteroaryl comprising two 6-membered rings. In one embodiment, A is bicyclic heteroaryl comprising two 5-membered rings. In one embodiment, A is bicyclic heteroaryl comprising 1 heteroatom. In one embodiment, A is bicyclic heteroaryl comprising 2 heteroatoms. In one embodiment, A is bicyclic heteroaryl comprising 3 heteroatoms. In one embodiment, A is bicyclic heteroaryl comprising 4 heteroatoms. In one embodiment, the heteroatoms are selected from N and O. In one embodiment, the heteroatoms are selected from N and S. In one embodiment, the heteroatoms are selected from O and S. In one embodiment, the heteroatoms are N.

(I-3) In one embodiment, A is

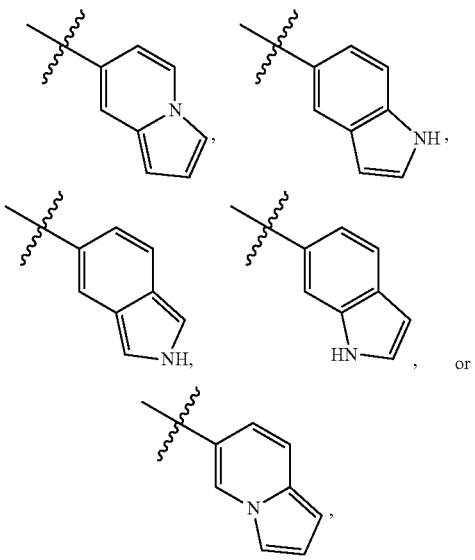

and is optionally substituted with one or more $R_4$. In one embodiment, A is

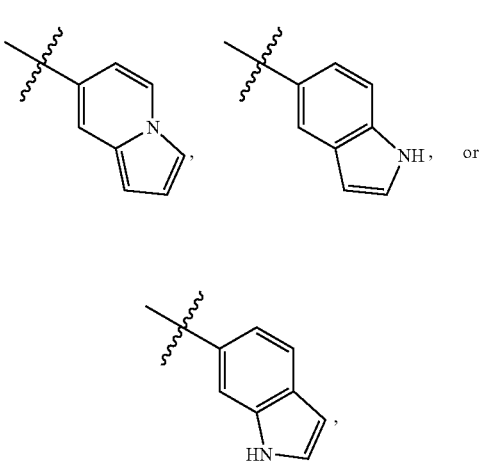

and is optionally substituted with one or more $R_A$. In one embodiment, A is
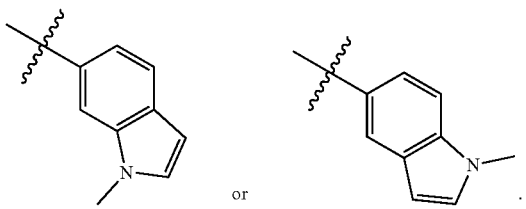 [SMILES: *c1ccc2ccn(C)c2c1 ; *c1ccc2c(ccn2C)c1]
or
(I-4) In one embodiment. A is
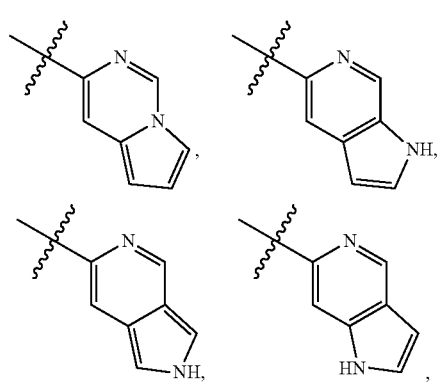
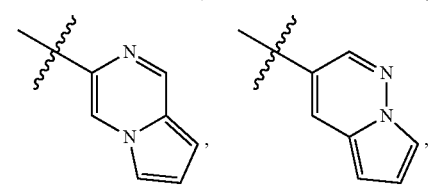
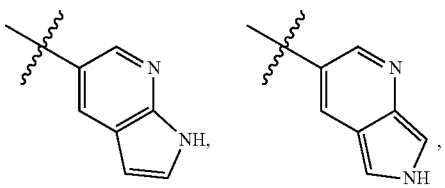
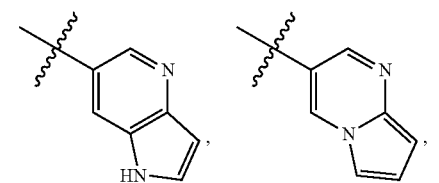
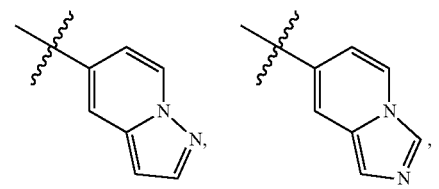
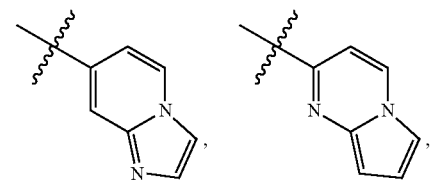
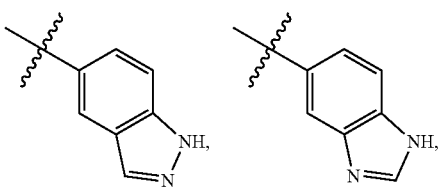
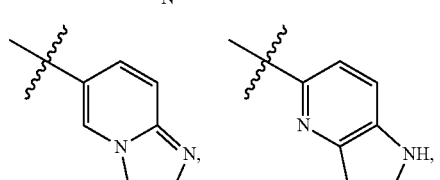
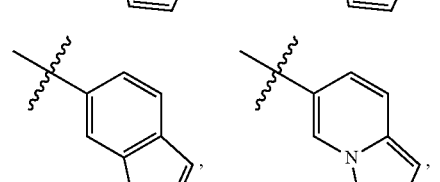
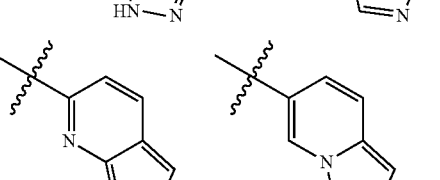
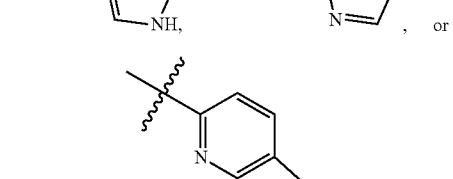
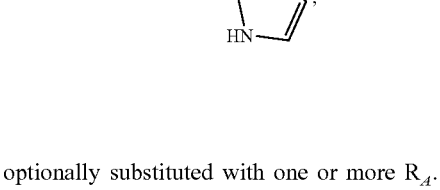
, or
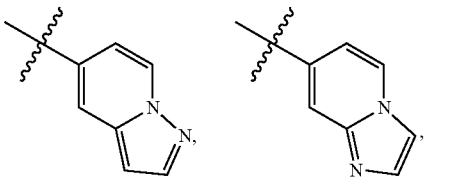
and is optionally substituted with one or more $R_A$. In one embodiment, A is
or
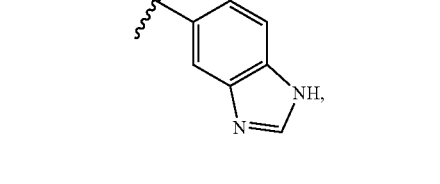
and is optionally substituted with one or more $R_A$.

(I-5) In one embodiment, A is
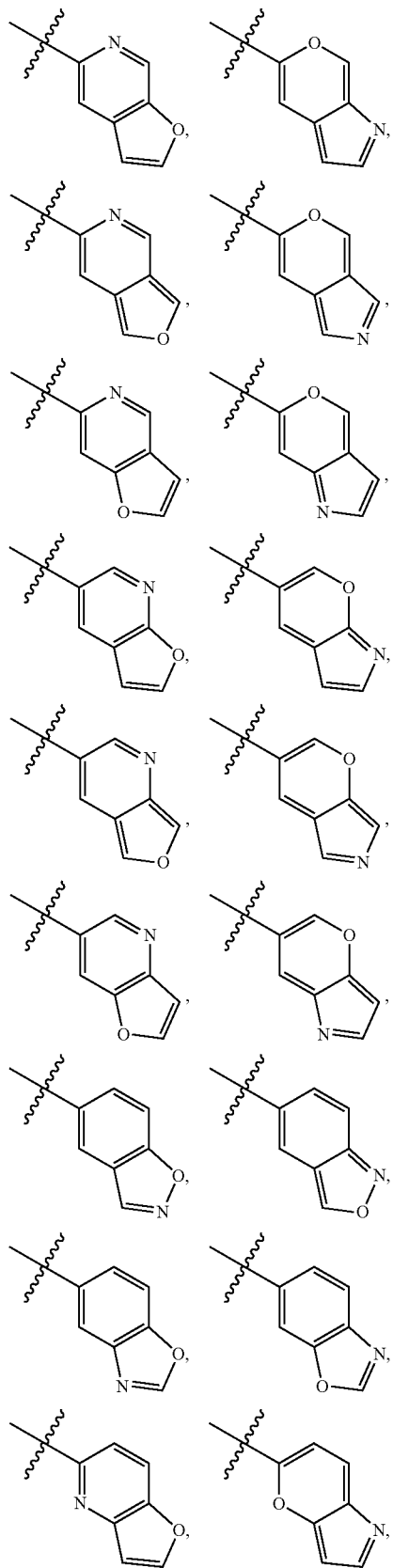
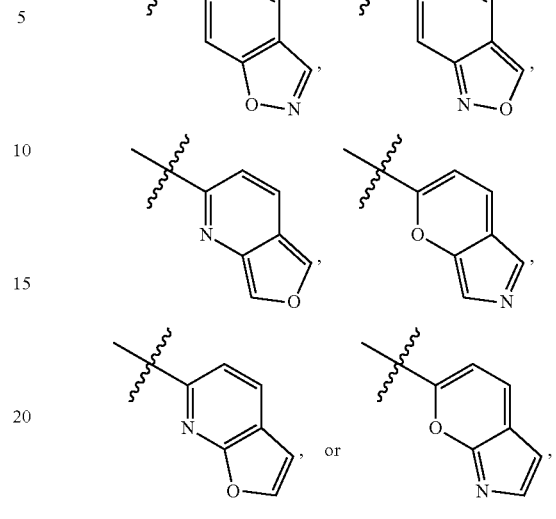
and is optionally substituted with one or more $R_A$.
(I-6) In one embodiment, A is
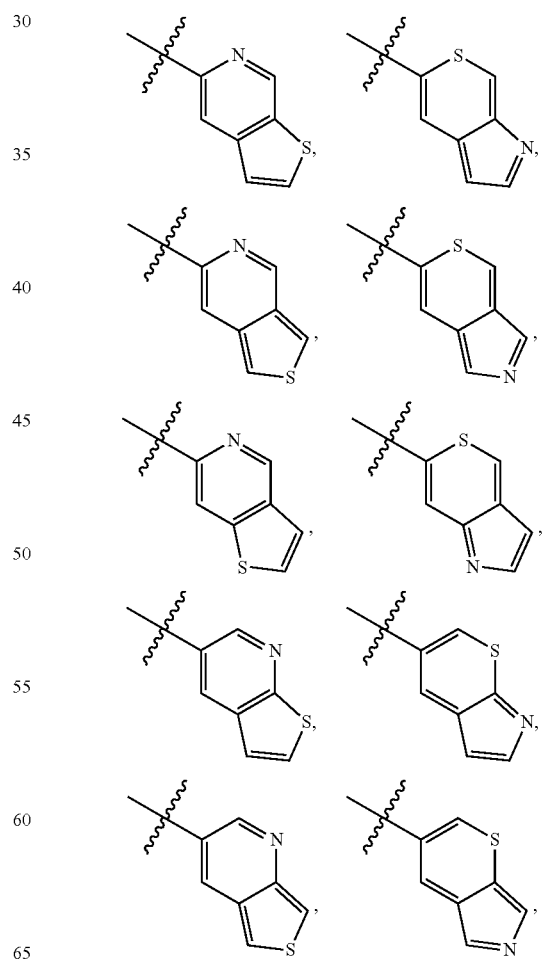

-continued
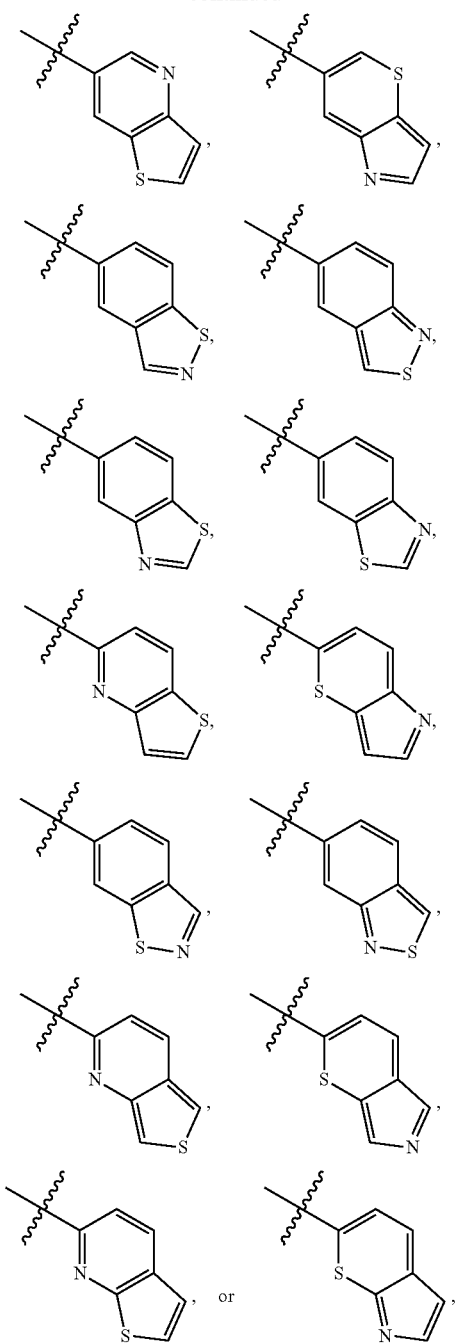
and is optionally substituted with one or more $R_A$. In one embodiment, A is
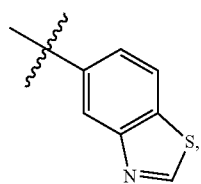 [SMILES: *c1ccc2scnc2c1]
and is optionally substituted with one or more $R_A$.
(I-7) In one embodiment, A is
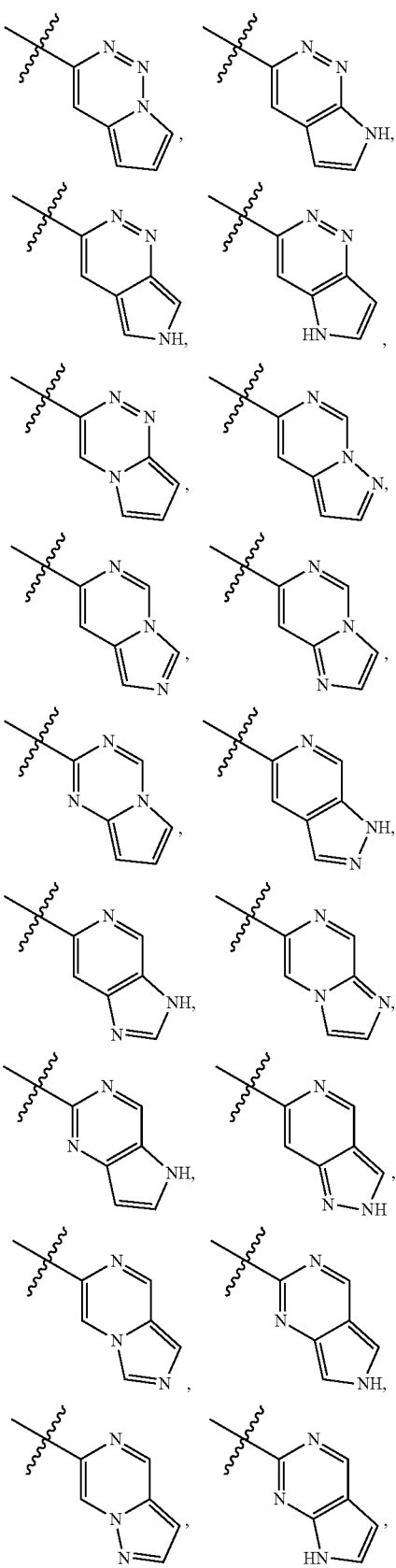

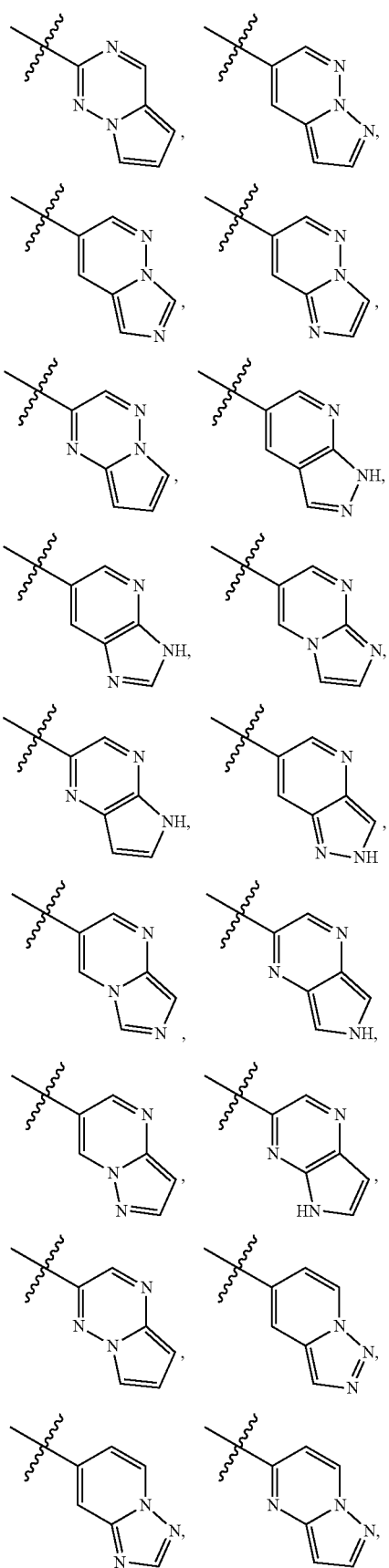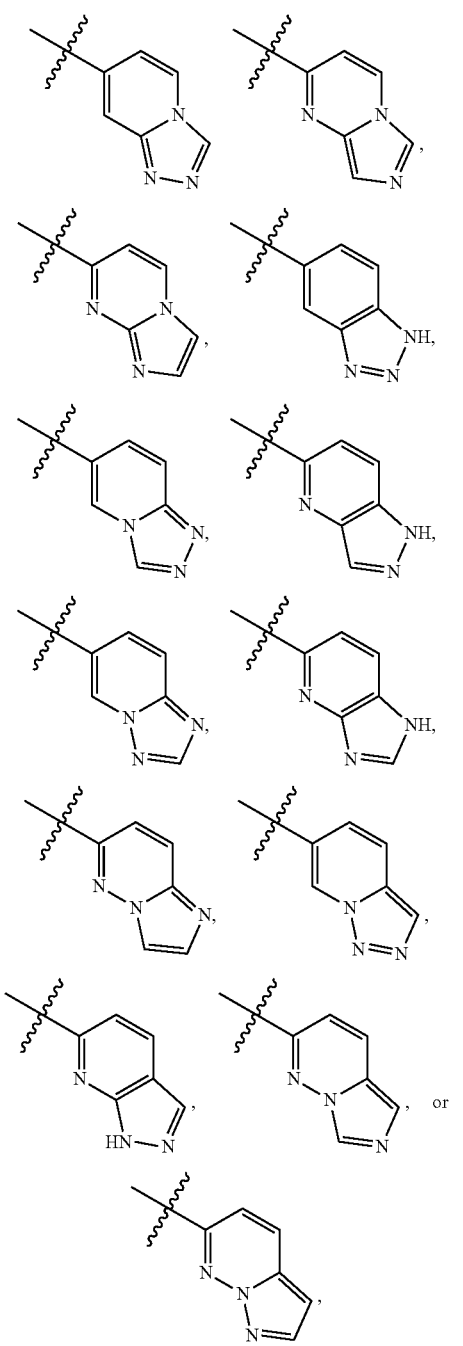
and is optionally substituted with one or more $R_A$. In one embodiment, A is
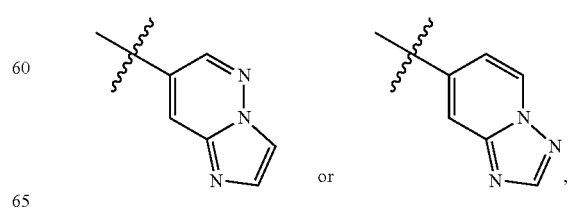
and is optionally substituted with one or more $R_A$.

(I-8) In one embodiment, A is

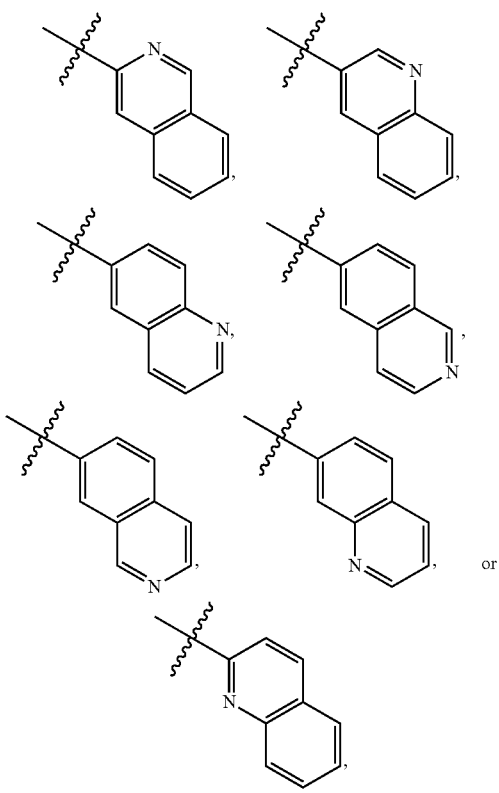

and is optionally substituted with one or more $R_A$. In one embodiment, A is

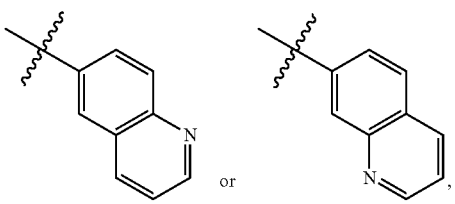 [SMILES: *c1ccc2ncccc2c1 ; *c1ccc2cccnc2c1]

and is optionally substituted with one or more $R_A$.

(II-1) In one embodiment, each $R_A$ is independently $C_1$-$C_6$ alkyl (e.g., methyl, ethyl, n-propyl, i-propyl, n-butyl, i-butyl, s-butyl, t-butyl, pentyl, or hexyl). In one embodiment, each $R_A$ is independently $C_1$-$C_3$ alkyl (e.g., methyl, ethyl, n-propyl, or i-propyl). In one embodiment, at least one $R_A$ is methyl. In one embodiment, at least one $R_A$ is ethyl. In one embodiment, at least one $R_A$ is propyl. In one embodiment, at least one $R_A$ is butyl. In one embodiment, at least one $R_A$ is pentyl. In one embodiment, at least one $R_A$ is hexyl.

(II-2) In one embodiment, each $R_A$ is independently $C_1$-$C_6$ haloalkyl (e.g., methyl, ethyl, n-propyl, i-propyl, n-butyl, i-butyl, s-butyl, t-butyl, pentyl, or hexyl, each of which is substituted with one or more halogen (e.g., F, Cl, Br, or I)). In one embodiment, each $R_A$ is independently $C_1$-$C_6$ fluoroalkyl. In one embodiment, each $R_A$ is independently $C_1$-$C_6$ chloroalkyl. In one embodiment, each $R_A$ is independently $C_1$-$C_6$ bromoalkyl. In one embodiment, each $R_A$ is independently $C_1$-$C_6$ iodoalkyl.

(II-3) In one embodiment, each $R_A$ is independently $C_1$-$C_6$ alkoxy (e.g., methoxy, ethoxy, n-propoxy, i-propoxy, n-butoxy, i-butoxy, s-butoxy, t-butoxy, pentoxy, or hexyloxy). In one embodiment, at least one $R_A$ is methoxy. In one embodiment, at least one $R_A$ is ethoxy. In one embodiment, at least one $R_A$ is propoxy. In one embodiment, at least one $R_A$ is butoxy. In one embodiment, at least one $R_A$ is pentoxy. In one embodiment, at least one $R_A$ is hexyloxy.

(II-4) In one embodiment, each $R_A$ is independently $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, each $R_A$ is independently $C_1$-$C_6$ fluoroalkoxy. In one embodiment, each $R_A$ is independently $C_1$-$C_6$ bromoalkoxy. In one embodiment, each $R_A$ is independently $C_1$-$C_6$ iodoalkoxy.

(II-5) In one embodiment, each $R_A$ is independently halogen. OH, CN, or $NO_2$. In one embodiment, at least one $R_A$ is halogen. In one embodiment, at least one $R_A$ is F. In one embodiment, at least one $R_A$ is Cl. In one embodiment, at least one $R_A$ is Br. In one embodiment, at least one $R_A$ is I. In one embodiment, at least one $R_A$ is OH. In one embodiment, at least one $R_A$ is CN. In one embodiment, at least one $R_A$ is $NO_2$.

(II-6) In one embodiment, each $R_A$ is independently $NH_2$, $C_1$-$C_6$ alkylamino, or di-$C_1$-$C_6$ alkylamino, wherein the $C_1$-$C_6$ alkyl moiety is selected from methyl, ethyl, n-propyl, i-propyl, n-butyl, i-butyl, s-butyl, t-butyl, pentyl, and hexyl. In one embodiment, at least one $R_A$ is $NH_2$. In one embodiment, each $R_A$ is independently $C_1$-$C_6$ alkylamino. In one embodiment, each $R_A$ is independently di-$C_1$-$C_6$ alkylamino. In one embodiment, at least one $R_A$ is di-methyl-amino. In one embodiment, at least one $R_A$ is di-ethyl-amino. In one embodiment, at least one $R_A$ is di-propyl-amino.

(III-1) In one embodiment, X is N.
(III-2) In one embodiment, X is C—CN.
(IV-1) In one embodiment, $R_1$ is $C_1$-$C_6$ alkyl (e.g., methyl, ethyl, n-propyl, i-propyl, n-butyl, i-butyl, s-butyl, t-butyl, pentyl, or hexyl), wherein the alkyl is optionally substituted with one or more $R_B'$. In one embodiment, $R_1$ is methyl optionally substituted with one or more $R_B'$. In one embodiment, $R_1$ is ethyl optionally substituted with one or more $R_B'$. In one embodiment, $R_1$ is propyl optionally substituted with one or more $R_B'$. In one embodiment, $R_1$ is butyl optionally substituted with one or more $R_B'$. In one embodiment, $R_1$ is pentyl optionally substituted with one or more $R_B'$. In one embodiment. $R_1$ is hexyl optionally substituted with one or more $R_B'$. In one embodiment, $R_1$ is

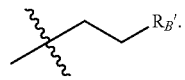

In one embodiment, $R_1$ is

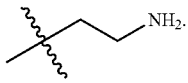

In one embodiment. $R_1$ is

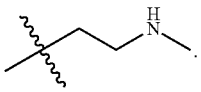

In one embodiment, $R_1$ is

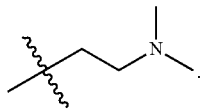 [SMILES: *CCN(C)C]

(IV-2) In one embodiment, $R_1$ is $(CH_2)_{1-3}$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_2$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_3$-heterocyclyl comprising one 5- or 6-membered ring and 1-3 heteroatoms selected N and O and at least one N, wherein the heterocyclyl is optionally substituted with one or more $R_B$. In one embodiment, the heterocyclyl comprises one 5-membered ring. In one embodiment, the heterocyclyl comprises one 6-membered ring. In one embodiment, the heterocyclyl comprises one N. In one embodiment, the heterocyclyl comprises one N and one O. In one embodiment, the heterocyclyl comprises two N. In one embodiment, the heterocyclyl comprises one N and two O. In one embodiment, the heterocyclyl comprises two N and one O. In one embodiment, the heterocyclyl comprises three N. In one embodiment, the heterocyclyl is

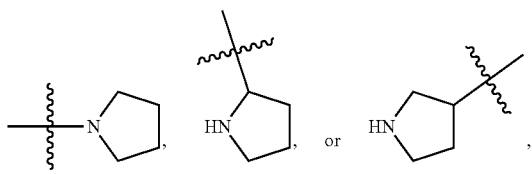 [SMILES: *N1CCCC1 ; *C1CCCN1 ; *C1CCNC1]

and is optionally substituted with one or more $R_B$. In one embodiment, the heterocyclyl is

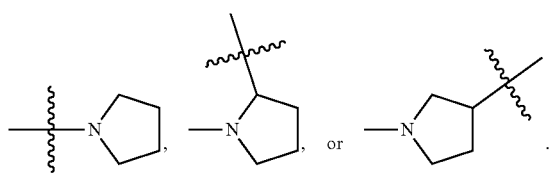

In one embodiment, $R_1$ is

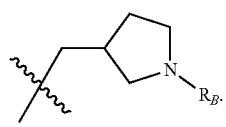

In one embodiment, $R_1$ is

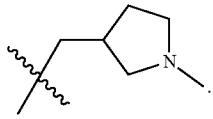 [SMILES: *CC1CCN(C)C1]

In one embodiment, $R_1$ is

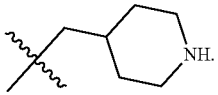 [SMILES: *CC1CCNCC1]

In one embodiment, $R_1$ is

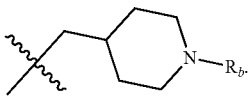

In one embodiment, $R_1$ is

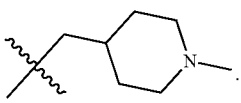 [SMILES: *CC1CCN(C)CC1]

(V-1) In one embodiment, m is 0.
(V-2) In one embodiment, m is 1.
(V-3) In one embodiment, m is 2.
(VI-1) In one embodiment, each $R_2$ is independently $C_1$-$C_6$ alkyl (e.g., methyl, ethyl, n-propyl, i-propyl, n-butyl, i-butyl, s-butyl, t-butyl, pentyl, or hexyl). In one embodiment, at least one $R_2$ is methyl. In one embodiment, at least one $R_2$ is ethyl. In one embodiment, at least one $R_2$ is propyl. In one embodiment, at least one $R_2$ is butyl. In one embodiment, at least one $R_2$ is pentyl. In one embodiment, at least one $R_2$ is hexyl.

(VI-2) In one embodiment, each $R_2$ is independently $C_1$-$C_6$ haloalkyl (e.g., methyl, ethyl, n-propyl, i-propyl, n-butyl, i-butyl, s-butyl, t-butyl, pentyl, or hexyl, each of which is substituted with one or more halogen (e.g., F, Cl, Br, or I)). In one embodiment, each $R_2$ is independently $C_1$-$C_6$ fluoroalkyl. In one embodiment, each $R_2$ is independently $C_1$-$C_6$ bromoalkyl. In one embodiment, each $R_2$ is independently $C_1$-$C_6$ iodoalkyl.

(VI-3) In one embodiment, each $R_2$ is independently $C_1$-$C_6$ alkoxy (e.g., methoxy, ethoxy, n-propoxy, i-propoxy, n-butoxy, i-butoxy, s-butoxy, t-butoxy, pentoxy, or hexyloxy). In one embodiment, at least one $R_2$ is methyloxy. In one embodiment, at least one $R_2$ is ethyloxy. In one embodiment, at least one $R_2$ is propyloxy. In one embodiment, at least one $R_2$, is butyloxy. In one embodiment, at least one $R_2$ is pentyloxy. In one embodiment, at least one $R_2$ is hexyloxy.

(VI-4) In one embodiment, each $R_2$ is independently $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, each $R_2$ is independently $C_1$-$C_6$ fluoroalkoxy. In one embodiment, each $R_2$ is independently $C_1$-$C_6$ bromoalkoxy. In one embodiment, each $R_2$ is independently $C_1$-$C_6$ iodoalkoxy.

(VI-5) In one embodiment, each $R_2$ is independently halogen, OH, CN, or $NO_2$. In one embodiment, at least one $R_2$, is halogen. In one embodiment, at least one $R_2$ is F. In one embodiment, at least one $R_2$ is Cl. In one embodiment, at least one $R_2$, is Br. In one embodiment, at least one $R_2$ is 1. In one embodiment, at least one $R_2$ is OH. In one embodiment, at least one $R_2$ is CN. In one embodiment, at least one $R_2$ is $NO_2$.

(VI-6) In one embodiment, each $R_2$ is independently $NH_2$, $C_1$-$C_6$ alkylamino, or di-$C_1$-$C_6$ alkylamino, wherein the $C_1$-$C_6$ alkyl moiety is selected from methyl, ethyl, n-propyl, i-propyl, n-butyl, i-butyl, s-butyl, t-butyl, pentyl, and hexyl. In one embodiment, at least one $R_2$ $NH_2$. In one embodiment, each $R_2$ is independently $C_1$-$C_6$ alkylamino. In one embodiment, each $R_2$ is independently di-$C_1$-$C_6$ alkylamino. In one embodiment, at least one $R_2$ di-methyl-amino. In one embodiment, at least one $R_2$ di-ethyl-amino. In one embodiment, at least one $R_2$ di-propyl-amino.

(VI-7) In one embodiment, each $R_2$ is $NHC(O)R_5$.

(VII-1) In one embodiment, n is 0.
(VII-2) In one embodiment, n is 1.
(VII-3) In one embodiment, n is 2.
(VII-4) In one embodiment, n is 3.
(VII-5) In one embodiment, n is 4.

(VIII-1) In one embodiment, each $R_3$ is independently $C_1$-$C_6$ alkyl (e.g., methyl, ethyl, n-propyl, i-propyl, n-butyl, i-butyl, s-butyl, t-butyl, pentyl, or hexyl) or halogen. In one embodiment, each $R_3$ is independently methyl, ethyl, F, or Cl. In one embodiment, each $R_3$ is independently methyl or F. In one embodiment, each $R_3$ is independently methyl or Cl. In one embodiment, each $R_3$ is independently ethyl or F. In one embodiment, each $R_3$ is independently ethyl or Cl.

(VIII-2) In one embodiment, each $R_3$ is independently $C_1$-$C_6$ alkyl (e.g., methyl, ethyl, n-propyl, i-propyl, n-butyl, i-butyl, s-butyl, t-butyl, pentyl, or hexyl). In one embodiment, at least one $R_3$ is methyl. In one embodiment, at least one $R_3$ is ethyl. In one embodiment, at least one $R_3$ is propyl. In one embodiment, at least one $R_3$ is butyl. In one embodiment, at least one $R_3$ is pentyl. In one embodiment, at least one $R_3$ is hexyl.

(VIII-3) In one embodiment, each $R_3$ is independently halogen. In one embodiment, at least one $R_3$ is F. In one embodiment, at least one $R_3$ is Cl. In one embodiment, at least one $R_3$ is Br. In one embodiment, at least one $R_3$ is Cl. In one embodiment, at least one $R_3$ is I.

(VIII-4) In one embodiment, each $R_5$ is independently $C_1$-$C_6$ haloalkyl (e.g., methyl, ethyl, n-propyl, i-propyl, n-butyl, i-butyl, s-butyl, t-butyl, pentyl, or hexyl, each of which is substituted with one or more halogen (e.g., F, Cl, Br, or I)), $C_1$-$C_6$ alkoxy (e.g., methoxy, ethoxy, n-propoxy, i-propoxy, n-butoxy, i-butoxy, s-butoxy, t-butoxy, pentoxy, or hexyloxy), or $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, each $R_3$ is independently $C_1$-$C_6$ fluoroalkyl. In one embodiment, each $R_2$ is independently $C_1$-$C_6$ bromoalkyl. In one embodiment, each $R_3$ is independently $C_1$-$C_6$ iodoalkyl. In one embodiment, at least one $R_3$ is methyloxy. In one embodiment, at least one $R_3$ is ethyloxy. In one embodiment, at least one $R_3$ is propyloxy. In one embodiment, at least one $R_3$ is butyloxy. In one embodiment, at least one $R_3$ is pentyloxy. In one embodiment, at least one $R_3$ is hexyloxy. In one embodiment, each $R_3$ is independently $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, each $R_3$ is independently $C_1$-$C_6$ fluoroalkoxy. In one embodiment, each $R_3$ is independently $C_1$-$C_6$ bromoalkoxy. In one embodiment, each $R_3$ is independently $C_1$-$C_6$ iodoalkoxy.

(VIII-5) In one embodiment, each $R_3$ is independently OH, CN, or $NO_2$. In one embodiment, at least one $R_3$ is OH. In one embodiment, at least one $R_3$ is CN. In one embodiment, at least one $R_3$ is $NO_2$.

(VIII-6) In one embodiment, each $R_3$ is independently $NH_2$, $C_1$-$C_6$ alkylamino, or di-$C_1$-$C_6$ alkylamino, wherein the $C_1$-$C_6$ alkyl moiety is selected from methyl, ethyl, n-propyl, i-propyl, n-butyl, i-butyl, s-butyl, t-butyl, pentyl, and hexyl. In one embodiment, at least one $R_3$ is $NH_2$. In one embodiment, each $R_3$ is independently $C_1$-$C_6$ alkylamino. In one embodiment, each $R_3$ is independently di-$C_1$-$C_6$ alkylamino. In one embodiment, at least one $R_3$ is di-methyl-amino. In one embodiment, at least one $R_3$ is di-ethyl-amino. In one embodiment, at least one $R_3$ is di-propyl-amino.

(IX-1) In one embodiment, $R_4$ is $C_2$-$C_4$ alkenyl (e.g., ethenyl, propenyl, or butenyl) optionally substituted with one or more $R_x$.

(IX-2) In one embodiment, $R_4$ is ethenyl optionally substituted with one or more $R_x$. In one embodiment, $R_4$ is ethenyl.

(IX-3) In one embodiment, $R_4$ is propenyl optionally substituted with one or more $R_x$. In one embodiment, $R_4$ is 1-propenyl optionally substituted with one or more $R_x$. In one embodiment, $R_4$ is

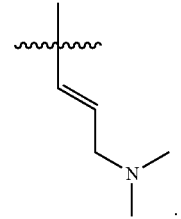

In one embodiment, $R_4$ is 1-propenyl. In one embodiment, $R_4$ is 2-propenyl optionally substituted with one or more $R_x$. In one embodiment, $R_4$ is 2-propenyl.

(IX-4) In one embodiment. $R_4$ is butenyl optionally substituted with one or more $R_x$. In one embodiment, $R_4$ is 1-butenyl optionally substituted with one or more $R_x$. In one embodiment, $R_4$ is 1-butenyl. In one embodiment, $R_4$ is 2-butenyl optionally substituted with one or more $R_x$. In one embodiment, $R_4$ is 2-butenyl. In one embodiment, $R_4$ is 3-butenyl optionally substituted with one or more $R_x$. In one embodiment, $R_4$ is 3-butenyl.

(X-1) In one embodiment, $R_5$ is $C_2$-$C_4$ alkenyl optionally substituted with one or more $R_x$.

(X-2) In one embodiment, $R_5$ is ethenyl optionally substituted with one or more $R_x$. In one embodiment, $R_5$ is ethenyl.

(X-3) In one embodiment, $R_5$ is propenyl optionally substituted with one or more $R_x$. In one embodiment, $R_5$ is 1-propenyl optionally substituted with one or more $R_x$. In one embodiment, $R_5$ is 1-propenyl. In one embodiment, $R_5$ is 2-propenyl optionally substituted with one or more $R_x$. In one embodiment, $R_5$ is 2-propenyl.

(X-4) In one embodiment. $R_5$ is butenyl optionally substituted with one or more $R_x$. In one embodiment, $R_5$ is 1-butenyl optionally substituted with one or more $R_x$. In one embodiment. $R_5$ is 1-butenyl. In one embodiment, $R_5$ is 2-butenyl optionally substituted with one or more $R_x$. In one embodiment, $R_5$ is butenyl. In one embodiment, $R_5$ is 3-butenyl optionally substituted with one or more $R_x$. In one embodiment, $R_5$ is 3-butenyl.

(XI-1) In one embodiment, each $R_x$ is independently $NH_2$, $C_1$-$C_3$ alkylamino, or di-$C_1$-$C_3$ alkylamino, wherein the is $C_1$-$C_3$ alkyl moiety is methyl, ethyl, propyl, or i-propyl. In one embodiment, at least one $R_x$ is $NH_2$. In one embodiment, each $R_A$ is independently $C_1$-$C_3$ alkylamino. In one embodiment, each $R_x$ is independently di-$C_1$-$C_3$ alkylamino. In one embodiment, at least one $R_x$ is di-methyl-amino. In one embodiment, at least one $R_x$ is di-ethyl-amino. In one embodiment, at least one $R_x$ is di-propyl-amino.

(XI-2) In one embodiment, each $R_x$ is independently heterocyclyl comprising a 4- to 7-membered ring and 1-3 heteroatoms selected from N, O, and S, wherein the heterocyclyl is optionally substituted with one or more substituents independently selected from halogen, OH, and $C(O)(C_1$-$C_3)$ alkyl. In one embodiment, the heterocycle comprises a 4-membered ring. In one embodiment, the heterocycle comprises a 5-membered ring. In one embodiment, the heterocycle comprises a 6-membered ring. In one embodiment, the heterocycle comprises a 7-membered ring. In one embodiment, the heterocycle comprises one heteroatom selected from N, O, and S. In one embodiment, the heterocycle comprises one N. In one embodiment, the heterocycle comprises one O. In one embodiment, the heterocycle comprises one S. In one embodiment, the heterocycle comprises two heteroatoms selected from N, O, and S. In one embodiment, the heterocycle comprises two N. In one embodiment, the heterocycle comprises one N and one O. In one embodiment, the heterocycle comprises one N and one S. In one embodiment, the heterocycle comprises three heteroatoms selected from N, O, and S. In one embodiment, the heterocycle comprises three N. In one embodiment, the heterocycle comprises two N and one O. In one embodiment, the heterocycle comprises two N and one S.

(XII-1) In one embodiment, each $R_B'$ is independently $C_1$-$C_6$ alkoxy (e.g., methoxy, ethoxy, n-propoxy, i-propoxy, n-butoxy, i-butoxy, s-butoxy, t-butoxy, pentoxy, or hexyloxy). In one embodiment, at least one $R_B'$ is methyloxy. In one embodiment, at least one $R_B'$ is ethyloxy. In one embodiment, at least one $R_B'$ is propyloxy. In one embodiment, at least one $R_B'$ is butyloxy. In one embodiment, at least one $R_B'$ is pentyloxy. In one embodiment, at least one $R_B'$ is hexyloxy.

(XII-2) In one embodiment, each $R_B'$ is independently $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, each $R_B'$ is independently $C_1$-$C_6$ fluoroalkoxy. In one embodiment, each $R_B'$ is independently $C_1$-$C_6$ bromoalkoxy. In one embodiment, each $R_B'$ is independently $C_1$-$C_6$ iodoalkoxy.

(XII-3) In one embodiment, each $R_B'$ is independently halogen, OH, CN, or $NO_2$. In one embodiment, each $R_B'$ is independently halogen. In one embodiment, at least one $R_B'$ is F. In one embodiment, at least one $R_B'$ is Cl. In one embodiment, at least one $R_B'$ is Br. In one embodiment, at least one $R_B'$ is I. In one embodiment, at least one $R_B'$ is OH. In one embodiment, at least one $R_B'$ is CN. In one embodiment, at least one $R_B'$ is $NO_2$.

(XII-4) In one embodiment, each $R_B'$ is independently $NH_2$, $C_1$-$C_6$ alkylamino, or di-$C_1$-$C_6$, alkylamino, wherein the $C_1$-$C_6$ alkyl moiety is selected from methyl, ethyl, n-propyl, i-propyl, n-butyl, i-butyl, s-butyl, t-butyl, pentyl, and hexyl. In one embodiment, at least one $R_B'$ is $NH_2$. In one embodiment, each $R_B'$ is independently $C_1$-$C_6$ alkylamino. In one embodiment, each $R_B'$ is independently di-$C_1$-$C_6$ alkylamino. In one embodiment, at least one $R_B'$ is di-methyl-amino. In one embodiment, at least one $R_B'$ is di-ethyl-amino. In one embodiment, at least one $R_B'$ is di-propyl-amino.

(XIII-1) In one embodiment, each $R_B$ is independently $C_1$-$C_6$ alkyl (e.g., methyl, ethyl, n-propyl, i-propyl, n-butyl, i-butyl, s-butyl, t-butyl, pentyl, or hexyl). In one embodiment, at least one $R_B$ is methyl. In one embodiment, at least one $R_B$ is ethyl. In one embodiment, at least one $R_B$ is propyl. In one embodiment, at least one $R_B$ is butyl. In one embodiment, at least one $R_B$ is pentyl. In one embodiment, at least one $R_B$ is hexyl.

(XIII-2) In one embodiment, each $R_B$ is independently $C_1$-$C_6$ haloalkyl (e.g., methyl, ethyl, n-propyl, i-propyl, n-butyl, i-butyl, s-butyl, t-butyl, pentyl, or hexyl, each of which is substituted with one or more halogen (e.g., F, Cl, Br, or I)). In one embodiment, each $R_B$ is independently $C_1$-$C_6$ fluoroalkyl. In one embodiment, each $R_B$ is independently $C_1$-$C_6$ bromoalkyl. In one embodiment, each $R_B$ is independently $C_1$-$C_6$ iodoalkyl.

(XIII-3) In one embodiment, at least one $R_B$ is $R_B'$, as described herein.

(XIV-1) In one embodiment, X is C—CN; and $R_1$ is $C_1$-$C_6$ alkyl (e.g., methyl, ethyl, n-propyl, i-propyl, n-butyl, i-butyl, s-butyl, t-butyl, pentyl, or hexyl). In one embodiment, X is C—CN; and $R_1$ is methyl or ethyl. In one embodiment, X is C—CN; and $R_1$ is methyl. In one embodiment, X is C—CN; and $R_1$ is ethyl.

(XIV-2) In one embodiment, X is C—CN; and $R_1$ is $C_1$-$C_6$ alkyl (e.g., methyl, ethyl, n-propyl, i-propyl, n-butyl, i-butyl, s-butyl, t-butyl, pentyl, or hexyl) substituted with one or more $R_B'$. In one embodiment, X is C—CN; and $R_1$ is $C_1$-$C_6$ alkyl (e.g., methyl, ethyl, n-propyl, i-propyl, n-butyl, i-butyl, s-butyl, t-butyl, pentyl, or hexyl) substituted with one or more $R_B'$, wherein each $R_B'$ is independently $NH_2$, $C_1$-$C_6$ alkylamino, or di-$C_1$-$C_6$ alkylamino. In one embodiment, X is C—CN; and $R_1$ is methyl or ethyl substituted with one or more $R_B'$, wherein each $R_B'$ is independently $NH_2$, $C_1$-$C_6$ alkylamino, or di-$C_1$-$C_6$ alkylamino. In one embodiment, X is C—CN; and $R_1$ is

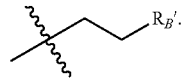

In one embodiment, X is C—CN; and $R_1$ is

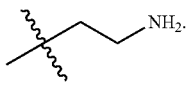 [SMILES: *CCN]

In one embodiment, X is C—CN; and $R_1$ is

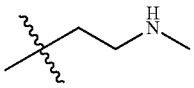

In one embodiment, X is C—CN; and $R_1$ is

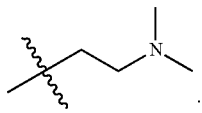 [SMILES: *CCN(C)C]

(XIV-3) In one embodiment, X is C—CN; and $R_1$ is $(CH_2)_{1-3}$-heterocyclyl comprising one 5- or 6-membered ring and 1-3 heteroatoms selected N and O and at least one N, and the heterocyclyl is optionally substituted with one or more $R_B$. In one embodiment, X is C—CN; and $R_1$ is $(CH_2)_{1-3}$-pyrrolidinyl, wherein the pyrrolidinyl is optionally substituted with one or more $R_B$. In one embodiment, X is C—CN; and $R_1$ is $(CH_2)$-pyrrolidinyl, wherein the pyrrolidinyl is optionally substituted with one or more $R_B$. In one embodiment, X is C—CN, and $R_1$ is

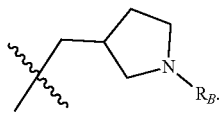

In one embodiment. X is C—CN, and $R_1$ is

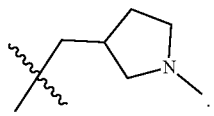

(XIV-4) In one embodiment, X is N; and $R_1$ is $C_1$-$C_6$ alkyl (e.g., methyl, ethyl, n-propyl, i-propyl, n-butyl, i-butyl, s-butyl, t-butyl, pentyl, or hexyl). In one embodiment, X is N; and $R_1$ is methyl or ethyl. In one embodiment, X is N; and $R_1$ is methyl. In one embodiment, X is N; and $R_1$ is ethyl.

(XV-1) In one embodiment, n is 1; and $R_3$ is $C_1$-$C_6$ alkyl (e.g., methyl, ethyl, n-propyl, i-propyl, n-butyl, i-butyl, s-butyl, t-butyl, pentyl, or hexyl), $C_1$-$C_6$ haloalkyl (e.g., methyl, ethyl, n-propyl, i-propyl, n-butyl, i-butyl, s-butyl, t-butyl, pentyl, or hexyl, each of which is substituted with one or more halogen (e.g., F, Cl, Br, or I)), $C_1$-$C_6$ alkoxy (e.g., methoxy, ethoxy, n-propoxy, i-propoxy, n-butoxy, i-butoxy, s-butoxy, t-butoxy, pentoxy, or hexyloxy), or $C_1$-$C_6$ haloalkoxy (e.g., methoxy, ethoxy, n-propoxy, i-propoxy, n-butoxy, i-butoxy, s-butoxy, t-butoxy, pentoxy, or hexyloxy, each of which is substituted with one or more halogen (e.g., F, Cl, Br, or I)). In one embodiment, n is 1; and $R_3$ is $C_1$-$C_6$ alkyl (e.g., methyl, ethyl, n-propyl, i-propyl, n-butyl, i-butyl, s-butyl, t-butyl, pentyl, or hexyl). In one embodiment, n is 1; and $R_3$ is methyl of ethyl. In one embodiment, n is 1; and $R_3$ is methyl.

(XV-2) In one embodiment, n is 1; and $R_3$ is halogen, OH, CN, $NO_2$, $NH_2$, $C_1$-$C_6$ alkylamino, or di-$C_1$-$C_6$ alkylamino. In one embodiment, n is 1; and $R_3$ is halogen. In one embodiment, n is 1; and $R_3$ is Fl or Cl. In one embodiment, n is 1; and $R_3$ is F. In one embodiment, n is 1; and $R_3$ is Cl.

(XV-3) In one embodiment, n is 2; and each $R_3$ is independently $C_1$-$C_6$ alkyl (e.g., methyl, ethyl, n-propyl, i-propyl, n-butyl, i-butyl, s-butyl, t-butyl, pentyl, or hexyl) or halogen. In one embodiment, n is 2; and one $R_3$ is $C_1$-$C_6$ alkyl (e.g., methyl, ethyl, n-propyl, i-propyl, n-butyl, i-butyl, s-butyl, t-butyl, pentyl, or hexyl), and the other $R_3$ is halogen. In one embodiment, n is 2; and one $R_3$ is methyl or ethyl, and the other $R_3$ is F or Cl. In one embodiment, n is 2; and one $R_3$ is methyl, and the other $R_3$ is F or Cl. In one embodiment, n is 2; and one $R_3$ is methyl, and the other $R_3$ is F. In one embodiment, n is 2; and one $R_3$ is methyl, and the other $R_3$ is Cl.

Any of the substituents described herein for any of A, $R_A$, X, $R_1$, m, $R_2$, n, $R_3$, $R_4$, $R_5$, $R_x$, $R_B'$, and $R_B$ can be combined with any of the substituents described herein for one or more of the remainder of A, $R_A$, X, $R_1$, m, $R_2$, n, $R_3$, $R_4$, $R_5$, $R_x$, $R_B'$, and $R_B$.

(a1) In one embodiment of Formula I, X is as defined in (III-1), and $R_1$ is as defined in (IV-1).

(a2) In one embodiment of Formula I, X is as defined in (III-1), and $R_1$ is as defined in (IV-2).

(a3) In one embodiment of Formula I, X is as defined in (III-2), and $R_1$ is as defined in (IV-1).

(a4) In one embodiment of Formula I, X is as defined in (III-2), and $R_1$ is as defined in (IV-2).

(b1) In one embodiment of Formula I, X and $R_1$ are as defined in any of (a1)-(a4), and A is as defined in (I-1).

(b2) In one embodiment of Formula I. X and $R_1$ are as defined in any of (a1)-(a4), and A is as defined in (1-2).

(b3) In one embodiment of Formula I, X and $R_1$ are as defined in any of (a1)-(a4), and A is as defined in (I-3).

(b4) In one embodiment of Formula I, X and $R_1$ are as defined in any of (a1)-(a4), and A is as defined in (I-4).

(b5) In one embodiment of Formula I, X and $R_1$ are as defined in any of (a1)-(a4), and A is as defined in (1-5).

(b6) In one embodiment of Formula I, X and $R_1$ are as defined in any of (a1)-(a4), and A is as defined in (I-6).

(b7) In one embodiment of Formula I, X and $R_1$ are as defined in any of (a1)-(a4), and A is as defined in (I-7).

(b8) In one embodiment of Formula I, X and $R_1$ are as defined in any of (a1)-(a4), and A is as defined in (1-8).

(c1) In one embodiment of Formula I, A, X, and $R_1$ are as defined, as applicable, in any of (a1)-(b8), and $R_A$ is as defined as (II-1).

(c2) In one embodiment of Formula I, A, X, and $R_1$ are as defined, as applicable, in any of (a1)-(b8), and $R_A$ is as defined as (II-2).

(c3) In one embodiment of Formula I, A, X, and $R_1$ are as defined, as applicable, in any of (a1)-(b8), and $R_A$ is as defined as (II-3).

(c4) In one embodiment of Formula I, A, X, and $R_1$ are as defined, as applicable, in any of (a1)-(b8), and $R_A$ is as defined as (II-4).

(c5) In one embodiment of Formula I, A, X, and $R_1$ are as defined, as applicable, in any of (a1)-(b8), and $R_A$ is as defined as (II-5).

(c6) In one embodiment of Formula I, A, X, and $R_1$ are as defined, as applicable, in any of (a1)-(b8), and $R_A$ is as defined as (II-6).

(d1) In one embodiment of Formula I, A, X, $R_1$, and $R_A$ are as defined, as applicable, in any of (a1)-(c6), and m is as defined in (V-1).

(d2) In one embodiment of Formula I, A, X, $R_1$, and $R_A$ are as defined, as applicable, in any of (a1)-(c6), and m is as defined in (V-2).

(d3) In one embodiment of Formula I, A, X, $R_1$, and $R_A$ are as defined, as applicable, in any of (a1)-(c6), and m is as defined in (V-3).

(e1) In one embodiment of Formula I, A, X, $R_1$, $R_A$, and m are as defined, as applicable, in any of (a1)-(d3), and $R_2$ is as defined in (VI-1).

(e2) In one embodiment of Formula I, A, X, $R_1$, $R_A$, and m are as defined, as applicable, in any of (a1)-(d3), and $R_2$ is as defined in (VI-2).

(e3) In one embodiment of Formula I, A, X, $R_1$, $R_A$, and m are as defined, as applicable, in any of (a1)-(d3), and $R_2$ is as defined in (VI-3).

(e4) In one embodiment of Formula I, A, X, $R_1$, $R_A$, and m are as defined, as applicable, in any of (a1)-(d3), and $R_2$ is as defined in (VI-4).

(e5) In one embodiment of Formula I, A, X, $R_1$, $R_A$, and m are as defined, as applicable, in any of (a1)-(d3), and $R_2$ is as defined in (VI-5).

(e6) In one embodiment of Formula I, A, X, $R_1$, $R_A$, and m are as defined, as applicable, in any of (a1)-(d3), and $R_2$ is as defined in (VI-6).

(e7) In one embodiment of Formula I, A, X, $R_1$, $R_A$, and m are as defined, as applicable, in any of (a1)-(d3), and $R_2$ is as defined in (VI-7).

(f1) In one embodiment of Formula I, A, X, $R_1$, $R_A$, m, and $R_2$ are as defined, as applicable, in any of (a1)-(e7), and n is as defined in (VII-1).

(f2) In one embodiment of Formula I, A, X, $R_1$, $R_A$, m, and $R_2$ are as defined, as applicable, in any of (a1)-(e7), and n is as defined in (VII-2).

(f3) In one embodiment of Formula I, A, X, $R_1$, $R_A$, m, and $R_2$ are as defined, as applicable, in any of (a1)-(e7), and n is as defined in (VII-3).

(f4) In one embodiment of Formula I, A, X, $R_1$, $R_A$, m, and $R_2$ are as defined, as applicable, in any of (a1)-(e7), and n is as defined in (VII-4).

(f5) In one embodiment of Formula I, A, X, $R_1$, $R_A$, m, and $R_2$ are as defined, as applicable, in any of (a1)-(e7), and n is as defined in (VII-5).

(g1) In one embodiment of Formula I, A, X, $R_1$, $R_A$, m, $R_2$, and n are as defined, as applicable, in any of (a1)-(f5), and $R_3$ is as defined in (VIII-1).

(g2) In one embodiment of Formula I, A, X, $R_1$, $R_A$, m, $R_2$, and n are as defined, as applicable, in any of (a1)-(f5), and $R_3$ is as defined in (VIII-2).

(g3) In one embodiment of Formula I, A, X, $R_1$, $R_A$, m, $R_2$, and n are as defined, as applicable, in any of (a1)-(f5), and $R_3$ is as defined in (VIII-3).

(g4) In one embodiment of Formula I, A, X, $R_1$, $R_A$, m, $R_2$, and n are as defined, as applicable, in any of (a1)-(f5), and $R_3$ is as defined in (VIII-4).

(g5) In one embodiment of Formula I, A, X, $R_1$, $R_A$, m, $R_2$, and n are as defined, as applicable, in any of (a1)-(f5), and $R_3$ is as defined in (VIII-5).

(g6) In one embodiment of Formula I, A, X, $R_1$, $R_A$, m, $R_2$, and n are as defined, as applicable, in any of (a1)-(f5), and $R_3$ is as defined in (VIII-6).

(h1) In one embodiment of Formula I, A, X, $R_1$, $R_A$, m, $R_2$, n, and $R_3$ are as defined, as applicable, in any of (a1)-(g6), and $R_4$ is as defined in (IX-1).

(h2) In one embodiment of Formula I, A, X, $R_1$, $R_A$, m, $R_2$, n, and $R_3$ are as defined, as applicable, in any of (a1)-(g6), and $R_4$ is as defined in (IX-2).

(h3) In one embodiment of Formula I, A, X, $R_1$, $R_A$, m, $R_2$, n, and $R_3$ are as defined, as applicable, in any of (a1)(g6), and $R_4$ is as defined in (IX-3).

(h4) In one embodiment of Formula I, A, X, $R_1$, $R_A$, m, $R_2$, n, and $R_3$ are as defined, as applicable, in any of (a1)-(g6), and $R_4$ is as defined in (IX-4).

(i1) In one embodiment of Formula I, A, X, $R_1$, $R_A$, m, $R_2$, n, $R_3$, and $R_4$ areas defined, as applicable, in any of (a1)-(h4), and $R_5$ is as defined in (X-1).

(i2) In one embodiment of Formula I, A, X, $R_1$, $R_A$, m, $R_2$, n, $R_3$, and $R_4$ are as defined, as applicable, in any of (a1)-(h4), and $R_5$ is as defined in (X-2).

(i3) In one embodiment of Formula I, A, X, $R_1$, $R_A$, n, $R_2$, n, $R_3$, and $R_4$ are as defined, as applicable, in any of (a1)-(h4), and $R_5$ is as defined in (X-3).

(i4) In one embodiment of Formula I, A, X, $R_1$, $R_A$, m, $R_2$, n, $R_3$, and $R_4$ are as defined, as applicable, in any of (a1)-(h4), and $R_5$ is as defined in (X-4).

(j1) In one embodiment of Formula I, A, X, $R_1$, $R_A$, m, $R_2$, n, $R_3$, $R_4$, and $R_5$ are as defined, as applicable, in any of (a1)-(i4), and $R_x$ is as defined in (XI-1).

(j2) In one embodiment of Formula I, A, X, $R_1$, $R_A$, m, $R_2$, n, $R_3$, $R_4$, and $R_5$ are as defined, as applicable, in any of (a1)-(i4), and $R_x$ is as defined in (XI-2).

(k1) In one embodiment of Formula I, A, X, $R_1$, $R_A$, m, $R_2$, n, $R_3$, $R_4$, $R_5$, and $R_x$ are as defined, as applicable, in any of (a1)-(j2), and $R_B'$ is as defined in (XII-1).

(k2) In one embodiment of Formula I, A, X, $R_1$, $R_A$, m, $R_2$, n, $R_3$, $R_4$, $R_5$, and $R_x$ are as defined, as applicable, in any of (a1)-(j2), and $R_B'$ is as defined in (XII-2).

(k3) In one embodiment of Formula I, A, X, $R_1$, $R_A$, m, $R_2$, n, $R_3$, $R_4$, $R_5$, and $R_x$ are as defined, as applicable, in any of (a1)-(j2), and $R_B'$ is as defined in (XII-3).

(k4) In one embodiment of Formula I, A, X, $R_1$, $R_A$, m, $R_2$, n, $R_3$. $R_4$, $R_5$, and $R_A$ are as defined, as applicable, in any of (a1)-(j2), and $R_B'$ is as defined in (XII-4).

(l1) In one embodiment of Formula I, A, X, $R_1$, $R_A$, m, $R_2$, n, $R_3$, $R_4$, $R_5$, $R_x$, and $R_B'$ are as defined, as applicable, in any of (a1)-(k4), and $R_B$ is as defined in (XIII-1).

(l2) In one embodiment of Formula I, A, X, $R_1$, $R_A$, m, $R_2$, n, $R_3$, $R_4$, $R_5$, $R_x$, and $R_B'$ are as defined, as applicable, in any of (a1)-(k4), and $R_B$ is as defined in (XIII-2).

(l3) In one embodiment of Formula I, A, X, $R_1$, $R_A$, m, $R_2$, n, $R_3$, $R_4$, $R_5$, $R_x$, and $R_B'$ are as defined, as applicable, in any of (a1)-(k4), and $R_B$ is as defined in (XIII-3).

In one embodiment, the compound of Formula I is of Formula Ia or Ib:

(Ia)

(Ib)

or a pharmaceutically acceptable salt or solvate thereof.

For a compound of Formula Ia or Ib, A, $R_4$, $R_1$, m, $R_2$, n, $R_3$, $R_4$, $R_5$, $R_x$, $R_B'$, and $R_B$ can each be selected from any of the substituents for any of A, $R_4$, $R_1$, m, $R_2$, n, $R_3$, $R_4$, $R_5$, $R_x$, $R_B'$, and $R_B$ as described herein, for example, in Formula I, and can be combined with any of the substituents described herein for one or more of the remainder of A, $R_4$, $R_1$, m, $R_2$, n, $R_3$, $R_4$, $R_5$, $R_x$, $R_B'$, and $R_B$ as descried herein.

In one embodiment, the compound of Formula I is of any one of Formulae Iaa1-Iaa3 and Iba1-Iba3:

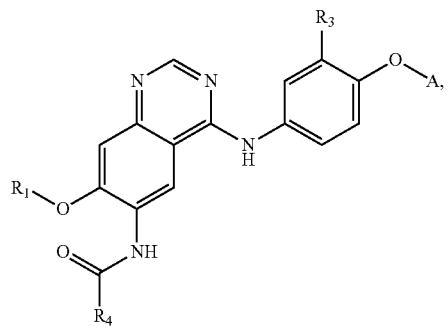

(Iaa1)

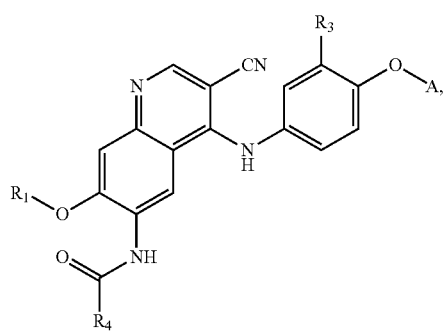

(Iba1)

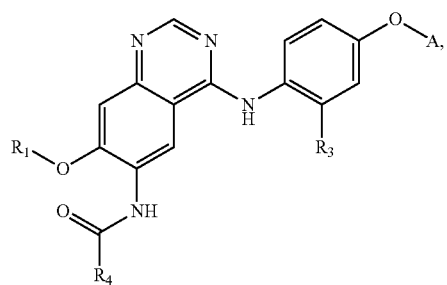

(Iaa2)

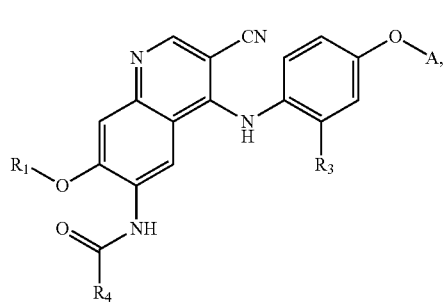

(Iba2)

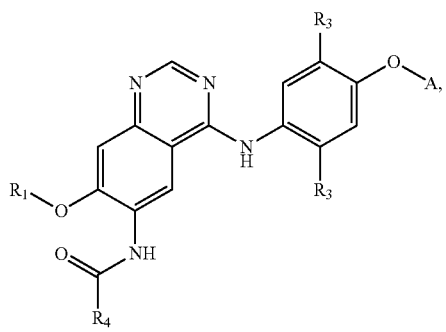

(Iaa3)

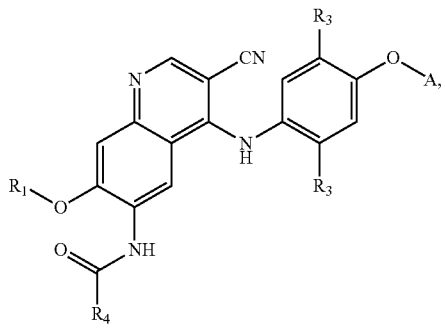

(Iba3)

or a pharmaceutically acceptable salt or solvate thereof.

For a compound of any one of Formulae Iaa1-Iaa3 and Iba1-Iba3, A, $R_4$, $R_1$, $R_3$, $R_4$, $R_x$, $R_B'$, and $R_B$ can each be selected from any of the substituents for any of A, $R_4$, $R_1$, $R_3$, $R_4$, $R_x$, $R_B'$, and $R_B$ as described herein, for example, in Formula I, and can be combined with any of the substituents described herein for one or more of the remainder of A, $R_4$, $R_1$, $R_3$, $R_4$, $R_x$, $R_B'$, and $R_B$ as descried herein.

In one embodiment, the compound of Formula I is of any one of Formulae Iab1-Iab10 and Ibb1-Ibb10:

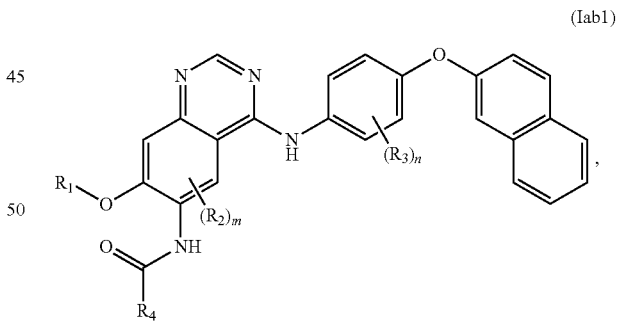

(Iab1)

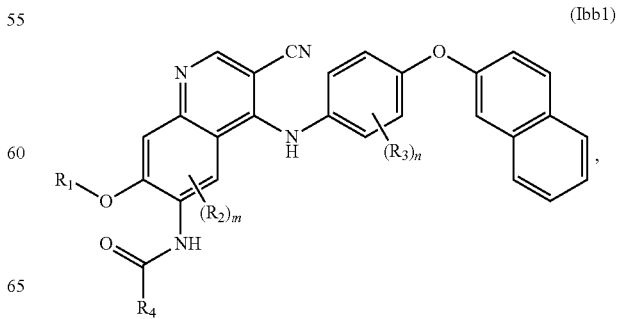

(Ibb1)

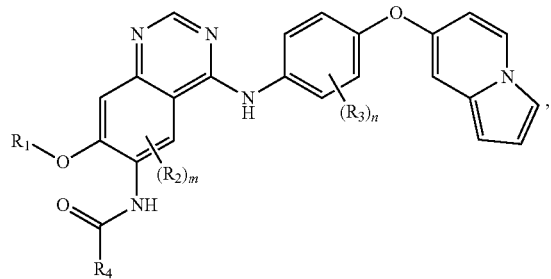
(Iab2)
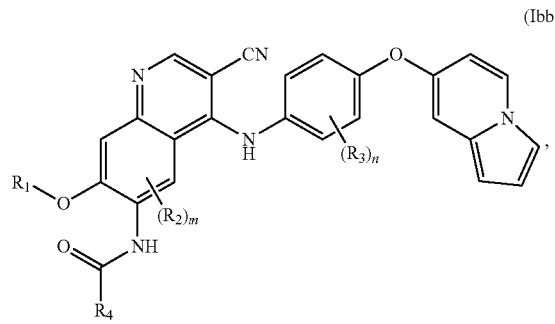
(Ibb2)
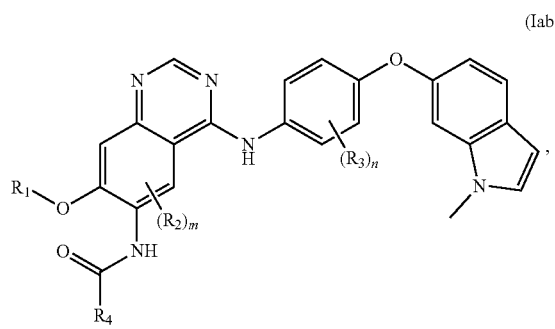
(Iab3)
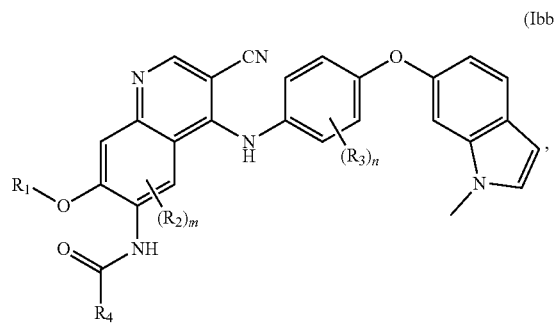
(Ibb3)
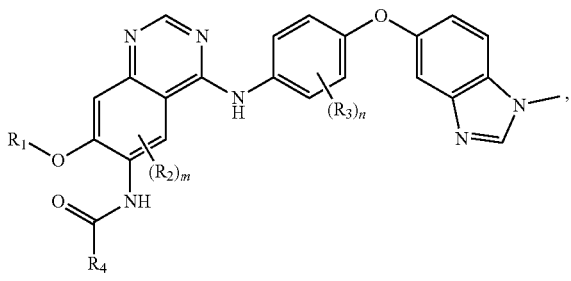
(Iab4)
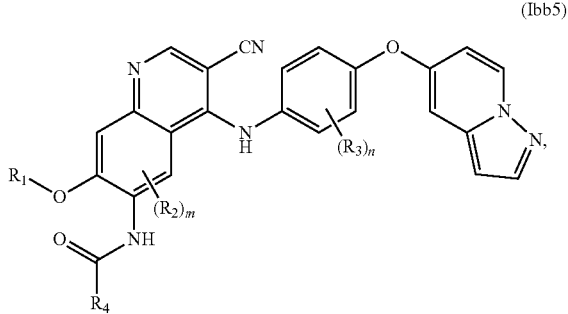
(Ibb4)
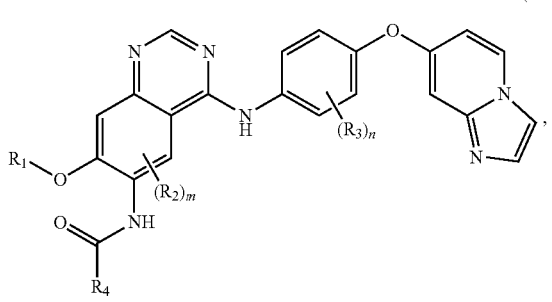
(Iab5)
(Ibb5)
(Iab6)
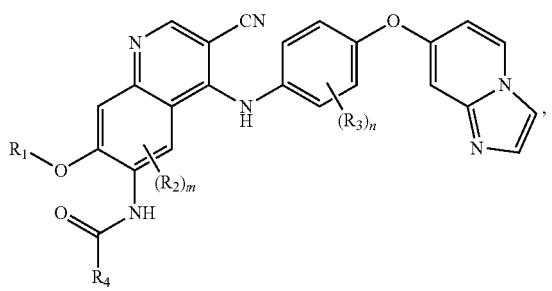
(Ibb6)

-continued

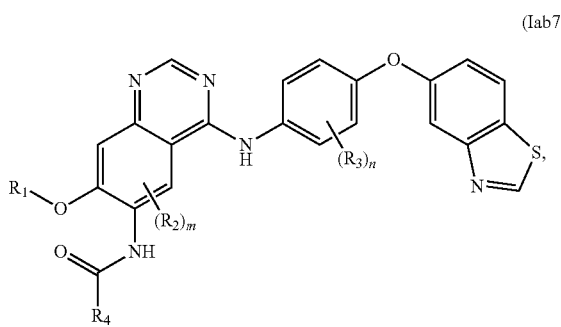
(Iab7)

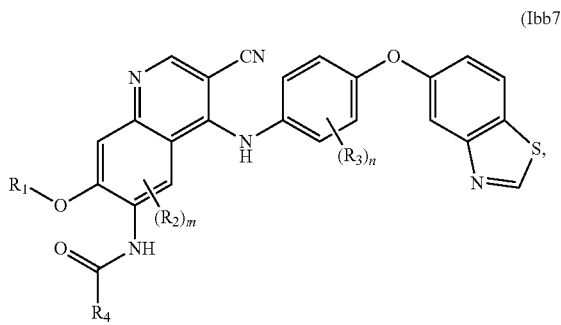
(Ibb7)

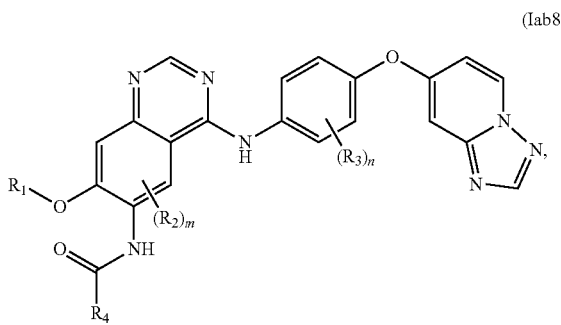
(Iab8)

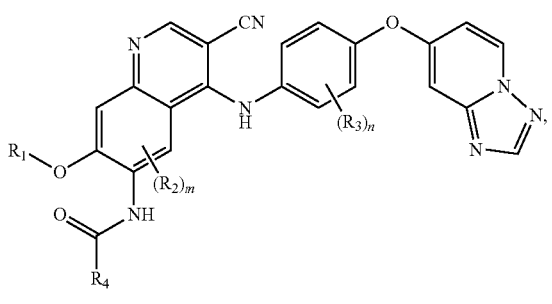
(Ibb8)

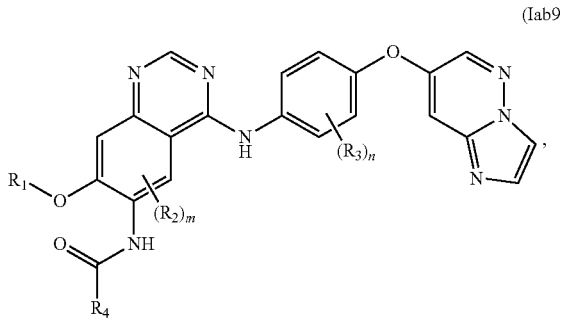
(Iab9)

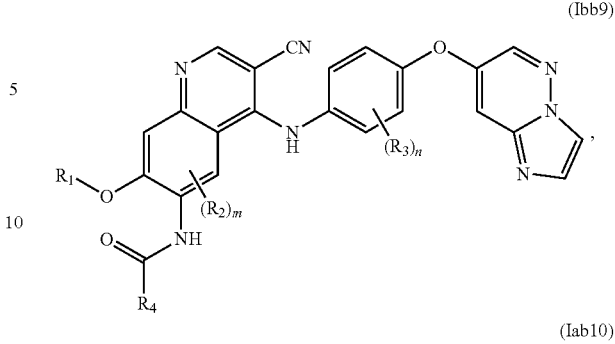
(Ibb9)

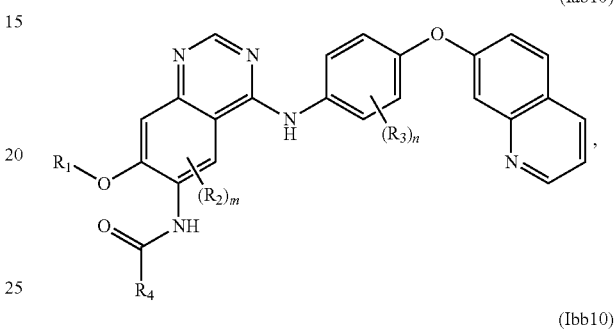
(Iab10)

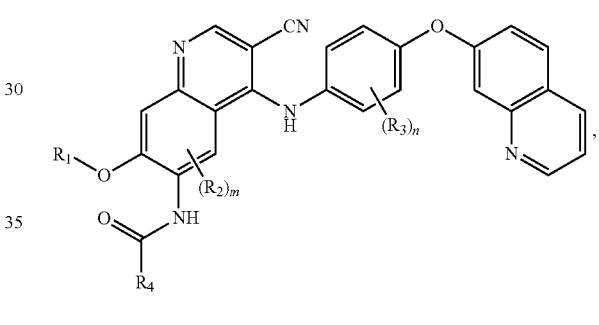
(Ibb10)

or a pharmaceutically acceptable salt or solvate thereof.

For a compound of any one of Formulae Iab1-Iab10 and Ibb1-Ibb10, $R_1$, m, $R_2$, n, $R_3$, $R_4$, $R_5$, $R_x$, $R_B'$, and $R_B$ can each be selected from any of the substituents for any of $R_1$, m, $R_2$, n, $R_3$, $R_4$, $R_5$, $R_x$, $R_B'$, and $R_B$ as described herein, for example, in Formula I, and can be combined with any of the substituents described herein for one or more of the remainder of $R_1$, m, $R_2$, n, $R_3$, $R_4$, $R_5$, $R_x$, $R_B'$, and $R_B$ as descried herein.

In one embodiment of any one of Formulae Iab1-Iab10 and Ibb1-Ibb10, $R_1$ is $C_1$-$C_6$ alkyl (e.g., methyl, ethyl, n-propyl, i-propyl, n-butyl, i-butyl, s-butyl, t-butyl, pentyl, or hexyl), wherein the alkyl is optionally substituted with one or more $R_B'$. In one embodiment, $R_1$ is methyl optionally substituted with one or more $R_B'$. In one embodiment, $R_1$ is ethyl optionally substituted with one or more $R_B'$. In one embodiment, $R_1$ is propyl optionally substituted with one or more $R_B'$. In one embodiment, $R_1$ is butyl optionally substituted with one or more $R_B'$. In one embodiment, $R_1$ is pentyl optionally substituted with one or more $R_B'$. In one embodiment, $R_1$ is hexyl optionally substituted with one or more $R_B'$.

In one embodiment of any one of Formulae Iab1-Iab10 and Ibb1-Ibb10, $R_1$ is $(CH_2)_{1-3}$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_2$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_3$-heterocyclyl comprising one 5- or 6-membered ring and 1-3 heteroatoms selected N and O and at least one N, wherein the heterocyclyl is optionally substituted with one or more $R_B$. In one embodiment, the heterocyclyl comprises one 5-membered ring. In one embodiment, the heterocyclyl comprises one 6-membered ring. In one embodiment, the heterocyclyl comprises one N. In one embodiment, the heterocyclyl comprises one N and one O. In one embodiment, the heterocyclyl comprises two N. In one embodiment, the heterocyclyl comprises one N and two O. In one embodiment, the heterocyclyl comprises two N and one O. In one embodiment, the heterocyclyl comprises three N. In one embodiment, the heterocyclyl is

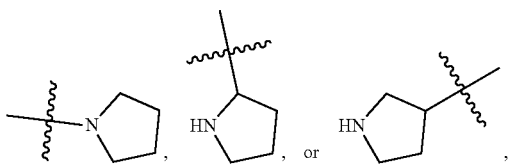

and is optionally substituted with one or more $R_B$. In one embodiment, the heterocyclyl is

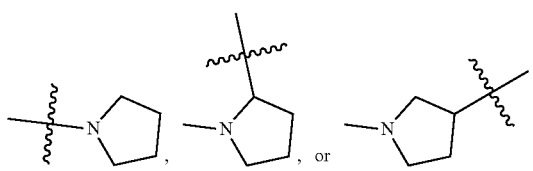

In one embodiment, the heterocyclyl is

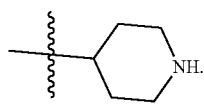

In one embodiment, the heterocyclyl is

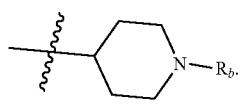

In one embodiment, the heterocyclyl is

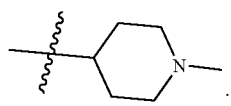 [SMILES: *C1CCN(C)CC1]

In one embodiment of any one of Formulae Iab1-Iab10 and Ibb1-Ibb10, $R_4$ is $C_2$-$C_4$ alkenyl (e.g., ethenyl, propenyl, or butenyl) optionally substituted with one or more $R_x$.

In one embodiment of any one of Formulae Iab1-Iab10 and Ibb1-Ibb10, $R_4$ is ethenyl optionally substituted with one or more $R_x$. In one embodiment, $R_4$ is ethenyl.

In one embodiment of any one of Formulae Iab1-Iab10 and Ibb1-Ibb10, $R_4$ is propenyl optionally substituted with one or more $R_x$. In one embodiment $R_4$ is 1-propenyl optionally substituted with one or more $R_x$. In one embodiment, $R_4$ is

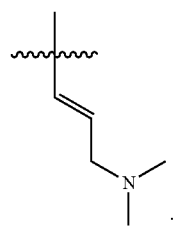 [SMILES: */C=C/CN(C)C]

In one embodiment, $R_4$ is 1-propenyl. In one embodiment, $R_4$ is 2-propenyl optionally substituted with one or more $R_x$. In one embodiment, $R_4$ is 2-propenyl.

In one embodiment of any one of Formulae Iab1-Iab10 and Ibb1-Ibb10, $R_4$ is butenyl optionally substituted with one or more $R_x$. In one embodiment, $R_4$ is 1-butenyl optionally substituted with one or more $R_x$. In one embodiment, $R_4$ is 1-butenyl. In one embodiment, $R_4$ is 2-butenyl optionally substituted with one or more $R_x$. In one embodiment, $R_4$ is 2-butenyl. In one embodiment, $R_4$ is 3-butenyl optionally substituted with one or more $R_x$. In one embodiment, $R_4$ is 3-butenyl.

In one embodiment, the compound of Formula I is of any one of Formulae Iac1-Iac2 and Ibc1-Ibc2:

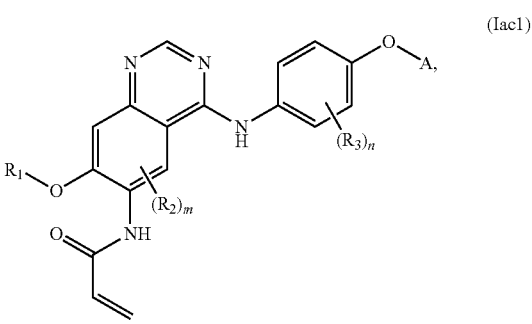

(Iac1)

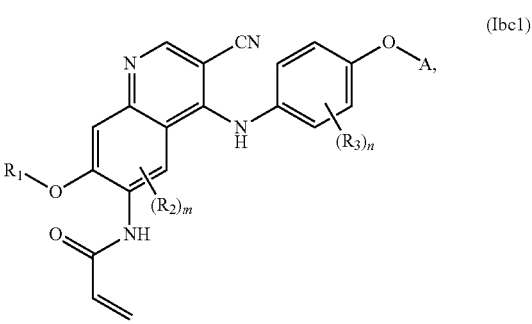

(Ibc1)

-continued

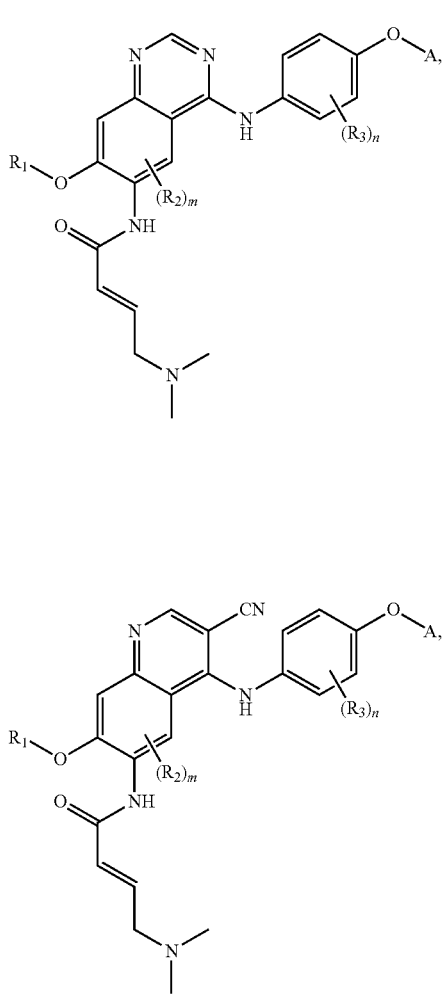

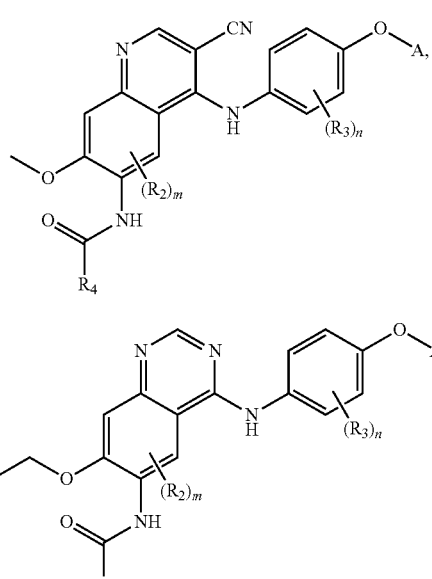

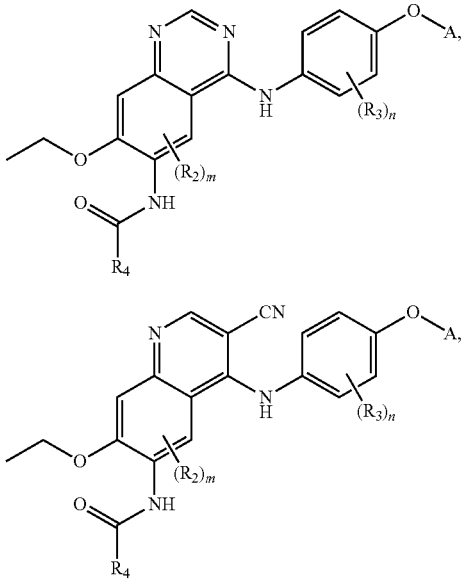

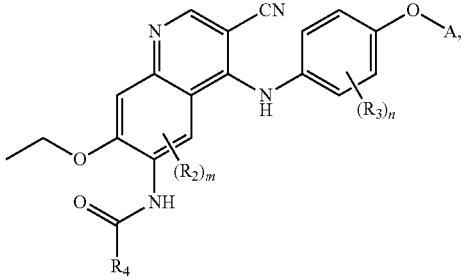

or a pharmaceutically acceptable salt or solvate thereof.

For a compound of any one of Formulae Iac1-Iac2 and Ibc1-Ibc2, A, $R_A$, $R_1$, m, $R_2$, n, $R_3$, $R_5$, $R_x$, $R_B'$, and $R_B$ can each be selected from any of the substituents for any of A, $R_A$, $R_1$, m, $R_2$, n, $R_3$, $R_5$, $R_x$, $R_B'$, and $R_B$ as described herein, for example, in Formula I, and can be combined with any of the substituents described herein for one or more of the remainder of A, $R_A$, $R_1$, m, $R_2$, n, $R_3$, $R_5$, $R_x$, $R_B'$, and $R_B$ as descried herein.

In one embodiment, the compound is of any one of Formulae Iad1-Iad4 and Ibd1-Ibd4:

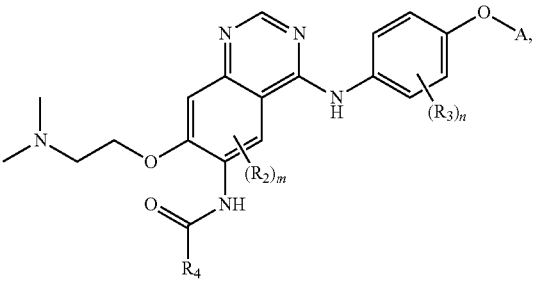

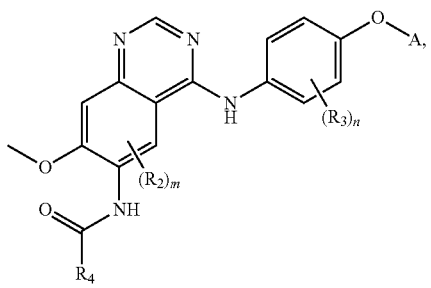

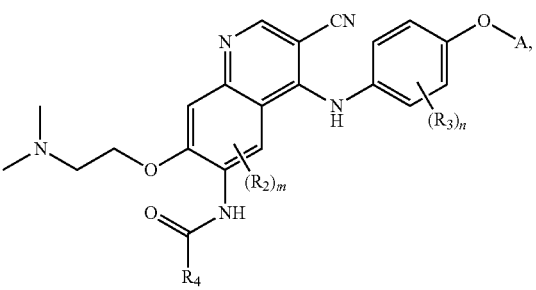

(Iad4)

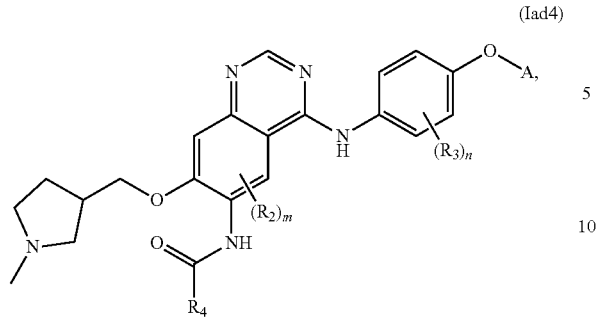

(Ibd4)

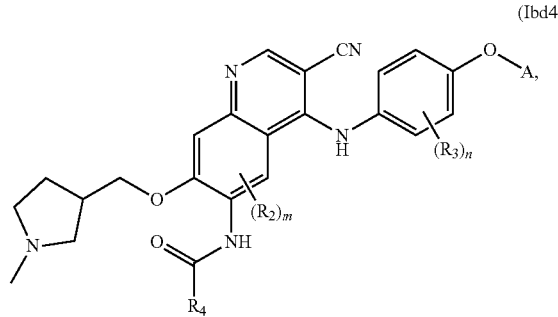

or a pharmaceutically acceptable salt or solvate thereof.

For a compound of any one of Formulae Iad1-Iad4 and Ibd1-Ibd4, A, $R_4$, m, $R_2$, n, $R_3$, $R_4$, $R_5$, and $R_x$ can each be selected from any of the substituents for any of A, $R_4$, m, $R_2$, n, $R_3$, $R_4$, $R_5$, and $R_x$ as described herein, for example, in Formula I. and can be combined with any of the substituents described herein for one or more of the remainder of A A, $R_4$, m, $R_2$, n, $R_3$, $R_4$, $R_5$, and $R_x$ as descried herein.

In one embodiment of any one of Formulae Iac1-Iac2, Ibc1-Ibc2, Iad1-Iad4, and Ibd1-Ibd4, A is naphthyl optionally substituted with one or more $R_4$. In one embodiment. A is naphthyl.

In one embodiment of any one of Formulae Iac1-Iac2, Ibc1-Ibc2, Iad1-Iad4, and Ibd1-Ibd4, A is bicyclic heteroaryl comprising two 5- or 6-membered rings and 1-4 heteroatoms selected from N, O, and S, and is optionally substituted with one or more $R_4$. In one embodiment, A is bicyclic heteroaryl comprising one 5-membered ring and one 6-membered ring. In one embodiment, A is bicyclic heteroaryl comprising two 6-membered rings. In one embodiment, A is bicyclic heteroaryl comprising two 5-membered rings. In one embodiment. A is bicyclic heteroaryl comprising 1 heteroatom. In one embodiment, A is bicyclic heteroaryl comprising 2 heteroatoms. In one embodiment, A is bicyclic heteroaryl comprising 3 heteroatoms. In one embodiment, A is bicyclic heteroaryl comprising 4 heteroatoms. In one embodiment, the heteroatoms are selected from N and O. In one embodiment, the heteroatoms are selected from N and S. In one embodiment, the heteroatoms are selected from O and S. In one embodiment, the heteroatoms are N.

In one embodiment of any one of Formulae Iac1-Iac2, Ibc1-Ibc2, Iad1-Iad4, and Ibd1-Ibd4, A is

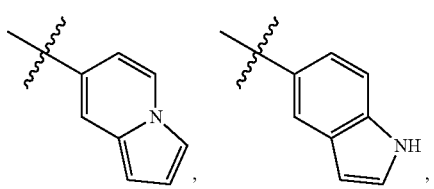

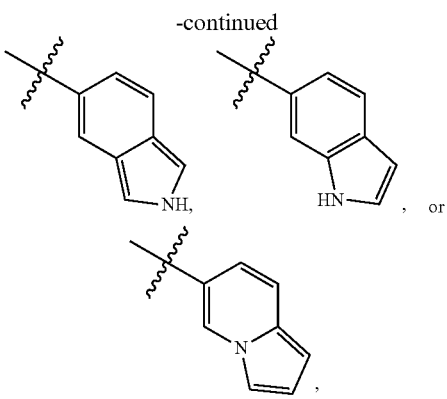

and is optionally substituted with one or more $R_4$. In one embodiment, A is

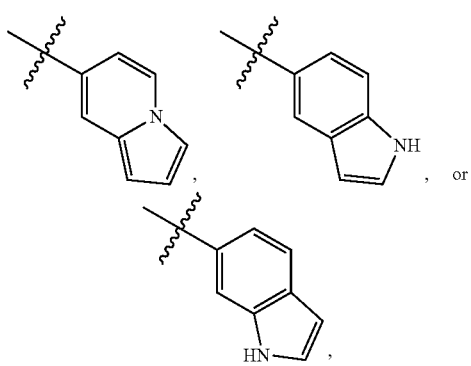

and is optionally substituted with one or more $R_4$. In one embodiment, A is

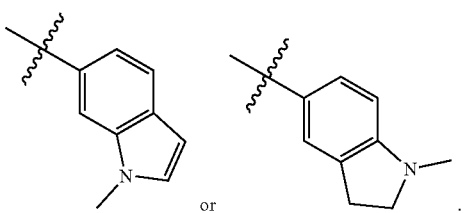 [SMILES: *c1ccc2ccn(C)c2c1 ; *c1ccc2c(c1)CCN2C]

In one embodiment of any one of Formulae Iac1-Iac2, Ibc1-Ibc2, Iad1-Iad4, and Ibd1-Ibd4, A is

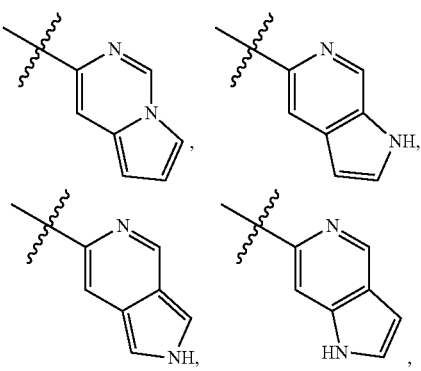

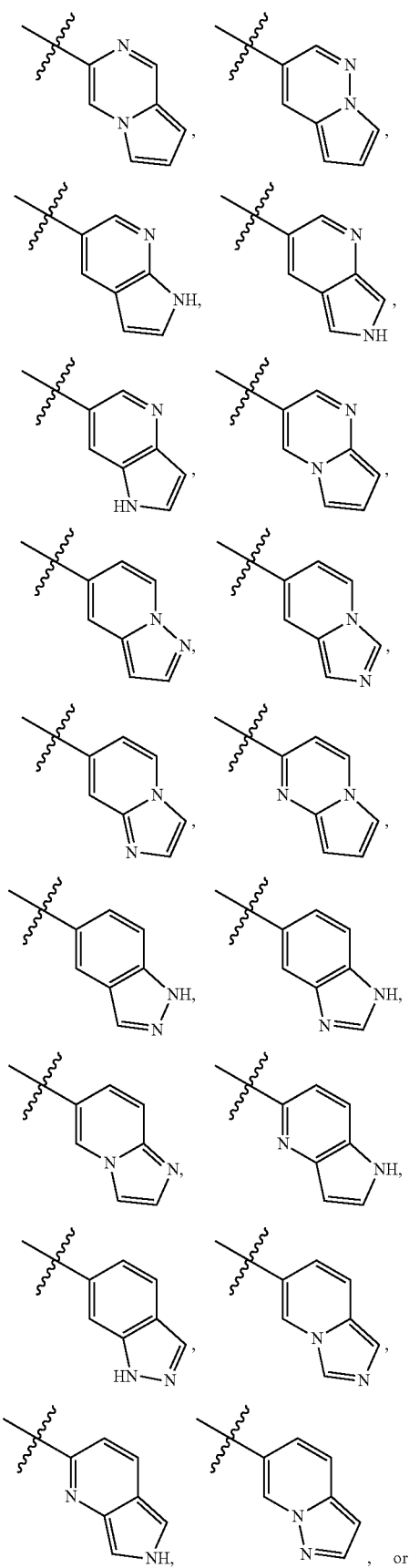
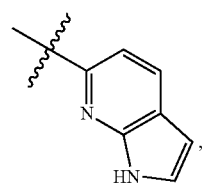
and is optionally substituted with one or more $R_A$. In one embodiment, A is
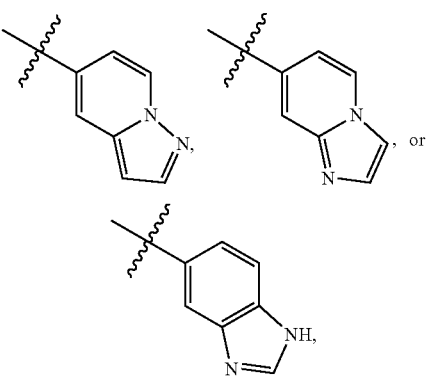
and is optionally substituted with one or more $R_A$.
In one embodiment of any one of Formulae Iac1-Iac2, Ibc1-Ibc2, Iad1-Iad4, and Ibd1-Ibd4, A is
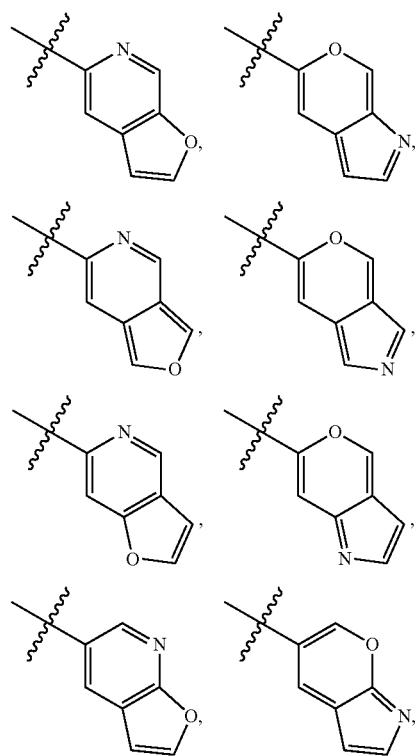

-continued
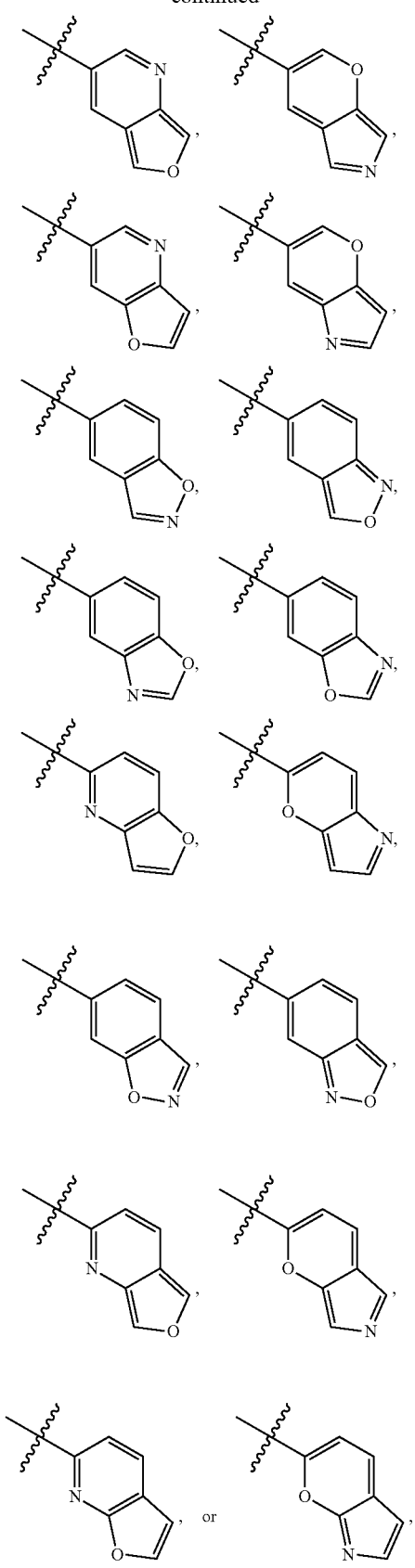
and is optionally substituted with one or more $R_A$.
In one embodiment of any one of Formulae Iac1-Iac2, Ibc1-Ibc2, Iad1-Iad4, and Ibd1-Ibd4, A is
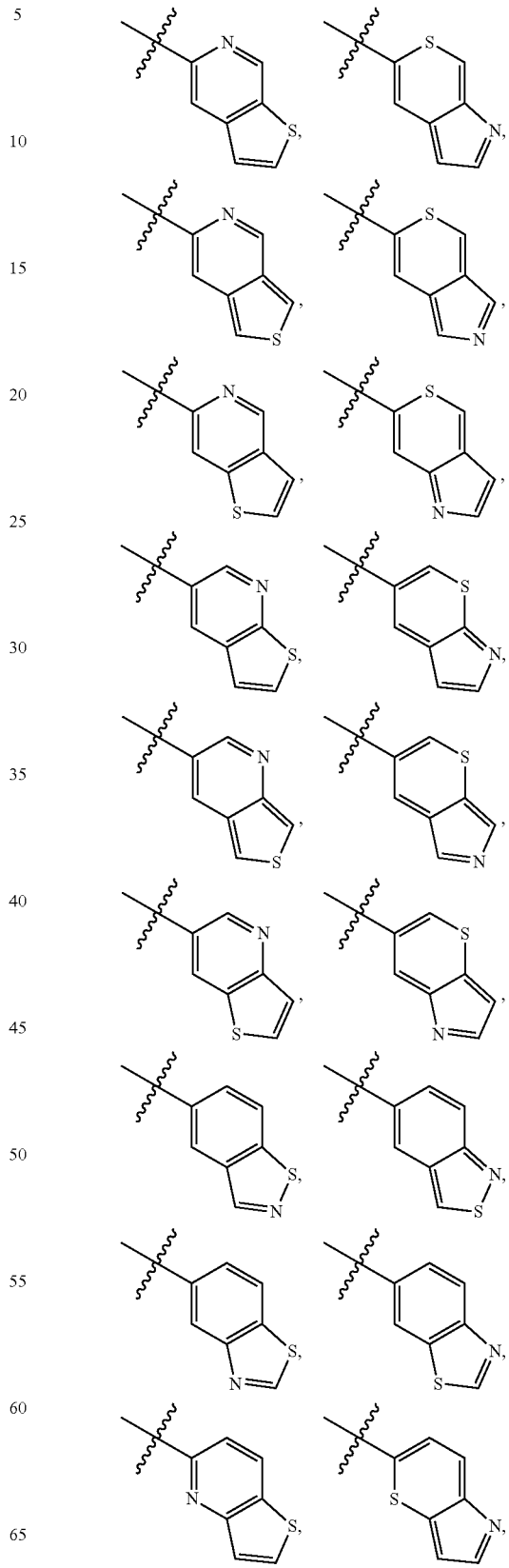

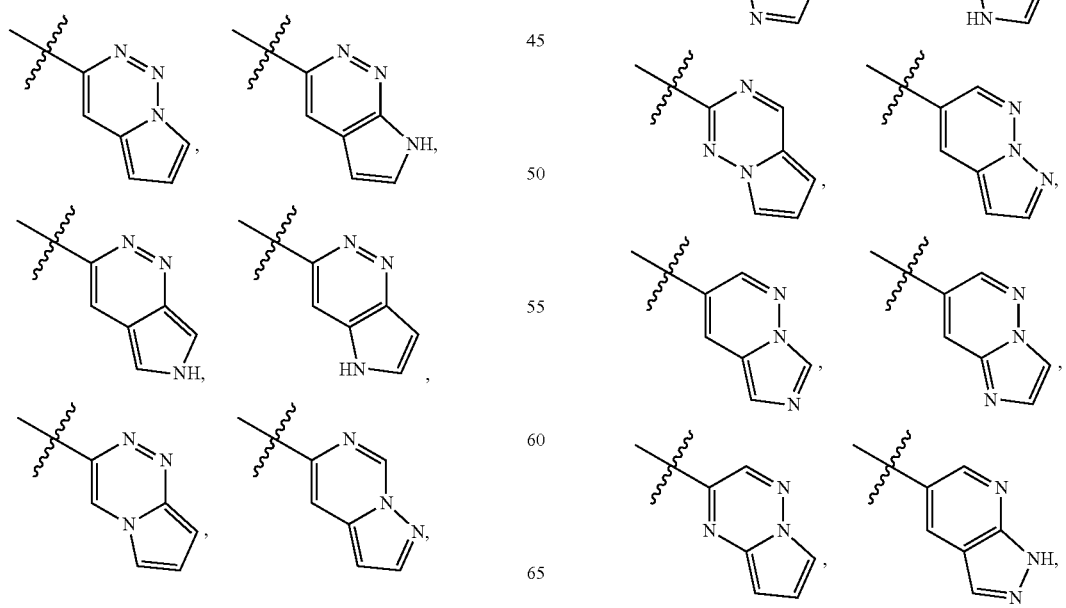
and is optionally substituted with one or more R_A. In one embodiment, A is
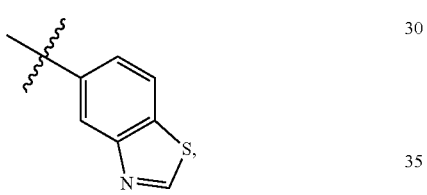
and is optionally substituted with one or more R_A.
In one embodiment of any one of Formulae Iac1-Iac2, Ibc1-Ibc2, Iad1-Iad4, and Ibd1-Ibd4, A is
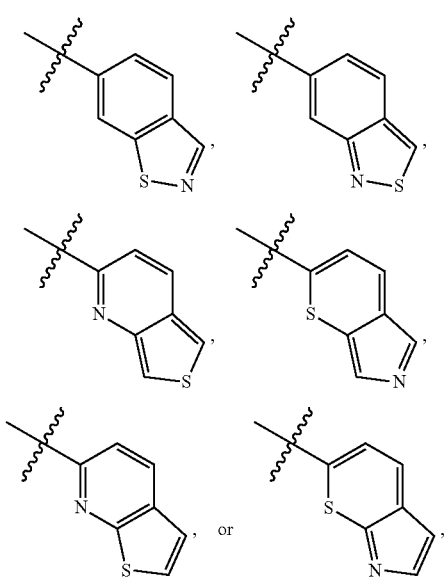 [SMILES: *c1ccc2cnoc2c1 ; *c1ccc2conc2c1 ; *c1ccc2cocc2n1 ; *c1ccc2cncc-2o1 ; *c1ccc2ccoc2n1 ; *c1ccc2ccnc-2o1]
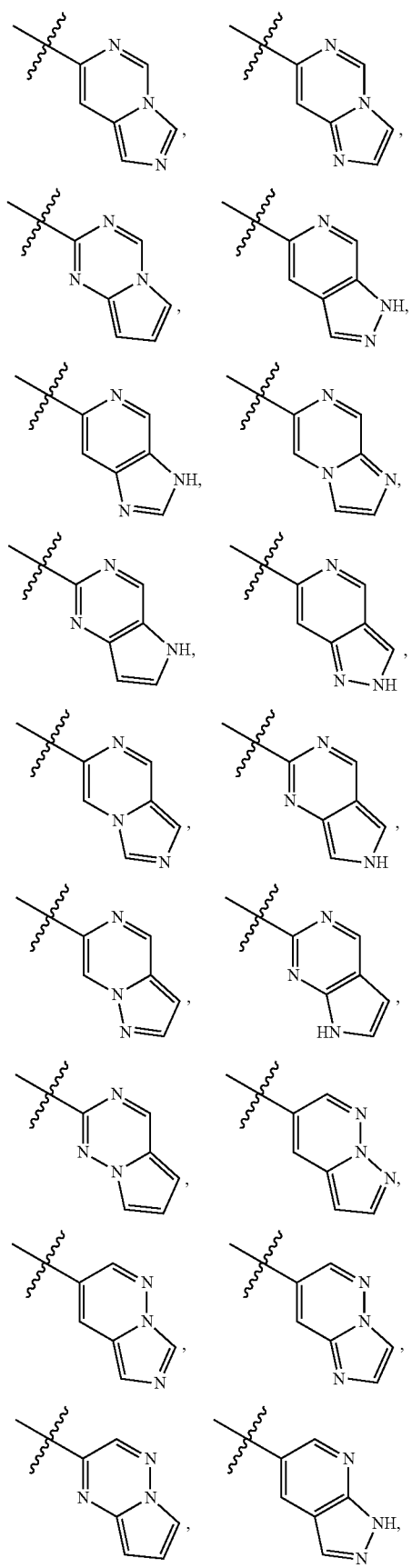

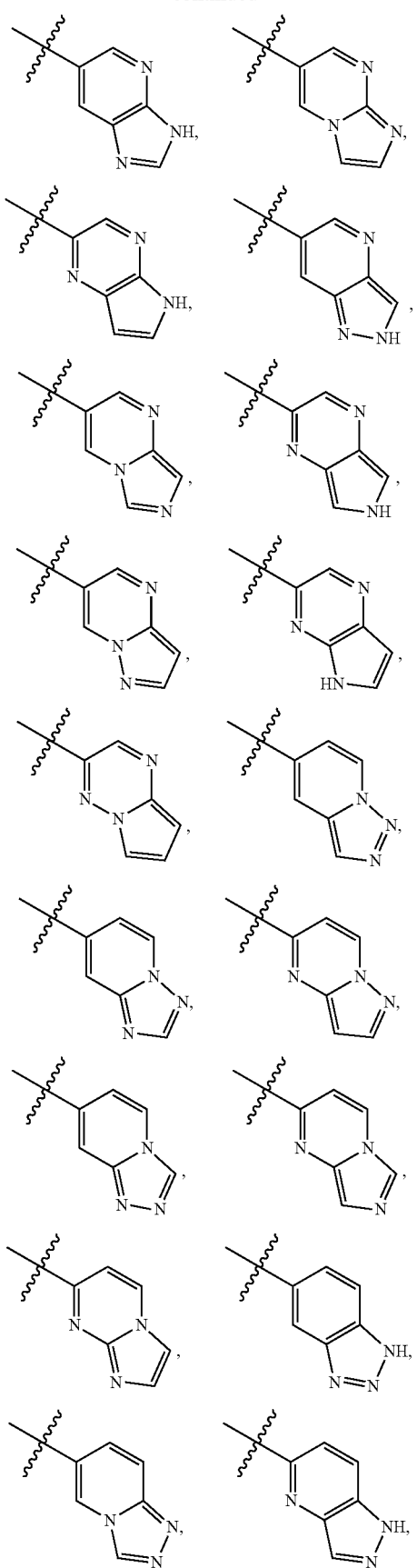
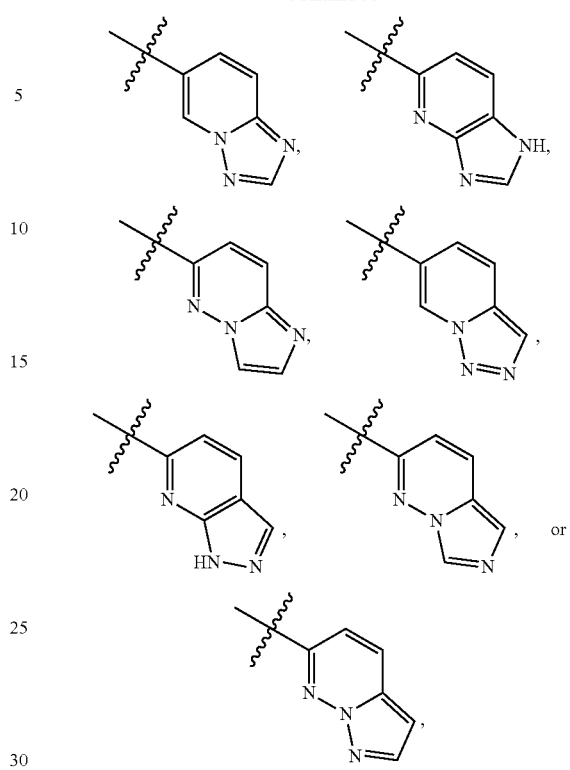
and is optionally substituted with one or more $R_A$. In one embodiment, A is
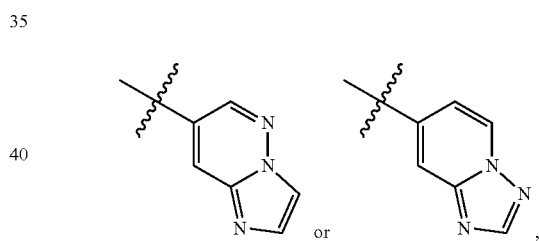
and is optionally substituted with one or more $R_A$.
In one embodiment of any one of Formulae Iac1-Iac2, Ibc1-Ibc2, Iad1-Iad4, and Ibd1-Ibd4, A is
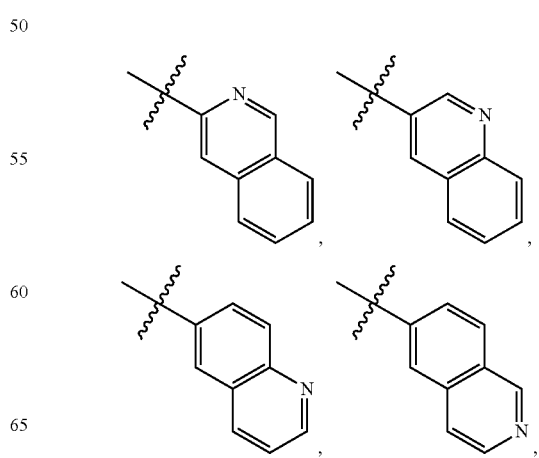

-continued

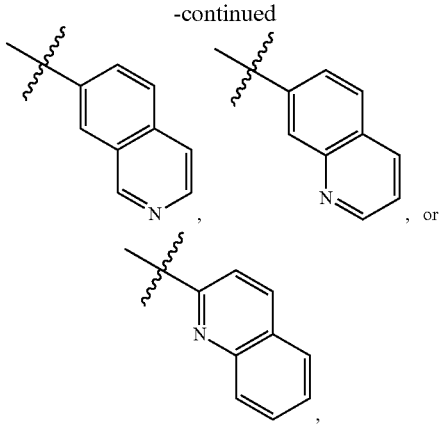

and is optionally substituted with one or more $R_A$. In one embodiment, A is

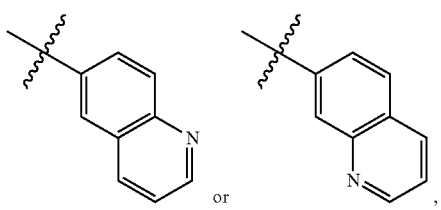 [SMILES: *c1ccc2ncccc2c1 ; *c1ccc2cccnc2c1]

and is optionally substituted with one or more $R_A$.

In one embodiment of any one of Formulae Iac1-Iac2 and Ibc1-Ibc2, $R_1$ is $C_1$-$C_6$ alkyl (e.g., methyl, ethyl, n-propyl, i-propyl, n-butyl, i-butyl, s-butyl, t-butyl, pentyl, or hexyl), wherein the alkyl is optionally substituted with one or more $R_B'$. In one embodiment, $R_1$ is methyl optionally substituted with one or more $R_B'$. In one embodiment, $R_1$ is ethyl optionally substituted with one or more $R_B'$. In one embodiment, $R_1$ is propyl optionally substituted with one or more $R_B'$. In one embodiment, $R_1$ is butyl optionally substituted with one or more $R_B'$. In one embodiment, $R_1$ is pentyl optionally substituted with one or more $R_B'$. In one embodiment, $R_1$ is hexyl optionally substituted with one or more $R_B'$.

In one embodiment of any one of Formulae Iac1-Iac2 and Ibc1-Ibc2, $R_1$ is $(CH_2)_{1-3}$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_2$-heterocyclyl comprising one 5- or 6-membered ring and 1-3 heteroatoms selected N and O and at least one N, wherein the heterocyclyl is optionally substituted with one or more $R_B$. In one embodiment, $R_1$ is $(CH_2)_3$-heterocyclyl comprising one 5- or 6-membered ring and 1-3 heteroatoms selected N and O and at least one N, wherein the heterocyclyl is optionally substituted with one or more $R_B$. In one embodiment, the heterocyclyl comprises one 5-membered ring. In one embodiment, the heterocyclyl comprises one 6-membered ring. In one embodiment, the heterocyclyl comprises one N. In one embodiment, the heterocyclyl comprises one N and one O. In one embodiment, the heterocyclyl comprises two N. In one embodiment, the heterocyclyl comprises one N and two O. In one embodiment, the heterocyclyl comprises two N and one O. In one embodiment, the heterocyclyl comprises three N. In one embodiment, the heterocyclyl is

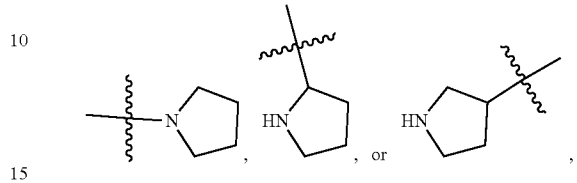

and is optionally substituted with one or more $R_B$. In one embodiment, the heterocyclyl is

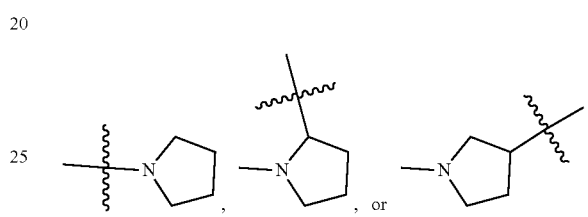

In one embodiment, the heterocyclyl is

In one embodiment, the heterocyclyl is

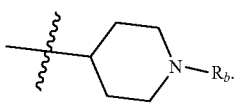

In one embodiment, the heterocyclyl is

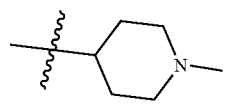

In one embodiment of any one of Formulae Iad1-Iad4 and Ibd1-Ibd4, $R_4$ is $C_2$-$C_4$ alkenyl (e.g., ethenyl, propenyl, or butenyl) optionally substituted with one or more $R_x$.

In one embodiment of any one of Formulae Iad1-Iad4 and Ibd1-Ibd4, $R_4$ is ethenyl optionally substituted with one or more $R_x$. In one embodiment, $R_4$ is ethenyl.

In one embodiment of any one of Formulae Iad1-Iad4 and Ibd1-Ibd4, $R_4$ is propenyl optionally substituted with one or more $R_x$. In one embodiment, $R_4$ is 1-propenyl optionally substituted with one or more $R_x$. In one embodiment, $R_4$ is

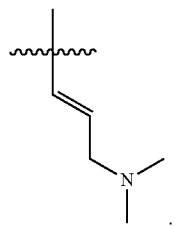 [SMILES: */C=C/CN(C)C]

In one embodiment, $R_4$ is 1-propenyl. In one embodiment, $R_4$ is 2-propenyl optionally substituted with one or more $R_x$. In one embodiment, $R_4$ is 2-propenyl.

In one embodiment of any one of Formulae Iad1-Iad4 and Ibd1-Ibd4, $R_4$ is butenyl optionally substituted with one or more $R_x$. In one embodiment, $R_4$ is 1-butenyl optionally substituted with one or more $R_x$. In one embodiment, $R_4$ is 1-butenyl. In one embodiment, $R_4$ is 2-butenyl optionally substituted with one or more $R_x$. In one embodiment, $R_4$ is 2-butenyl. In one embodiment, $R_4$ is 3-butenyl optionally substituted with one or more $R_x$. In one embodiment, $R_4$ is 3-butenyl.

Non-limiting illustrative compounds of the application are listed in Table 1.

TABLE 1

| Compound # | Structure |
|---|---|
| 1 | *(structure image)* |
| 2 | *(structure image)* |

TABLE 1-continued

| Compound # | Structure |
|---|---|
| 3 | 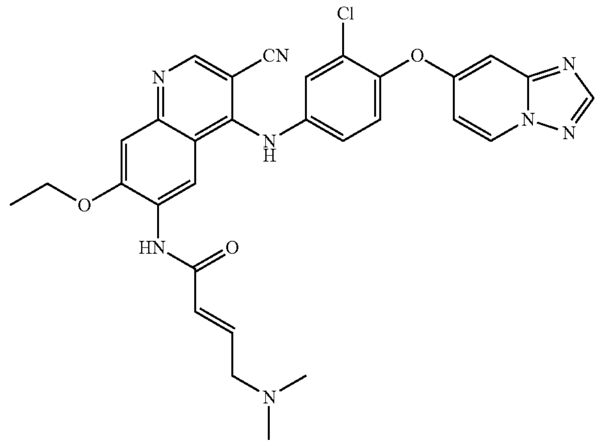 [SMILES: CCOc1cc2ncc(C#N)c(Nc3ccc(Oc4ccn5ncnc5c4)c(Cl)c3)c2cc1NC(=O)/C=C/CN(C)C] |
| 4 | 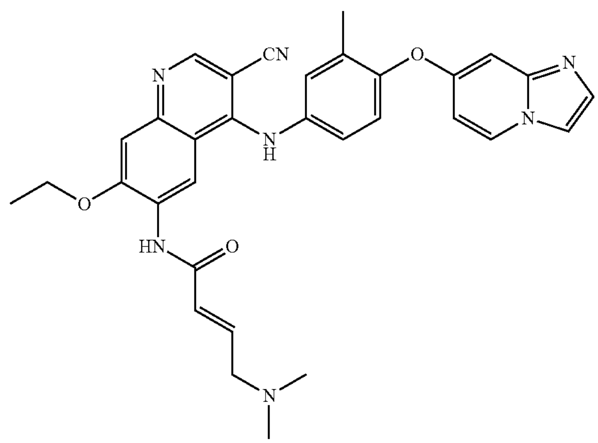 [SMILES: CCOc1cc2ncc(C#N)c(Nc3ccc(Oc4ccn5ccnc5c4)c(C)c3)c2cc1NC(=O)/C=C/CN(C)C] |
| 5 | 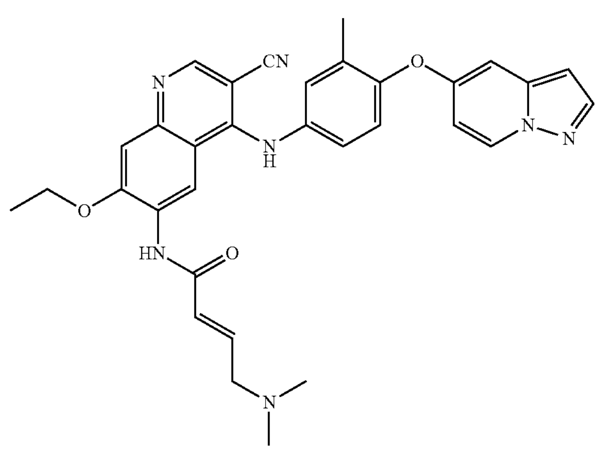 [SMILES: CCOc1cc2ncc(C#N)c(Nc3ccc(Oc4ccn5nccc5c4)c(C)c3)c2cc1NC(=O)/C=C/CN(C)C] |

TABLE 1-continued
| Compound # | Structure |
|---|---|
| 6 | 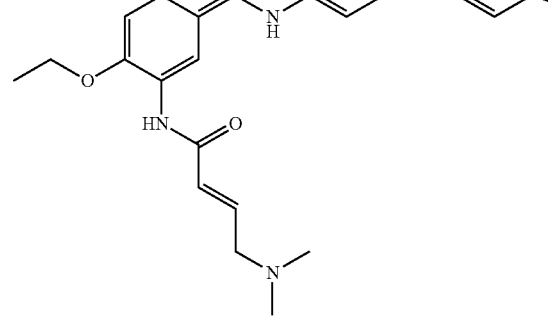 |
| 7 | 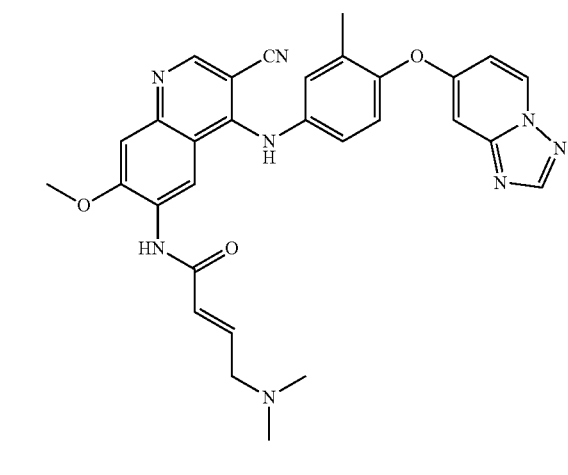 |
| 8 | 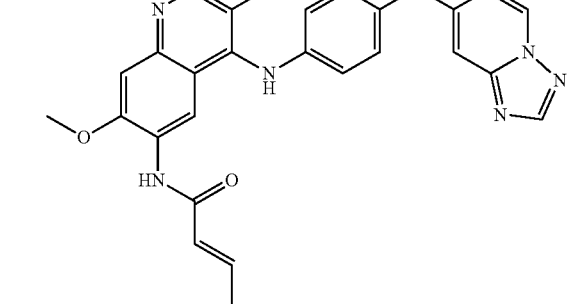 |

TABLE 1-continued
| Compound # | Structure |
|---|---|
| 9 | 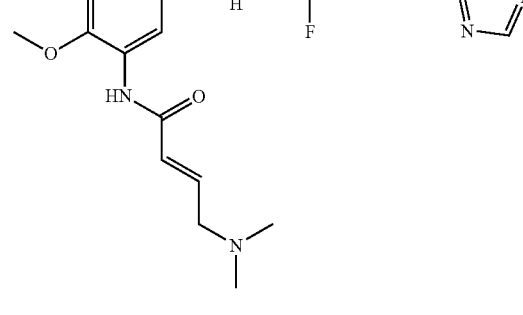 |
| 10 | 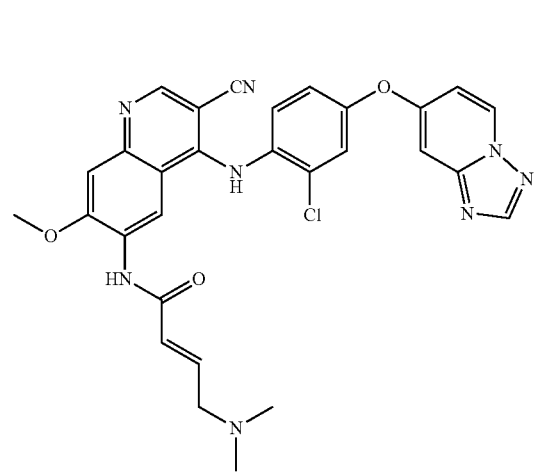 |
| 11 | 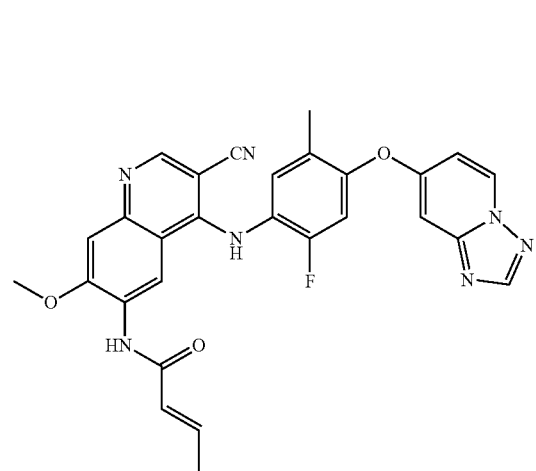 |

TABLE 1-continued
| Compound # | Structure |
|---|---|
| 12 | 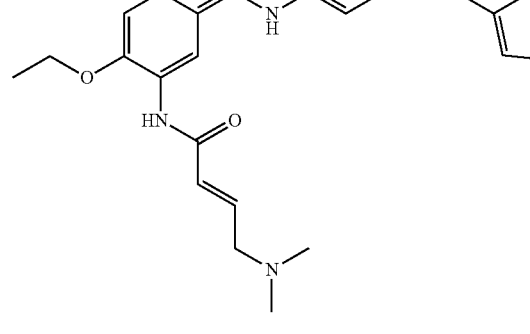 |
| 13 | 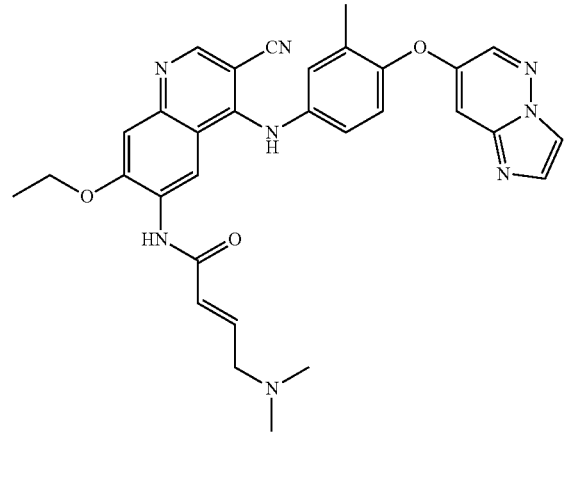 |
| 14 | 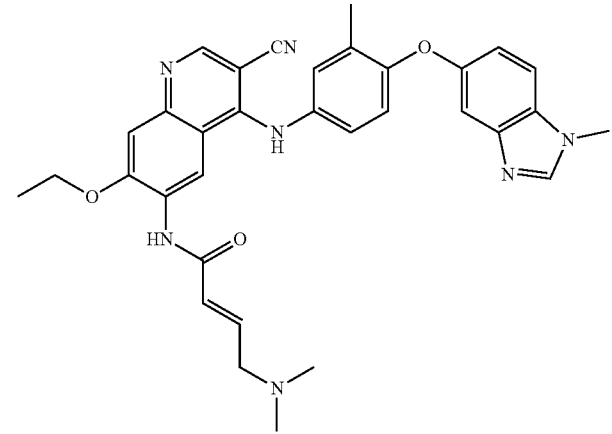 [SMILES: CCOc1cc2ncc(C#N)c(Nc3ccc(Oc4ccc5c(c4)ncn5C)c(C)c3)c2cc1NC(=O)/C=C/CN(C)C] |

TABLE 1-continued

| Compound # | Structure |
|---|---|
| 15 | 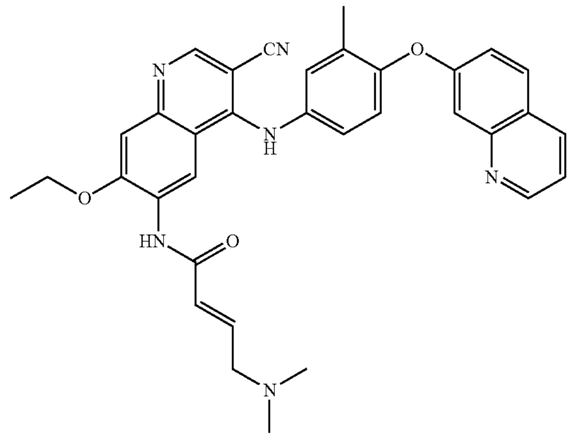 [SMILES: CCOc1cc2ncc(C#N)c(Nc3ccc(Oc4ccc5cccnc5c4)c(C)c3)c2cc1NC(=O)/C=C/CN(C)C] |
| 16 | 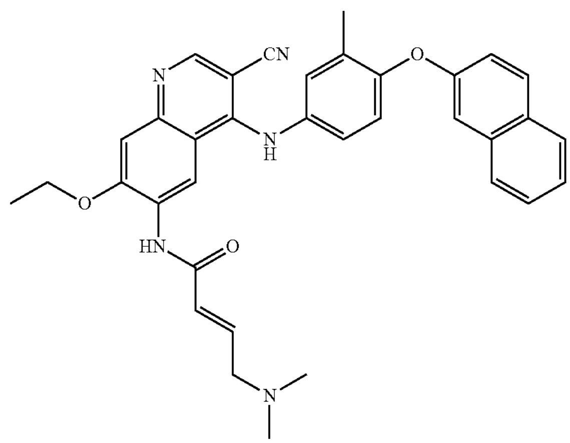 [SMILES: CCOc1cc2ncc(C#N)c(Nc3ccc(Oc4ccc5ccccc5c4)c(C)c3)c2cc1NC(=O)/C=C/CN(C)C] |
| 17 | 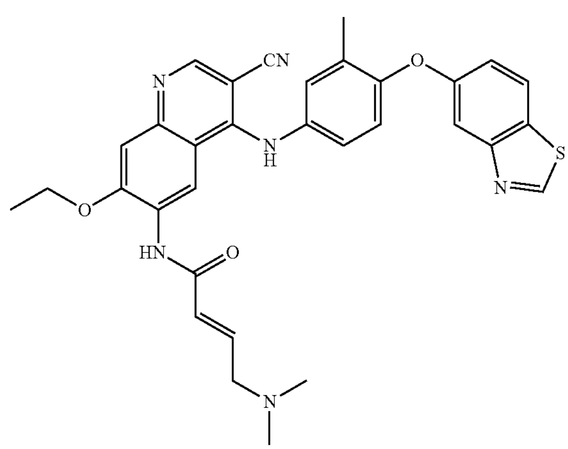 [SMILES: CCOc1cc2ncc(C#N)c(Nc3ccc(Oc4ccc5scnc5c4)c(C)c3)c2cc1NC(=O)/C=C/CN(C)C] |

TABLE 1-continued

| Compound # | Structure |
|---|---|
| 18 | 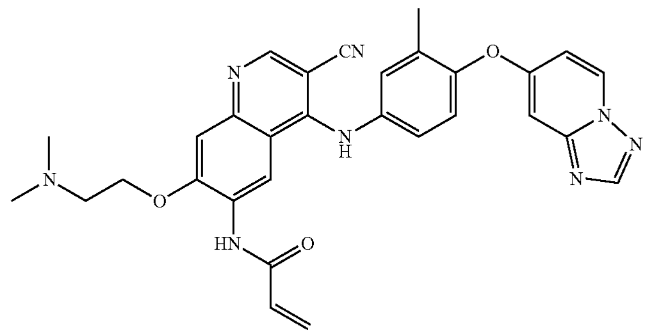 [SMILES: C=CC(=O)Nc1cc2c(Nc3ccc(Oc4ccn5ncnc5c4)c(C)c3)c(C#N)cnc2cc1OCCN(C)C] |
| 19 | 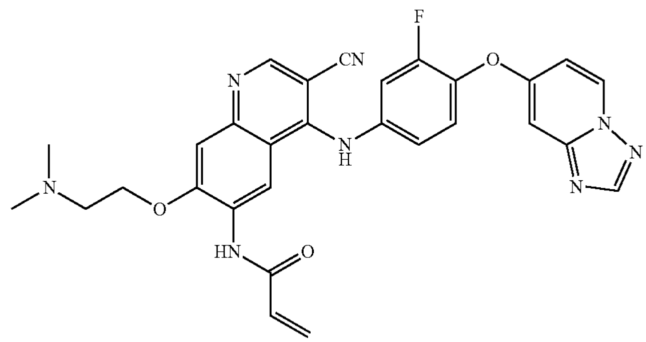 [SMILES: C=CC(=O)Nc1cc2c(Nc3ccc(Oc4ccn5ncnc5c4)c(F)c3)c(C#N)cnc2cc1OCCN(C)C] |
| 20 | 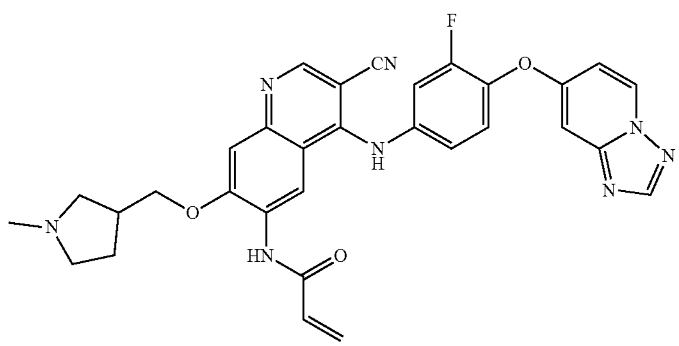 [SMILES: C=CC(=O)Nc1cc2c(Nc3ccc(Oc4ccn5ncnc5c4)c(F)c3)c(C#N)cnc2cc1OCC1CCN(C)C1] |
| 21 | 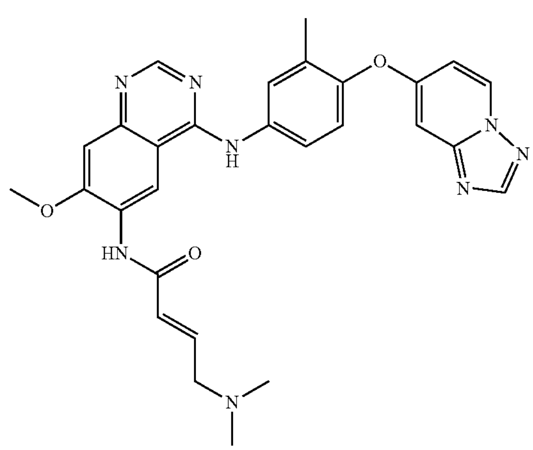 [SMILES: COc1cc2ncnc(Nc3ccc(Oc4ccn5ncnc5c4)c(C)c3)c2cc1NC(=O)/C=C/CN(C)C] |

TABLE 1-continued

| Compound # | Structure |
|---|---|
| 22 | (structure) |

In one aspect, the present disclosure provides compounds listed in Table 2 below and pharmaceutically acceptable salts and solvates thereof.

TABLE 2

| Compound # | Structure |
|---|---|
| 23 | (structure) |
| 24 | (structure) |

The compounds of the application may inhibit one or more receptors of the ErbB receptor tyrosine kinase family. For example, a compound of the present application may inhibit EGFR, HER2, HER3, and/or HER4, and/or any mutant thereof. In some embodiments, a compound of the present application inhibits EGFR. In some embodiments, a compound of the present application inhibits a mutant EGFR. In some embodiments, a compound of the present application inhibits HER2. In some embodiments, a compound of the present application inhibits a mutant HER2. In some embodiments, a compound of the present application inhibits EGFR and HER2 and/or a mutant thereof. In some embodiments, a compound of the present application selectively inhibits HER2 or a mutant thereof over EGFR or a mutant thereof.

In some embodiments, the compounds of the application are capable of modulating (e.g., inhibiting or decreasing) the activity of HER2 or a mutant thereof.

In some embodiments, the compounds of the present application are capable of modulating (e.g., inhibiting or decreasing) the activity of HER2 containing one or more mutations. In some embodiments, the mutant HER2 contains one or more mutations described herein. In some embodiments, the compounds of the present application are capable of modulating (e.g., inhibiting or decreasing) the activity of a wild-type HER2 and HER2 containing one or more mutations. In some embodiments, the compounds of the present application are capable of modulating (e.g., inhibiting or decreasing) the activity of HER2 containing one or more mutations, but do not affect the activity of a wild-type HER2.

In some embodiments, the compounds of the application exhibit at least 10% inhibition of HER2 containing one or more mutations as described herein relative to a wild-type HER2. In some embodiments, the compounds of the application exhibit at least 20% inhibition of HER2 containing one or more mutations as described herein relative to a wild-type HER2. In some embodiments, the compounds of the application exhibit at least 30% inhibition of HER2 containing one or more mutations as described herein relative to a wild-type HER2. In some embodiments, the compounds of the application exhibit at least 40% inhibition of HER2 containing one or more mutations as described herein relative to a wild-type HER2. In some embodiments, the compounds of the application exhibit at least 50% inhibition of HER2 containing one or more mutations as described herein relative to a wild-type HER2. In some embodiments, the compounds of the application exhibit at least 60% inhibition of HER2 containing one or more mutations as described herein relative to a wild-type HER2. In some embodiments, the compounds of the application exhibit at least 70% inhibition of HER2 containing one or more mutations as described herein relative to a wild-type HER2. In some embodiments, the compounds of the application exhibit at least 80% inhibition of HER2 containing one or more mutations as described herein relative to a wild-type HER2. In some embodiments, the compounds of the application exhibit at least 90% inhibition of HER2 containing one or more mutations as described herein relative to a wild-type HER2. In some embodiments, the compounds of the application exhibit at least 95% inhibition of HER2 containing one or more mutations as described herein relative to a wild-type HER2.

In some embodiments, the compounds of the application exhibit greater inhibition of HER2 containing one or more mutations as described herein relative to a wild-type HER2. In some embodiments, the compounds of the application exhibit at least 2-fold, 3-fold, 5-fold, 10-fold, 25-fold, 50-fold or 100-fold greater inhibition of HER2 containing one or more mutations as described herein relative to a wild-type HER2. In some embodiments, the compounds of the application exhibit up to 1000-fold greater inhibition of HER2 containing one or more mutations as described herein relative to a wild-type HER2.

In some embodiments, the compounds of the application exhibit from about 2-fold to about 10-fold greater inhibition of HER2 containing one or more mutations as described herein relative to a wild-type HER2. In some embodiments, the compounds of the application exhibit from about 10-fold to about 100-fold greater inhibition of HER2 containing one or more mutations as described herein relative to a wild-type HER2. In some embodiments, the compounds of the application exhibit from about 100-fold to about 1000-fold greater inhibition of HER2 containing one or more mutations as described herein relative to a wild-type HER2. In some embodiments, the compounds of the application exhibit from about 1000-fold to about 10000-fold greater inhibition of HER2 containing one or more mutations as described herein relative to a wild-type HER2.

In some embodiments, the compounds of the application is capable of binding to Cys805 in HER2 or a mutant thereof. In some embodiments, the compounds of the application is capable of forming a covalent bond with Cys805 in HER2 or a mutant thereof. In some embodiments, the compounds of the application binds to Cys805 in HER2 or a mutant thereof. In some embodiments, the compounds of the application forms a covalent bond with Cys805 in HER2 or a mutant thereof.

In some embodiments, the compounds of the application exhibit selective inhibition of HER2 over EGFR In some embodiments, the compounds of the application exhibit from about 2-fold to about 10-fold greater inhibition of HER2 relative to EGFR. In some embodiments, the compounds of the application exhibit from about 10-fold to about 100-fold greater inhibition of HER2 relative to EGFR. In some embodiments, the compounds of the application exhibit from about 100-fold to about 1000-fold greater inhibition of HER2 relative to EGFR In some embodiments, the compounds of the application exhibit from about 1000-fold to about 10000-fold greater inhibition of HER2 relative to EGFR.

In some embodiments, the compounds of the application exhibit selective inhibition of HER2 containing one or more mutations as described herein over EGFR. In some embodiments, the compounds of the application exhibit from about 2-fold to about 10-fold greater inhibition of HER2 containing one or more mutations as described herein relative to EGFR. In some embodiments, the compounds of the application exhibit from about 10-fold to about 100-fold greater inhibition of HER2 containing one or more mutations as described herein relative to EGFR. In some embodiments, the compounds of the application exhibit from about 100-fold to about 1000-fold greater inhibition of HER2 containing one or more mutations as described herein relative to EGFR. In some embodiments, the compounds of the application exhibit from about 1000-fold to about 10000-fold greater inhibition of HER2 containing one or more mutations as described herein relative to EGFR.

More potent modulation (e.g., inhibition or decrease of the activity) of HER2 containing one or more mutations, such as those described herein, relative to a wild-type HER2, and/or more potent modulation (e.g., inhibition or decrease of the activity) of HER2 and/or HER2 containing one or more mutations, such as those described herein, relative to EGFR or a mutant thereof, provides a novel approach to the treatment or prevention of diseases including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the inhibition of activity of HER2 or a mutant thereof and/or EGFR or a mutant thereof is measured by $IC_{50}$.

In some embodiments, the inhibition of activity of HER2 or a mutant thereof and/or EGFR or a mutant thereof is measured by $EC_{50}$.

In some embodiments, the compounds of the application are potent inhibitors of a drug-resistant HER2 mutant. In some embodiments, the compounds of the application are more potent than one or more known HER2 inhibitors, including but not limited to afatinib, ado-trastuzumab emtansine, allitinib, dacomitinib, canertinib, erlotinib, ertumaxomab, gefitinib, irbinitinib, lapatinib, mubritinib, neratinib, osimertinib, pertuzumab, poziotinib, pyrotinib, sapitinib, tesevatinib, trastuzumab, varlitinib, AC-480, AEE788, AG-490, AG-528, AV-412, BGB-102, BMS-690514, CL-387785, CP-724714, CUDC-101, epigallocatechol gallate, PD158780, NT-113, TAK-285, and WZ4002. In some embodiments, the compounds of the application are at least about 2-fold, 3-fold, 5-fold, 10-fold, 25-fold, 50-fold or about 100-fold more potent (e.g., as measured by $IC_{50}$) than one or more known HER2 inhibitors, including but not limited to afatinib, ado-trastuzumab emtansine, allitinib, dacomitinib, canertinib, erlotinib, ertumaxomab, gefitinib, irbinitinib, lapatinib, mubritinib, neratinib, osimertinib, pertuzumab, poziotinib, pyrotinib, sapitinib, tesevatinib, trastuzumab, varlitinib, AC-480, AEE788, AG-490, AG-528, AV-412, BGB-102, BMS-690514, CL-387785, CP-724714, CUDC-101, epigallocatechol gallate, PD158780, NT-113, TAK-285, and WZ4002.

Potency of a compound can be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a HER2-dependent phosphorylation level in cells expressing a wild-type HER2, or a mutant thereof, such as those described herein, or a fragment of any thereof, and/or determining a EGFR-dependent phosphorylation level in cells expressing a wild-type EGFR, or a mutant thereof, such as those described herein, or a fragment of any thereof.

The selectivity between wild-type HER2 and HER2 containing one or more mutations as described herein, and between HER2 or a mutant thereof and EGFR or a mutant thereof, can be measured using cellular proliferation assays where cell proliferation is dependent on kinase activity. Proliferation assays are performed at a range of inhibitor concentrations (e.g., 10 µM, 3 µM, 1.1 µM, 330 nM, 110 nM, 33 nM, 11 nM, 3 nM, 1 nM) and an $EC_{50}$ is calculated.

An alternative method to measure effects on HER2 activity is to assay phosphorylation of wild-type HER2, and/or a mutant thereof, such as those described herein, wild-type HER2, or a mutant thereof, such as those described herein, can be transfected into cells which do not normally express endogenous HER2. The ability of the inhibitor (using concentrations as above) to inhibit phosphorylation can be assayed.

Another aspect of this application is an isotopically labeled compound of any of the compounds disclosed herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

Definitions

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, In some embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tertbutyl, neopentyl, n-hexyl, heptyl, octyl radicals.

The term "alkenyl," as used herein, denotes a monovalent group derived from a hydrocarbon moiety containing, In some embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, In some embodiments, from two to six, or two to eight carbon atoms having at least one carbon-carbon triple bond. The triple bond may or may not be the point of attachment to another group. Alkynyl groups include, but are not limited to, for example, ethynyl, propynyl, butynyl, 1-methyl-2-butyn-1-yl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which at least one ring atom is selected from S. O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the application, any of the heteroaryls and substituted heteroaryls described herein, can be any aromatic group. Aromatic groups can be substituted or unsubstituted.

The term "cycloalkyl" or "carbocyclyl" as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heterocyclyl," as used herein, refers to a non-aromatic 3-, 4-, 5-, 6- or 7-membered ring or a bi- or tri-cyclic group fused or non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocyclyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure $NH(C_1$-$C_{12}$ alkyl), e.g., $NH(C_1$-$C_6$ alkyl), where $C_1$-$C_6$ alkyl is as previously defined.

The term "dialkylamino" refers to a group having the structure $N(C_1$-$C_{12}$ alkyl)$_2$, e.g., $N(C_1$-$C_6$ alkyl)$_2$, where $C_1$-$C_6$ alkyl is as previously defined.

The terms "hal," "halo," and "halogen," as used herein, refer to an atom selected from fluorine, chlorine, bromine, and iodine.

As described herein, a compound of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen in a given structure with the radical of a specified substituent. Unless otherwise indicated, an optionally substituted group may have a substituent at each substitutable position of the group, and when more than one position in any given structure may be substituted with more than one substituent selected from a specified group, and the substituent may be either the same or different at every position.

It is understood that the alkyl, alkenyl, alkoxy, aryl, heteroaryl, cycloalkyl, or heterocyclyl, or the like can be substituted, by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C3-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)— heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH— heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)—heterocycloalkyl, —NHCO$_2$—C$_1$-C$_{12}$-alkyl, —NHCO$_2$—C$_2$-C$_2$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl. —NHC(S)NH—C$_3$-C$_{12}$-cycloalkyl, —NHC(S)NH-aryl, —NHC(S)NH-heteroaryl, —NHC(S)NH— heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_2$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)— heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

In some embodiments, the substituent present on a nitrogen atom is a nitrogen protecting group (also referred to as an amino protecting group). Nitrogen protecting groups include, but are not limited to, —OH, —OR, —N(R)$_2$, —C(=O)R, —C(=O)N(R)$_2$, —CO$_2$R, —SO$_2$R, —C(=NR)R, —C(=NR)OR, —C(=NR)N(R)$_2$, —SO$_2$N(R)$_2$, —SO$_2$R, —SO$_2$OR, —SOR, —C(=S)N(R)$_2$, —C(=O)SR, —C(=S)SR, C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aryl, and heteroaryl is independently substituted. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-4p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups, such as carbamate groups (e.g., —C(=O)OR), include, but are not limited to, methyl carbamate, ethyl carbamante, 9-fluorenylmethyl carbamate (Fmoc), 9-(2-sulfo)fluorenylmethyl carbamate, 9-(2,7-<dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups, such as sulfonamide groups (e.g., —S(=O)$_2$R), include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), II-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N (1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March's Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR, —OC(=O)R, —OCO$_2$R, —OC(=O)N(R)$_2$, —OC(=NR)R, —OC(=NR)OR, —OC(=NR)N(R)$_2$, —OS(=O)R, —OSO$_2$R, —OP(R)$_2$, —OP(R)$_3$; —OP(=O)$_2$R, —OP(=O)(R)$_2$, —OP(=O)(OR)$_2$, —OP(=O)$_2$N(R)$_2$, and —OP(=O)(NR)$_2$). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leionyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paranglioma; and Adrenal glands: neuroblastoma. Thus, the term "cancerous cell" as provided herein, includes a cell afflicted by any one of the above-identified conditions.

AC-480 refers to [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate.

AEE788 refers to 6-[4-[(4-ethylpiperazin-1-yl)methyl]phenyl]-N-[(1R)-1-phenylethyl]-7H-pyrrolo[2,3-d]pyrimidin-4-amine.

AG-490 refers to (E)-N-benzyl-2-cyano-3-(3,4-dihydroxyphenyl)prop-2-enamide.

AG-528 refers to (E)-2-(2,3-dihydroindole-1-carbonyl)-3-(3,4-dihydroxyphenyl)prop-2-enenitrile.

AV-412 refers to N-[4-(3-chloro-4-fluoroanilino)-7-[3-methyl-3-(4-methylpiperazin-1-yl)but-1-ynyl]quinazolin-6-yl]prop-2-enamide;4-methylbenzenesulfonic acid.

BGB-102 refers to 17-bromo-1,8,9,10,11,12,13,14-octahydro-20-methoxy-13-methyl-4,6-ethenopyrimido[4,5-b][6,1,12]benzoxadiazacyclopentadecine.

BMS-690514 refers to (3R,4R)-4-amino-1-[[4-(3-methoxyanilino)pyrrolo[2,1-f][1,2,4]triazin-5-yl]methyl]piperidin-3-ol.

CL-387785 refers to N-(4-((3-bromophenyl)amino)-6-quinazolinyl)-2-butynamide.

CP-724714 refers to 2-methoxy-N-(3-(4-((3-methyl-4-((6-methyl-3-pyridinyl)oxy)phenyl)amino)-6-quinazolinyl)-2-propen-1-yl)-acetamide.

CUDC-101 refers to 7-((4-(3-Ethynylphenylamino)-7-methoxyquinazolin-6-yl)oxy)-N-hydroxyheptanamide.

Epigallocatechol gallate refers to 5,7-dihydroxy-2-(3,4,5-trihydroxyphenyl)-3,4-dihydro-2H-chromen-3-yl 3,4,5-trihydroxybenzoate.

PD158780 refers to N4-(3-bromophenyl)-N6-methylpyrido[3,4-d]pyrimidine-4,6-diamine.

NT-113 refers to (E)-N-(7-(((1R,5S,6s)-3-oxabicyclo[3.1.0]hexan-6-yl)ethynyl)-4-((3-chloro-4-fluorophenyl)amino)quinazolin-6-yl)-4-(dimethylamino)but-2-enamide.

TAK-285 refers to N-(2-(4-((3-chloro-4-(3-(trifluoromethyl)phenoxy)phenyl)amino)-5H-pyrrolo[3,2-d]pyrimidin-5-yl)ethyl)-3-hydroxy-3-methylbutanamide.

WZ4002 refers to N-(3-((5-chloro-2-((2-methoxy-4-(4-methylpiperazin-1-yl)phenyl)amino)pyrimidin-4-yl)oxy)phenyl)acrylamide.

The term "EGFR" herein refers to epidermal growth factor receptor kinase.

The term "HER2", "Her2", "ERBB2", or "Erbb2" herein refers to human epidermal growth factor receptor 2. HER2 is also known as CD340 or Neu.

As used herein, the term "mutant EGFR" or "EGFR mutant" refers to EGFR with one or more mutations. In some embodiments, the EGFR mutant has one or more mutations of exon 18, exon 19 (e.g., exon 19 deletion or exon 19 insertion), exon 20 (e.g., exon 20 insertion), and/or exon 21.

In some embodiments, the mutant EGFR contains one or more mutations selected from an exon 19 deletion (Del 19), an exon 20 insertion (Ins 20), L718Q, G719S, G719C, G719A, D761Y, T790M, C797S, L844V, T854A, L858R, L861Q, I941R, V948R, D770delinsGY, D770_N771insSVD, V769_D770insASV, Y764_V765insHH, H773dupH, D770_N771insNPG, H773_V774insNPH, P772_H773insPNP, N771_P772insH, A775_G776insYVMA, A763_Y764insFQEA, V774_C775insHV, N771_P772insV, D770_N771insGL, N771delinsGY, and H773_V774insAH. In some embodiments, the mutant EGFR contains one or more mutations selected from D770delinsGY, D770_N771insSVD, V769_D770insASV, Y764_V765insHH, H773dupH, D770_N771insNPG, H773_V774insNPH, P772_H773insPNP, and N771_P772insH.

In some embodiments, the mutant EGFR contains a combination of two or more mutations (such as mutations described herein). In some embodiments, the mutant EGFR contains a combination of two or more mutations selected from Del 19/L718Q, Del 19/T790M, Del 19/L844V, Del 19/T790M/L718Q, Del/T790M/C797S, Del 19/T790M/L844V, L858R/L718Q, L858R/L844V, L858R/T790M, L858R/T790M/L718Q, L858R/T790M/C797S, and L858R/T790M/I941R.

An EGFR sensitizing mutation comprises without limitation G719S, G719C, G719A, L861Q, L858R, Del 19, and/or Ins 20. A drug-resistant EGFR mutant can have without limitation a drug resistance mutation comprising L718Q, D761Y, T790M, T854A, D770delinsGY, D770_N771insSVD, V769_D770insASV, Y764_V765insHH, A775_G776insYVMA, and/or H773dupH.

As used herein, the term "mutant HER2" or "HER2 mutant" refers to HER2 with one or more mutations. In some embodiments, the HER2 mutant has one or more mutations of exon 18, exon 19 (e.g., exon 19 deletion or exon 19 insertion), exon 20 (e.g., exon 20 insertion), and/or exon 21.

In some embodiments, the mutant HER2 contains one or more mutations selected from an exon 19 deletion (Del 19), an exon 20 insertion (Ins 20), T798M, T798I, L869R, V659E, G660D, V777L, G776V, S779T, D769H, V842I, L755S, R678Q, G309A, G660R, A775_G776insYVMA, A775_G776insSVMA, A775_G776insI, G776delinsVC, G776delinsLC, P780_Y781insGSP, M774delinsWLV, and G778_S779insCPG, G776delinsVV, G776C V777insC, A775insV G776G. In some embodiments, the mutant EGFR contains a combination of two or more mutations (such as mutations described herein).

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating", and "treatment" refer to a method of alleviating or abating a disease and/or its attendant symptoms.

"Prevent", "preventing", and "prevention" describes reducing or eliminating the onset of a disease, condition, or disorder and/or symptoms or complications thereof.

The terms "disease(s)", "disorder(s)", and "condition(s)" are used interchangeably, unless the context clearly dictates otherwise.

The term "therapeutically effective amount" or "effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons. Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med Chem*. 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a compound of the application, or an enantiomer, diastereomer, stereoisomer, or pharmaceutically acceptable salt or solvate thereof, and a pharmaceutically acceptable carrier.

In another aspect, the application provides a kit comprising a compound capable of inhibiting protein kinase activity of at least one protein kinase selected from one or more compounds disclosed herein, or a pharmaceutically acceptable salt, hydrate, solvate, prodrug, stereoisomer, or tautomer thereof, optionally in combination with a second agent and instructions for use in treating cancer. In one embodiment, the compound in the kit inhibits more than one protein kinase In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base. Alternatively, the salt forms of the compounds of the application can be prepared using salts of the starting materials or intermediates.

The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons. Inc., 1999.

Compounds of the present application can be conveniently prepared or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_7$) occurs more than one time in any constituent or formula for a compound, its definition at each occurrence is independent of its definition at every other occurrence. Thus, for example, if a group is shown to be substituted with one or more $R_7$ moieties, then $R_7$ at each occurrence is selected independently from the definition of $R_7$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of Synthesizing the Compounds

A compound of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof. Suitable synthetic routes are depicted in the schemes below.

A compound of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5*th* edition, John Wiley & Sons: New York, 2001; and Greene, T. W., Wuts, P. G. M., *Protective Groups in Organic Synthesis.* 3*rd* edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of a compound of the present application.

A compound disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of a compound disclosed herein.

Those skilled in the art will recognize if a stereocenter exists in a compound disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example. "Stereochemistry of Organic Compounds" by E. L. Eliel, S. H. Wilen, and L. N. Mander (Wiley-Interscience, 1994).

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

By way of example, a compound of the present application can be synthesized using the methods described below, together with synthetic methods known in the art of synthetic organic chemistry, or variations thereon as appreciated by those skilled in the art. Preferred methods include but are not limited to those methods described below.

In one embodiment, a compound of the present application can be synthesized by following the steps outlined in General Scheme A. Starting materials are either commercially available or made by known procedures in the reported literature or as illustrated.

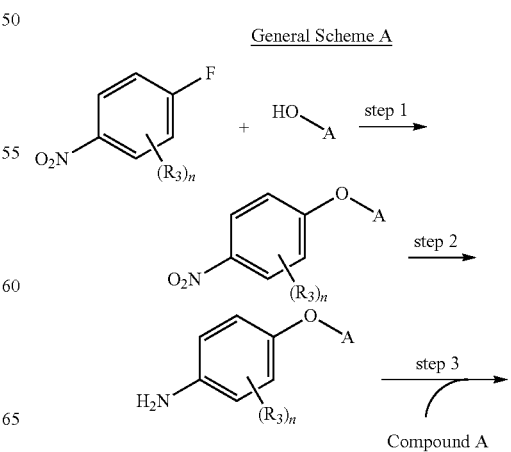

General Scheme A

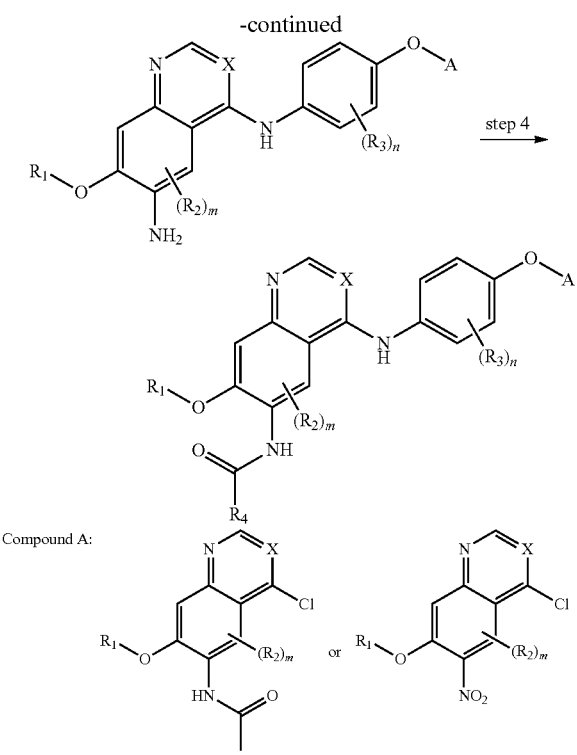

Compound A:

A mixture of enantiomers, diastereomers, and/or cis/trans isomers resulting from the processes described above can be separated into their single components by chiral salt technique, chromatography using normal phase, or reverse phase or chiral column, depending on the nature of the separation.

It should be understood that in the description and formulae shown above, the various groups, such as $R_1$-$R_6$, m, and n, are as defined herein, except where otherwise indicated. Furthermore, for synthetic purposes, the compounds in the Schemes are mere representatives with elected substituents to illustrate the general synthetic methodology of a compound disclosed herein.

Starting materials, reagents and solvents were purchased from commercial suppliers and were used without further purification unless otherwise noted. All reactions were monitored using a Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=85% A at 0 min, 1% A at 1.6 min; solvent A=0.1% formic acid in Water; solvent B=0.1% formic acid in Acetonitrile; flow rate: 0.6 mL/min. Reaction products were purified by flash column chromatography using CombiFlash®Rf with Teledyne Isco RediSep®Rf columns (4 g, 12 g, 24 g, 40 g, or 80 g) and Waters HPLC system using SunFiren™ Prep C18 column (19×100 mm, 5 μm particle size): solvent gradient=80% A at 0 min, 10% A at 25 min: solvent A=0.035% TFA in Water; solvent B=0.035% TFA in MeOH; flow rate: 25 mL/min. $^1$H NMR spectra were recorded on 500 MHz Bruker Advance iii spectrometers. Chemical shifts are reported in parts per million (ppm, δ) downfield from tetramethylsilane (TMS). Coupling constants (J) are reported in Hz. Spin multiplicities are described as br (broad), s (singlet), d (doublet), t (triplet), q (quartet) and m (multiplet).

Biological Assays

A compound of the present application can be tested for its activity with various biological assays. Suitable assays include, but are not limited to, MTS assay and Western blot analysis. Non-limiting, representative assays are described briefly below.

Proliferation Inhibition Assay

Cell growth and growth inhibition were evaluated by 5-(3-carboxymethoxyphenyl)-2-(4-sulfophenyl)-2H-tetrazolium (MTS) assay. A total of 3,000-4,000 cells were plated per well in 96-well plates and treated with each drug (at a dose range from 1 nM to 10 μM) for 3 days. Each experimental point was conducted in six replicates and all tests were repeated more than three times. $IC_{50}$ data was obtained from a nonlinear regression model with sigmoidal dose response using GraphPad Prism (GraphPad Software, Inc.).

Western Blot Analysis

Ba/F3 cells and H1781 cells were plated in 6-well plates at $5\times10^5$ cells per well and treated with the indicated doses of inhibitors for 6 and 24 hours, respectively. After washing with cold PBS, cells were lysed with RIPA buffer (Boston BioProducts) supplemented with protease and phosphatase inhibitors (Sigma Aldrich). For immunoblotting, 20 μg of total cell lysates were separated by 4-12% SDS-PAGE, transferred to poly vinylidene difluoride membranes, and probed with the following antibodies: phospho-EGFR (Tyr1068), total-EGFR, phospho-HER2 (Tyr1196), total-HER2, phospho-Akt (Ser473), total-Akt, phospho-Erk1/2 (Thr202/Tyr204) and total-Erk1/2 from Cell Signaling Technology, and HSP90 antibody purchased from Santa Cruz Biotechnology.

Methods of the Application

Another aspect of the present application relates to a method of modulating (e.g., inhibiting or decreasing) the activity of HER2, and/or a mutant thereof, comprising administering to a subject in need thereof an effective amount of a compound of the present application (e.g., a compound of Formula I), or a pharmaceutically acceptable salt or solvate thereof.

Another aspect of the present application relates to a method of treating or preventing a disease or disorder (e.g., cancer) in which HER2, and/or a mutant thereof, plays a role, comprising administering to a subject in need thereof an effective amount of a compound of the present application (e.g., a compound of Formula I), or a pharmaceutically acceptable salt or solvate thereof.

In some embodiments, the disease or disorder is resistant to a HER2 targeted therapy, such as those described herein, for example, a therapy with afatinib, neratinib, and/or dacomitinib, with trastuzumab and/or chemotherapy, with lapatinib and/or taxane, with neratinib and/or paclitaxel, or with trastuzumab and/or paclitaxel.

In some embodiments, the HER2 targeted therapy is a therapy with an inhibitor of HER2, and/or a mutant thereof, such as the inhibitors described herein.

In some embodiments, the HER2 targeted therapy is a therapy with afatinib, ado-trastuzumab emtansine, allitinib, dacomitinib, canertinib, erlotinib, ertumaxomab, gefitinib, irbinitinib, lapatinib, mubritinib, neratinib, osimertinib, pertuzumab, poziotinib, pyrotinib, sapitinib, tesevatinib, trastuzumab, varlitinib, AC-480, AEE788, AG-490, AG-528, AV-412, BGB-102, BMS-690514, CL-387785, CP-724714, CUDC-101, epigallocatechol gallate, PD158780, NT-113, TAK-285, WZ4002, or any combination thereof.

In some embodiments, the HER2 targeted therapy is a therapy with afatinib, ado-trastuzumab emtansine, dacomitinib, lapatinib, neratinib, pertuzumab, trastuzumab, or any combination thereof. In some embodiments, the HER2 targeted therapy is a therapy with afatinib. In some embodiments, the HER2 targeted therapy is a therapy with ado-trastuzumab emtansine. In some embodiments, the HER2 targeted therapy is a therapy with dacomitinib. In some embodiments, the HER2 targeted therapy is a therapy with lapatinib. In some embodiments, the HER2 targeted therapy is a therapy with neratinib. In some embodiments, the HER2 targeted therapy is a therapy with pertuzumab. In some embodiments, the HER2 targeted therapy is a therapy with trastuzumab.

In some embodiments, the HER2 targeted therapy is a therapy with afatinib, ado-trastuzumab emtansine, allitinib, dacomitinib, canertinib, erlotinib, ertumaxomab, gefitinib, irbinitinib, lapatinib, mubritinib, neratinib, osimertinib, pertuzumab, poziotinib, pyrotinib, sapitinib, tesevatinib, trastuzumab, varlitinib, AC-480, AEE788, AG-490, AG-528, AV-412, BGB-102, BMS-690514, CL-387785, CP-724714, CUDC-101, epigallocatechol gallate, PD158780, NT-113, TAK-285, WZ4002, or any combination thereof, and further in combination with a chemotherapy or a cytotoxic agent. In some embodiments, the chemotherapy or cytotoxic agent is taxane. In some embodiments, the chemotherapy or cytotoxic agent is paclitaxel.

In some embodiments, the disease or disorder is cancer or a proliferative disease.

In some embodiments, the cancer is associated with HER2 or a mutant thereof. In some embodiments, the cancer is HER2-dependent cancer. In some embodiments, the cancer is HER2-positive cancer.

In some embodiments, the cancer cell comprises a mutant HER2. In some embodiments, the cancer is a cancer of B cell origin. In some embodiments, the cancer is a lineage dependent cancer. In some embodiments, the cancer is a lineage dependent cancer where HER2, and/or a mutant thereof, plays a role in the initiation and/or development of the cancer.

In some embodiments, the cancer is breast cancer, non-small cell lung cancer, gastric cancer, or ovarian cancer.

In some embodiments, the cancer is breast cancer (e.g., HER2-positive breast cancer or breast cancer harboring a HER2 mutant).

In some embodiments, the cancer is lung cancer (e.g., mutant HER2-dependent lung cancer).

In some embodiments, the subject is identified as being in need of modulation (e.g., inhibition or decrease of the activity) of HER2 or a mutant thereof for the treatment or prevention of the disease or disorder.

In some embodiments, the application provides a method of treating any of the disorders described herein, wherein the subject is a human. In some embodiments, the application provides a method of preventing any of the disorders described herein, wherein the subject is a human.

Another aspect of the present application relates to a compound of the present application (e.g., a compound of Formula I), or a pharmaceutically acceptable salt or solvate thereof, for modulating (e.g., inhibiting or decreasing) the activity of HER2 or a mutant thereof; for treating or preventing a disease or disorder, such as a kinase mediated disease or disorder; for treating or preventing a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for treating or preventing cancer, wherein the cancer cell comprises a mutant HER2; or for treating or preventing a disease or disorder, such as a kinase mediated disease or disorder in a subject identified as being in need of modulation (e.g., inhibition or decrease of the activity) of HER2 or a mutant thereof for the treatment or prevention of the disease or disorder.

Another aspect of the present application relates to a compound of the present application (e.g., a compound of Formula I), or a pharmaceutically acceptable salt or solvate thereof, for use in the modulation (e.g., inhibition or decrease of the activity) of HER2 or a mutant thereof; in the treatment or prevention of a disease or disorder, such as a kinase mediated disease or disorder; in the treatment or prevention of a disease or disorder resistant to HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); in the treatment or prevention of cancer, wherein the cancer cell comprises a mutant HER2; or in the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

Another aspect of the present application relates to use of a compound of the present application (e.g., a compound of Formula I), or a pharmaceutically acceptable salt or solvate thereof, in the modulation (e.g., inhibition or decrease of the activity) of HER2 or a mutant thereof; in the treatment or prevention of a disease or disorder, such as a kinase mediated disease or disorder; in the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); in the treatment or prevention of cancer, wherein the cancer cell comprises a mutant HER2; or in the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

Another aspect of the present application relates to a compound of the present application (e.g., a compound of Formula I), or a pharmaceutically acceptable salt or solvate thereof, for use in the manufacture of a medicament for the modulation (e.g., inhibition or decrease of the activity) of HER2 or a mutant thereof; for the treatment or prevention of a disease or disorder, such as a kinase mediated disease or disorder; for the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for the treatment or prevention of cancer, wherein the cancer cell comprises a mutant HER2; or for the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

Another aspect of the present application relates to use of a compound of the present application (e.g., a compound of Formula I), or a pharmaceutically acceptable salt or solvate thereof, in the manufacture of a medicament for the modulation (e.g., inhibition or decrease of the activity) of HER2 or a mutant thereof; for the treatment or prevention of a disease or disorder, such as a kinase mediated disease or disorder; for the treatment or prevention of a disease or disorder resistant to a HER2 targeted therapy (e.g., a therapy with afatinib, neratinib, and/or dacomitinib, with trastuzumab and/or chemotherapy, with lapatinib and/or taxane, with neratinib and/or paclitaxel, or with trastuzumab and/or paclitaxel); for the treatment or prevention of cancer, wherein the cancer cell comprises a mutant HER2; or for the treatment or prevention of a disease or disorder, such as a kinase mediated disease or disorder in a subject identified as being in need of modulation (e.g., inhibition or decrease of the activity) of HER2 or a mutant thereof for the treatment or prevention of the disease or disorder.

In some embodiments, the HER2 is a wild-type HER2. In other embodiments, the HER2 has one or more mutations, such as those described herein.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma. Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma. Ewing sarcoma, and plasmocytoma. In one aspect of the application, the present application provides for the use of one or more a compound of the application in the manufacture of a medicament for the treatment of cancer, including without limitation the various types of cancer disclosed herein.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intraepithelial tissue.

Pharmaceutical Compositions

In another aspect, the application provides a pharmaceutical composition comprising a compound disclosed herein, or a pharmaceutically acceptable ester, salt, or prodrug thereof, together with a pharmaceutically acceptable carrier.

A compound of the application can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures;

and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing a compound of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, a compound of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present application.

In another aspect, the application provides a kit comprising a compound capable of inhibiting kinase activity selected from one or more compounds of disclosed herein, or a pharmaceutically acceptable salt, hydrate, solvate, prodrug, stereoisomer, or tautomer thereof, and instructions for use in treating cancer.

In another aspect, the application provides a kit comprising a compound capable of inhibiting EGFR and/or HER2 activity selected from a compound disclosed herein, or a pharmaceutically acceptable salt, hydrate, solvate, prodrug, stereoisomer, or tautomer thereof.

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

EXAMPLES

General Description for Synthetic Examples

Starting materials, reagents and solvents were purchased from commercial suppliers and were used without further purification unless otherwise noted. All reactions were monitored using a Waters Acquity UPLC/MS system (Waters PDA eλ Detector, QDa Detector, Sample manager—FL, Binary Solvent Manager) using Acquity UPLC®, BEH C18 column (2.1×50 mm, 1.7 µm particle size): solvent gradient=85% A at 0 min, 1% A at 1.6 min; solvent A=0.1% formic acid in Water; solvent B=0.1% formic acid in Acetonitrile; flow rate: 0.6 mL/min. Reaction products were purified by flash column chromatography using CombiFlash©Rf with Teledyne Isco RediSep®R<sub>f</sub> columns (4 g, 12 g, 24 g, 40 g, or 80 g) and Waters HPLC system using SunFire™ Prep C18 column (19×100 mm, 5 μm particle size): solvent gradient=80% A at 0 min, 10% A at 25 min; solvent A=0.035% TFA in Water; solvent B=0.035% TFA in MeOH; flow rate: 25 mL/min. $^1$H NMR spectra were recorded on 500 MHz Bruker Avance III spectrometers. Chemical shifts are reported in parts per million (ppm, δ) downfield from tetramethylsilane (TMS). Coupling constants (J) are reported in Hz. Spin multiplicities are described as br (broad), s (singlet), d (doublet), t (triplet), q (quartet), m (multiplet).

Example 1. Synthesis of Compound 1

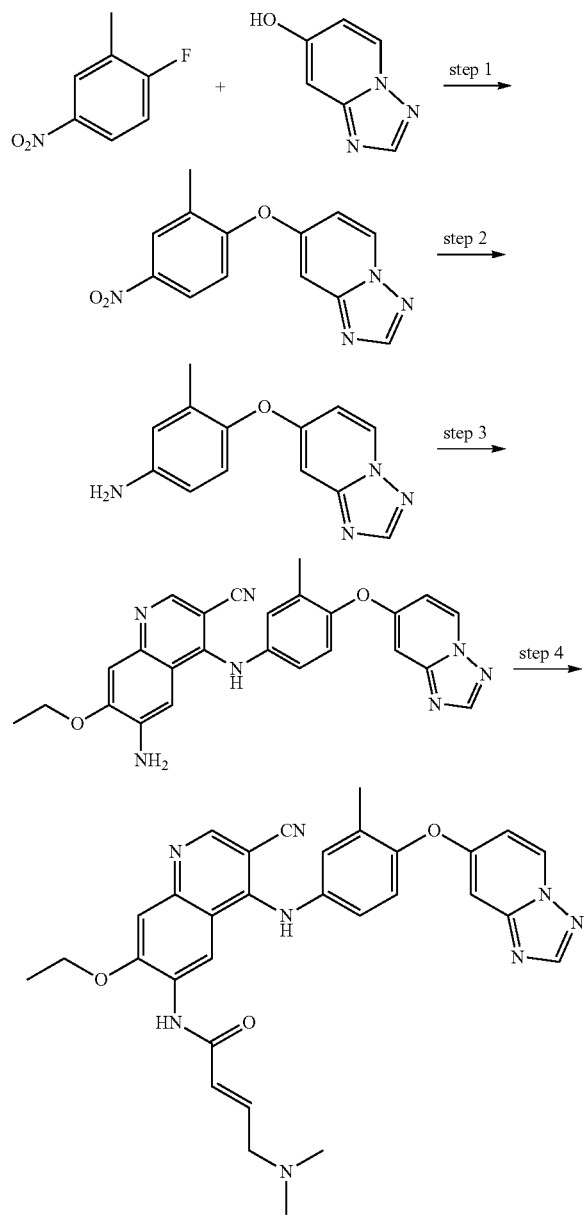

Step 1. Synthesis of 7-(2-methyl-4-nitrophenoxy)-[1,2,4]triazolo[1,5-a]pyridine

The mixture of 1-fluoro-2-methyl-4-nitrobenzene (96 mg, 0.617 mmol), triazolo[1,5-a]pyridin-7-ol (100 mg, 0.740 mmol) and cesium carbonate (482 mg, 1.48 mmol) in dimethyl sulfoxide (2.5 ml) was stirred at 80° C. for 3 hr. The resulting mixture was poured into ice water and the precipitate was filtered and dried using blowing nitrogen gas to give 4-([1,2,4]triazolo[1,5-a]pyridin-7-yloxy)-3-methylaniline as a brown solid (145 mg, 87%).

Step 2. Synthesis of 4-([1,2,4]triazolo[,5-a]pyridin-7-yloxy)-3-methylaniline

To a solution of 7-(2-methyl-4-nitrophenoxy)-[1,2,4]triazolo[1,5-a]pyridine (500 mg, 1.85 mmol) in a mixture of THF/MeOH (5 ml/3 ml) were added saturated ammonium chloride (2 ml) and iron powder (150 mg). After stirring for 6 hr, the mixture was filtered and the filtrate was washed with sat. NaHCO$_3$, dried over sodium sulfate, filtered and concentrated. The residue was purified by flash column chromatography (DCM:1 N NH$_3$ in MeOH) to give 4-([1,2,4]triazolo[1,5-a]pyridin-7-yloxy)-3-methylaniline as a yellow solid (333 mg, 75%).

Step 3. Synthesis of 4-((4-([1,2,4]triazolo[1,5-a]pyridin-7-yloxy)-3-methylphenyl)amino)-6-amino-7-ethoxyquinoline-3-carbonitrile To a solution of N-(4-chloro-3-cyano-7-ethoxyquinolin-6-yl)acetamide (301 mg, 1.04 mmol) and 4-([1,2,4]triazolo[1,5-a]pyridin-7-yloxy)-3-methylaniline (250 mg, 1.04 mmol) in 2-butanol (3.5 ml) was added trifluoroacetic acid (1.5 ml). After stirring at 80° C. for 4 hr, 4 M HCl in dioxane was added to the reaction mixture and stirred at 80° C. for additional 2 hr. The resulting mixture was cooled to room temperature, poured into ether. The precipitate was collected by filtration which was carried onto next step without further purification (441 mg, 87%).

Step 4. Synthesis of (E)-N-(4-((4-([1,2,4]triazolo[1,5-a]pyridin-7-yloxy)-3-methylphenyl)amino)-3-cyano-7-ethoxyquinolin-6-yl)-4-(dimethylamino)but-2-enamide To a solution of 4-((4-([1,2,4]triazolo[1,5-a]pyridin-7-yloxy)-3-methylphenyl)amino)-6-amino-7-ethoxyquinoline-3-carbonitrile (100 mg, 0.221 mmol) in MeCN (2 mL) were added DIEA (154 μl, 0.884 mmol) and (E)-4-bromobut-2-enoyl chloride (60 mg, 0.332 mmol). After stirring for 15 min., a 2 M solution of dimethylamine in THF (166 μl, 0.332 mmol) was added to the reaction mixture. After stirring at 60° C. for 30 min, the reaction mixture was purified by prepHPLC to obtain (E)-N-(4-((4-([1,2,4]triazolo[1,5-a]pyridin-7-yloxy)-3-methylphenyl)amino)-3-cyano-7-ethoxyquinolin-6-yl)-4-(dimethylamino)but-2-enamide (43 mg, 35%). $^1$H NMR (500 MHz, DMSO-d$_6$) δ 9.75 (s, 1H), 9.51 (s, 1H), 9.03 (s, 1H), 8.92 (d, J=7.3 Hz, 1H), 8.51 (s, 1H), 8.36 (s, 1H), 7.41 (s, 1H), 7.31 (s, 1H), 7.23-7.18 (m, 2H), 7.05 (dd, J=7.5, 2.6 Hz, 1H), 6.88 (d, J=2.4 Hz, 1H), 6.80 (dt, J=15.5, 6.0 Hz, 1H), 6.62 (d, J=15.2 Hz, 1H), 4.32 (q, J=6.9 Hz, 2H), 3.13 (d, J=5.2 Hz, 2H), 2.21 (s, 6H), 2.15 (s, 3H), 1.48 (t, J=6.9 Hz, 3H).

Example 2. Synthesis of Compound 2

Compound 2 was synthesized following the process described in Example 1 and with appropriate starting materials. $^1$H NMR (500 MHz, DMSO-d$_6$) δ 9.86 (s, 1H), 9.52 (s, 1H), 9.04 (s, 1H), 8.95 (d, J=7.3 Hz, 1H), 8.60 (s, 1H), 8.40 (s, 1H), 7.49-7.42 (m, 2H), 7.36 (dd, J=11.9, 1.8 Hz, 1H), 7.18 (br d, J=8.5 Hz, 1H), 7.11 (dd, J=7.5, 2.6 Hz, 1H), 7.05 (d, J=2.4 Hz, 1H), 6.80 (dt, J=15.3, 6.0 Hz, 1H), 6.64 (d, J=15.3 Hz, 1H), 4.34 (q, J=6.9 Hz, 2H), 3.14 (d, J=4.3 Hz, 2H), 2.22 (s, 6H), 2.15 (s, 3H), 1.48 (t, J=6.9 Hz, 3H).

Example 3. Synthesis of Compound 3

Compound 3 was synthesized following the process described in Example 1 and with appropriate starting materials. $^1$H NMR (500 MHz, DMSO-d$_6$) δ 9.86 (br s, 1H), 9.49 (s, 1H), 9.04 (s, 1H), 8.95 (d, J=7.6 Hz, 1H), 8.58 (br s, 1H), 8.39 (s, 1H), 7.53 (br s, 1H), 7.47-7.40 (m, 2H), 7.32 (d, J=8.2 Hz, 1H), 7.08 (dd, J=7.5, 2.6 Hz, 1H), 6.89 (d, J=2.4 Hz, 1H), 6.81 (dt, J=15.3, 6.0 Hz, 1H), 6.62 (d, J=15.6 Hz, 1H), 4.33 (q, J=7.0 Hz, 2H), 3.08 (d, J=5.5 Hz, 2H), 2.18 (s, 6H), 1.48 (t, J=6.9 Hz, 3H).

Example 4. Synthesis of Compound 4

Compound 4 was synthesized following the process described in Example 1 and with appropriate starting materials. $^1$H NMR (500 MHz, DMSO-d$_6$) δ 9.72 (s, 1H), 9.54 (s, 1H), 9.02 (s, 1H), 8.53 (d, J=7.6 Hz, 1H), 8.50 (s, 1H), 7.82 (s, 1H), 7.41 (d, J=8.9 Hz, 2H), 7.28 (s, 1H), 7.21-7.11 (m, 2H), 6.84-6.75 (m, 2H), 6.69-6.59 (m, 2H), 4.32 (q, J=7.0 Hz, 2H), 3.25-3.15 (m, 2H), 2.27 (s, 6H), 2.16 (s, 3H), 1.48 (t, J=6.9 Hz, 3H).

Example 5. Synthesis of Compound 5

Compound 5 was synthesized following the process described in Example 1 and with appropriate starting materials. $^1$H NMR (500 MHz, DMSO-do) δ 9.73 (s, 1H), 9.51 (s, 1H), 9.03 (s, 1H), 8.65 (d, J=7.3 Hz, 1H), 8.51 (s, 1H), 7.90 (d, J=2.1 Hz, 1H), 7.40 (s, 1H), 7.28 (s, 1H), 7.21-7.11 (m, 2H), 6.83-6.73 (m, 3H), 6.62 (d, J=15.3 Hz, 1H), 6.30-6.27 (m, 1H), 4.32 (q, J=6.9 Hz, 2H), 3.11 (m, 2H), 2.20 (s, 6H), 2.15 (s, 3H), 1.48 (t, J=6.9 Hz, 3H).

Example 6. Synthesis of Compound 6

Compound 6 was synthesized following the process described in Example 1 and with appropriate starting materials. $^1$H NMR (500 MHz, DMSO-do) δ 9.74 (s, 1H), 9.72 (s, 1H), 8.98 (s, 1H), 8.48 (s, 1H), 7.49 (d, J=8.5 Hz, 1H), 7.40 (s, 1H), 7.26 (s, 1H), 7.22 (d, J=2.7 Hz, 1H), 7.17-7.11 (m, 1H), 6.96 (d, J=8.5 Hz, 1H), 6.87 (s, 1H), 6.83-6.71 (m, 3H), 6.38 (d, J=2.7 Hz, 1H), 4.32 (q, J=6.9 Hz, 2H), 3.81 (br s, 2H), 3.64 (s, 3H), 2.70 (s, 6H), 2.19 (s, 3H), 1.47 (t, J=7.0 Hz, 3H).

Example 7. Biological Assays

Expression Constructs and Cell Culture:

All ERBB insertion mutations were generated by using the Quikchange II XL Site-Directed Mutagenesis Kit (Agilent Tech) according to the manufacturer's protocol. The insertion mutations and wildtype form of human EGFR and HER2 were transduced into Ba/F3 cells by retroviral infection followed by treatment of puromycin and withdrawal of interleukin-3 for selection. Transformed Ba/F3 cells and the NSCLC cell line H1781 (with HER2 insertion VC) were cultured in Roswell Park Memorial Institute-1640 medium (Gibco) with 10% fetal bovine serum and 1% penicillin/streptomycin (Gibco). Wild-type EGFR Ba/F3 cells were cultured in the same media supplemented with EGF (10 ng/ml).

Proliferation Inhibition Assays:

Cell growth inhibition was assessed by MTS assay for Ba/F3 and H1781 cells. A total of 3,000-4,000 cells were seeded for per well in 96-well plates, and were exposed to representative compounds of the application (1 nM to 10 μM) for 72 hours. All experimental points included 6 wells. Data were normalized to untreated cells and displayed graphically using GraphPad Prism (GraphPad Software, Inc.). The growth curves were fitted using a nonlinear regression model with sigmoidal dose response.

Western Blot Analysis:

Ba/F3 cells and H1781 cells were plated at 5×10$^5$ cells per well in 6-well plates and treated with representative compounds of the application for 6 hours and 24 hours, respectively. After washing with cold PBS, cells were lysed with RIPA buffer (Boston BioProducts®) supplemented with protease and phosphatase inhibitors (Sigma Aldrich®). For immunoblotting, 20 μg of total cell lysates were separated by 4-12% SDS-PAGE gel, transferred to polyvinylidene difluoride membranes, and probed with the following antibodies: phospho-EGFR (Tyr1068), total-EGFR, phospho-HER2 (Tyr1196), total-HER2, phospho-Akt (Ser473), total-Akt, phospho-Erk1/2 (Thr202/Tyr204) and total-Erk1/2 (Cell Signaling Technology®), and HSP90 antibody (Santa Cruz Biotechnology®).

Example 8. Assessing the Activity of the Representative Compounds of the Present Application in Inhibiting HER2

Activities of representative compounds of the present application in inhibiting HER2 were tested by MTS assay (for Ba/F3 cells and H1781 cells). For each assay, a total of 3,000-4,000 cells were seeded per well in 96-well plates and were exposed to indicated compounds with a concentration of 10 to 10 μM for 72 hours.

Western blot analysis was then performed on the cells. The cells were plated at 5×10$^5$ cells per well in 6-well plates and treated with the indicated concentrations of the compound. After 6 hours or 24 hours of treatment (for Ba/F3 cells and H1781 cells, respectively), cells were washed with cold PBS, and were lysed with RIPA buffer (Boston Bio-Products®) supplemented with protease and phosphatase inhibitors (Sigma Aldrich®). For immunoblotting, 20 μg of total cell lysates were separated by 4-12% SDS-PAGE gel, transferred to polyvinylidene difluoride membranes, and probed with the following antibodies: phospho-EGFR (Tyr1068), total-EGFR, phospho-HER2 (Tyr1196), total-HER2, phospho-Akt (Ser473), total-Akt, phospho-Erk1/2 (Thr202/Tyr204) and total-Erk1/2 (Cell Signaling Technology®), and HSP90 antibody (Santa Cruz Biotechnology®).

Figure 1B:
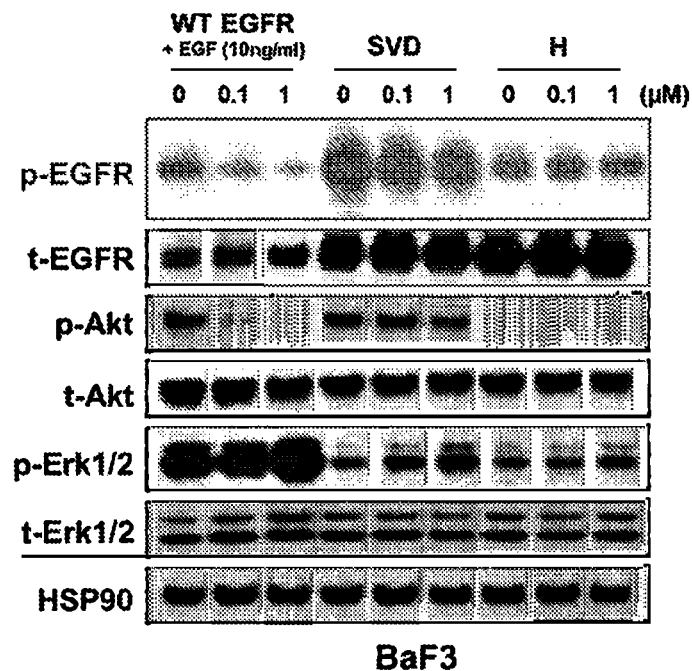
FIG. 1B is a Western blot showing the effects of Compound 1 on EGFR phosphorylation and its downstream signaling components at the indicated concentrations in Ba/F3 cells expressing wild-type EGFR, EGFR InsSVD mutant ("SVD"), or EGFR InsH mutant ("H"), treated with Compound 1 for 6 hours.
Figure 2:
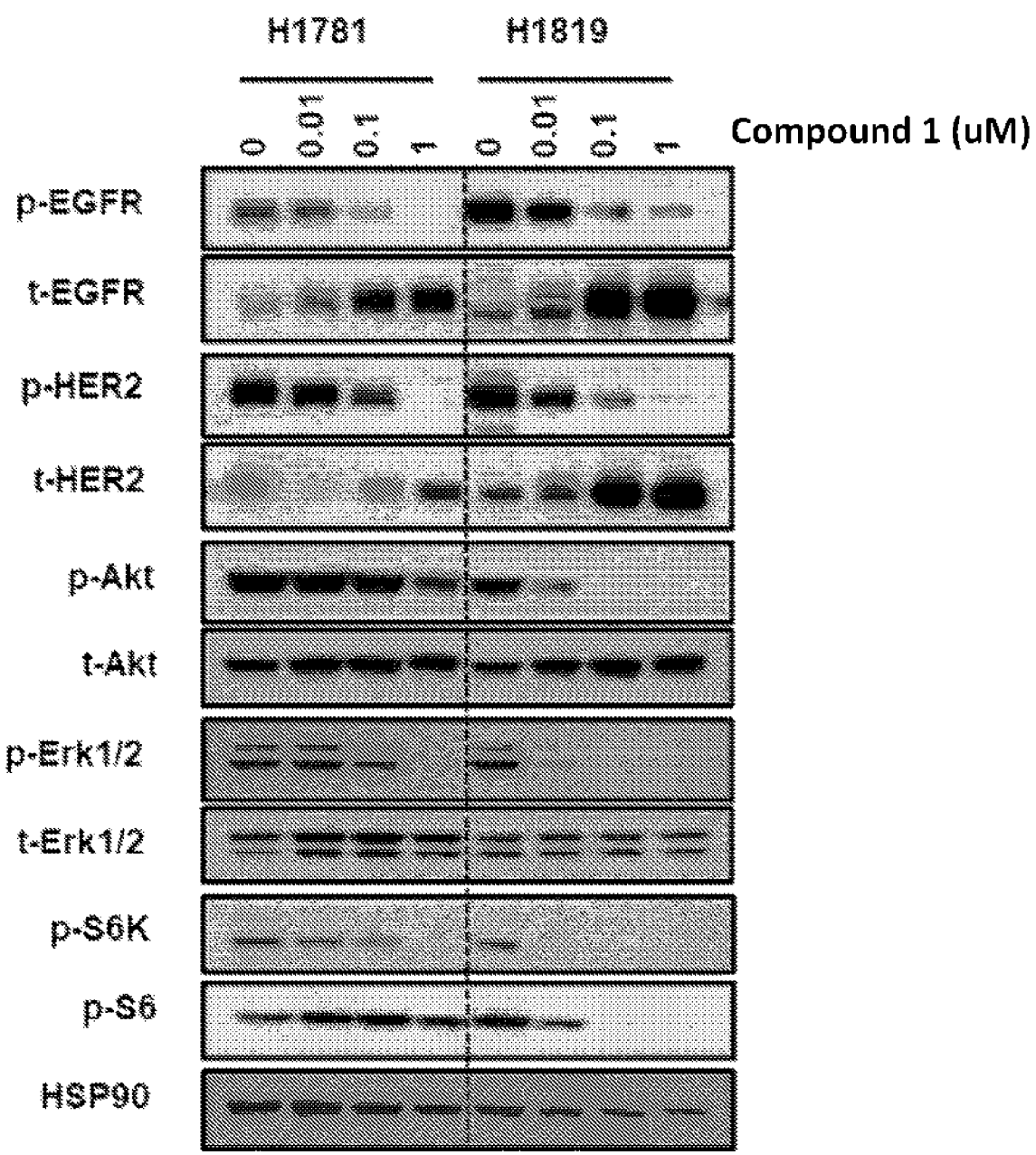
FIG. 2 is a Western blot showing the effects of Compound 1 on HER2 and EGFR phosphorylation and their downstream signaling components at the indicated concentrations in H1781 and H1819 cells.
Figure 3:
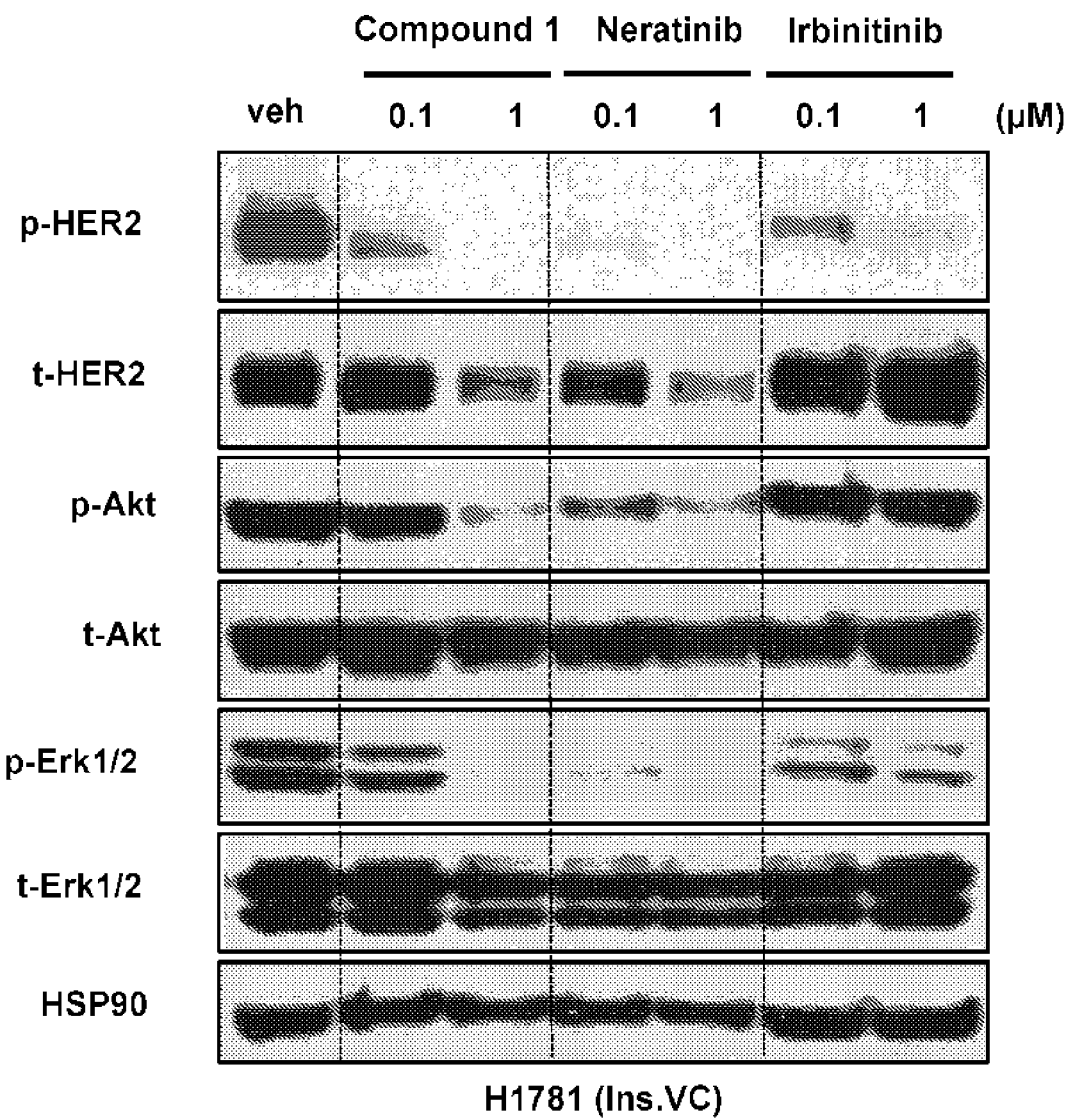
FIG. 3 is a Western blot showing the effects of Compound 1, neratinib, or irbinitinib on HER2 phosphorylation and its downstream signaling components at the indicated concentrations in H1781 cells expressing HER2 InsVC mutant, treated with Compound 1, neratinib, or irbinitinib for 24 hours.
Figure 4:
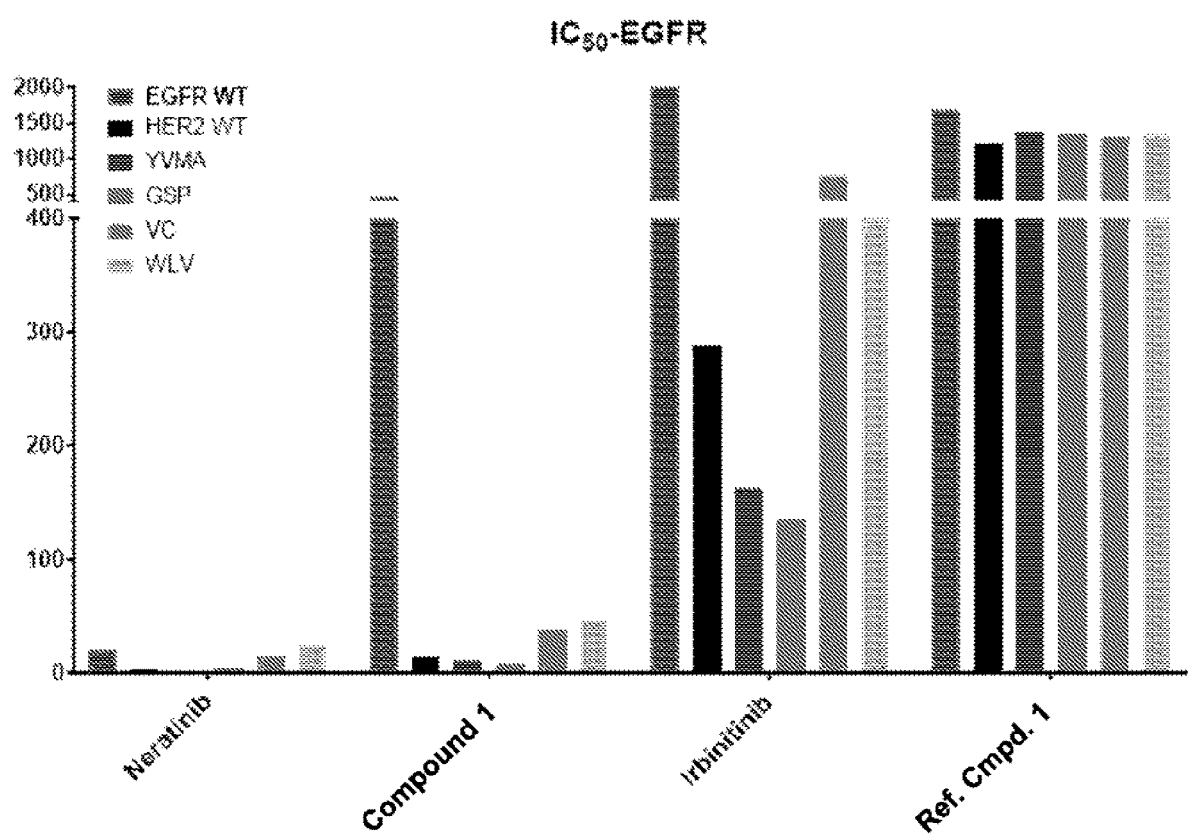
FIG. 4 is a bar graph showing the selective inhibition of HER2 and its mutant over EGFR by Compound 1.
Figure 5:
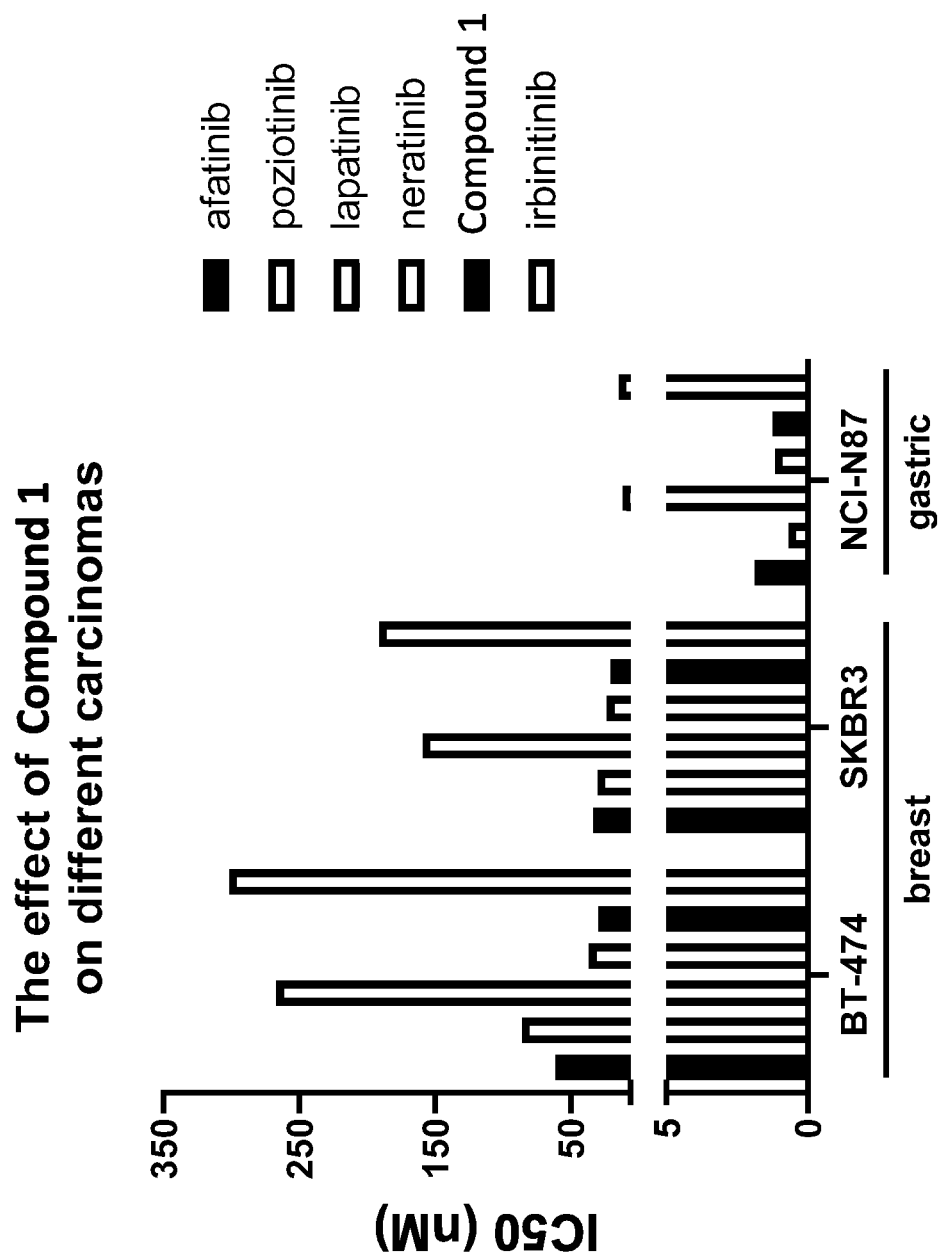
FIG. 5 is a bar graph showing the effect of Compound 1 on different carcinomas in comparison to known HER2 inhibitors.
Figure 6:
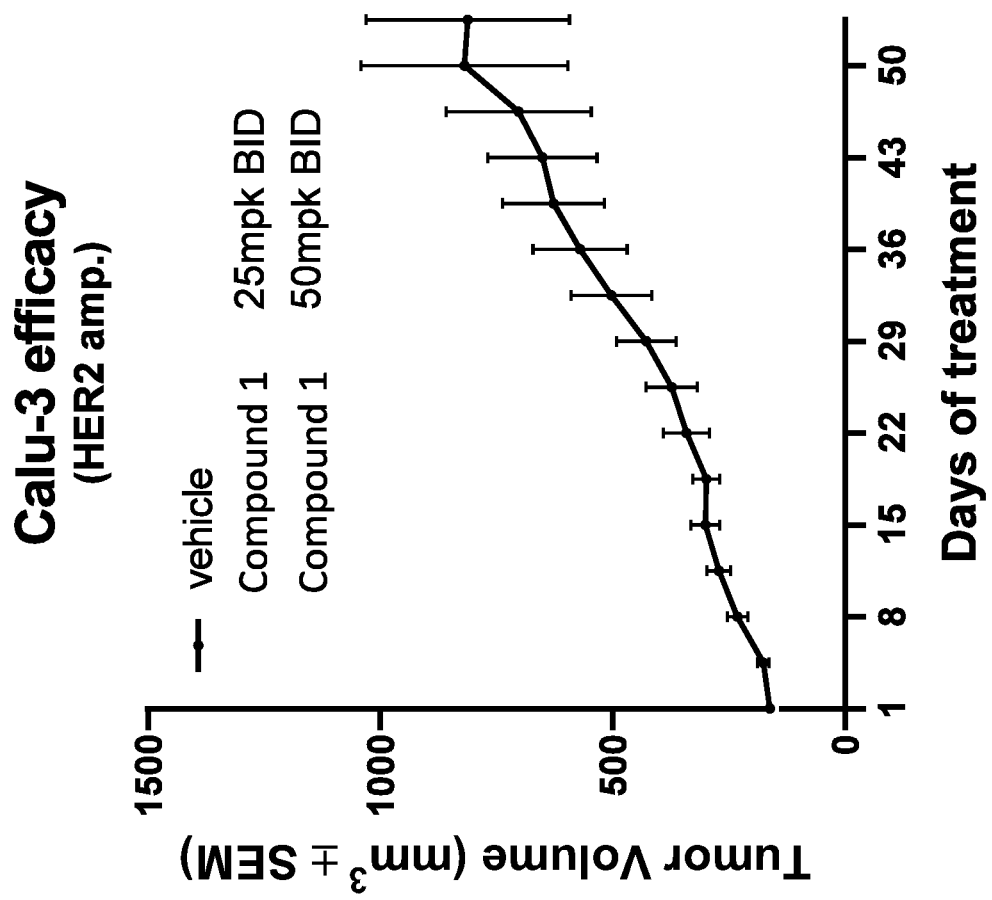
FIG. 6 shows tumor volume over time when the tumors are treated with Compound 1 at different doses.

Activities of representative compounds of the present application are shown in FIGS. 1A, 1B, and 2-4 and Tables 3-4 below.

TABLE 3

Biochemical activities and antiproliferative activities in Ba/F3 cells (EC$_{50}$ values presented: A ≥ 500 nM, 500 nM > B ≥ 250 nM, 250 nM > C ≥ 100 nM, D < 100 nM, NT = not yet tested).

| Compound # | Biochemical Activities | | Antiproliferative Activities (Ba/F3 cells) | | | | | | |
|---|---|---|---|---|---|---|---|---|---|
| | WT EGFR | WT HER2 | WT EGFR | WT HER2 | EGFR EC$_{50}$/ HER2 EC$_{50}$ | HER2 InsYVMA | HER2 InsGSP | HER2 InsVC | HER2 InsWLV |
| Neratinib | D | D | D | D | 6 | D | D | D | D |
| Irbinitinib | B | D | A | B | 18 | C | C | A | B |
| Ref. Cmpd. 1 | A | D | A | A | 1 | A | A | A | A |
| 1 | C | D | B | D | 32 | D | D | D | D |
| 2 | C | D | A | D | 222 | D | D | B | C |
| 3 | NT | NT | B | D | 87 | D | D | D | D |
| 4 | NT | NT | A | D | 49 | D | D | D | C |
| 5 | NT | NT | C | D | 6 | D | D | D | C |
| 6 | NT | NT | A | D | 178 | D | D | D | C |

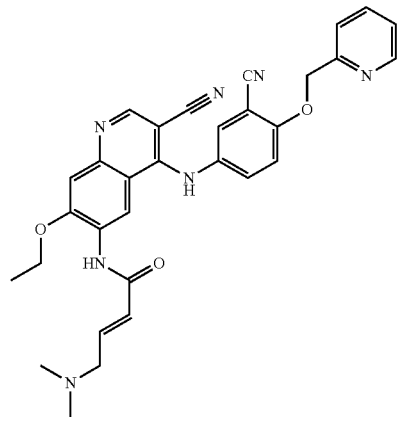

Neratinib

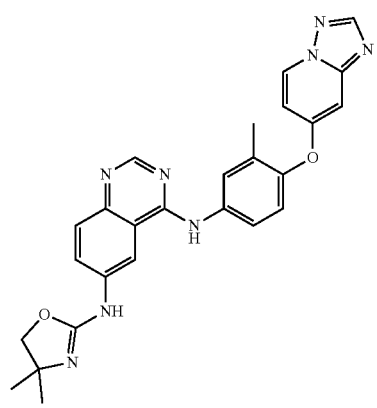

Irbinitinib

TABLE 3-continued

Biochemical activities and antiproliferative activities in Ba/F3 cells (EC$_{50}$ values presented: A ≥ 500 nM, 500 nM > B ≥ 250 nM, 250 nM > C ≥ 100 nM, D < 100 nM, NT = not yet tested).

|  | Biochemical Activities | | | | Antiproliferative Activities (Ba/F3 cells) | | | | |
|---|---|---|---|---|---|---|---|---|---|
| | | | | | EGFR EC$_{50}$/ | | | | |
| Compound # | WT EGFR | WT HER2 | WT EGFR | WT HER2 | HER2 EC$_{50}$ | HER2 InsYVMA | HER2 InsGSP | HER2 InsVC | HER2 InsWLV |

Ref. Cmpd. 1

TABLE 4

Antiproliferative activities in lung cancer cells (EC$_{50}$ values presented: A ≥ 500 nM, 500 nM > B ≥ 250 nM, 250 nM > C ≥ 100 nM, D < 100 nM).

| | Antiproliferative Activities | | | |
|---|---|---|---|---|
| Compound # | H1781 (HER2 InsVC) | H1819 (Her2 amplification) | Calu-3 (Her2 amplification) | DFCI429 (Her2 amplification) |
| 1 | C | D | D | C |
| Afatinib | C | D | C | C |
| Irbinitinib | A | C | A | A |

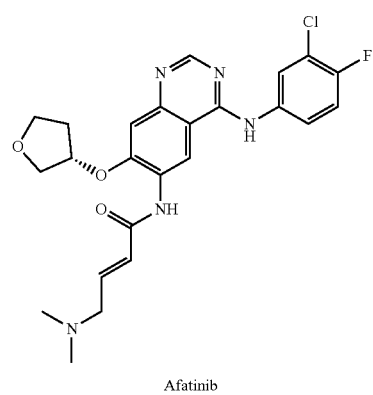 [SMILES: CN(C)C/C=C/C(=O)Nc1cc2c(Nc3ccc(F)c(Cl)c3)ncnc2cc1O[C@H]1CCOC1]

Afatinib

TABLE 4-continued

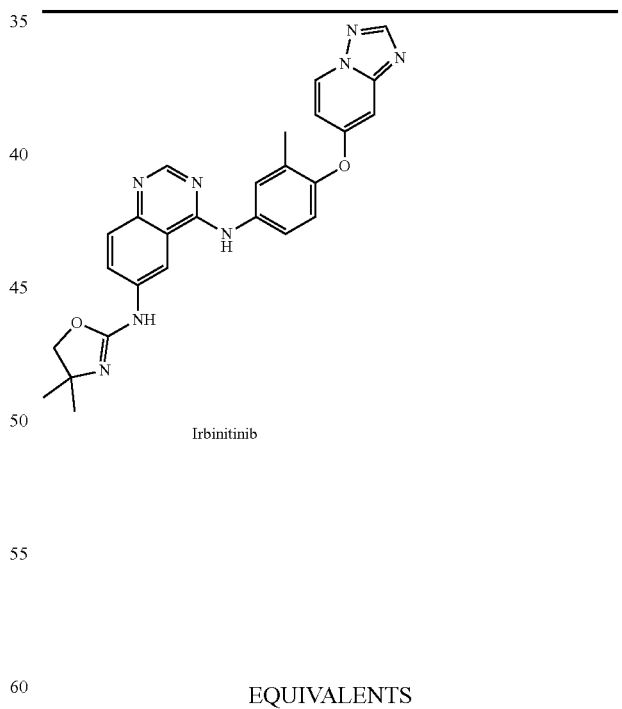

Irbinitinib

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:
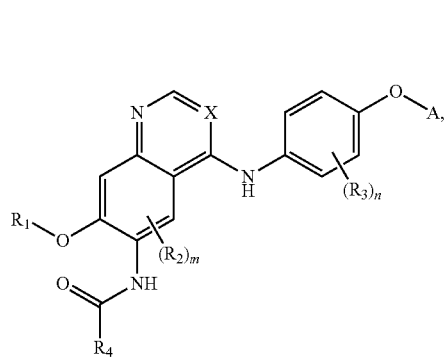
or a pharmaceutically acceptable salt or solvate thereof, wherein:
A is
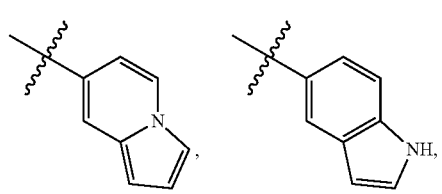
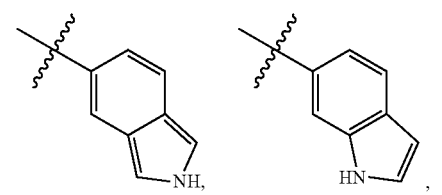
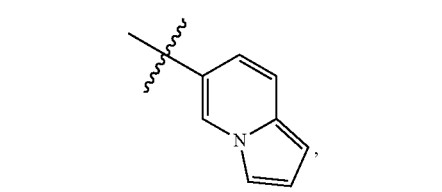
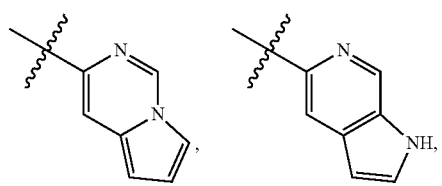
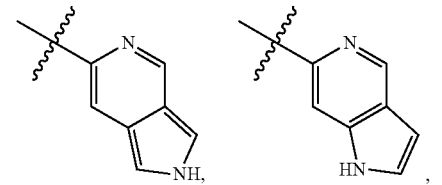
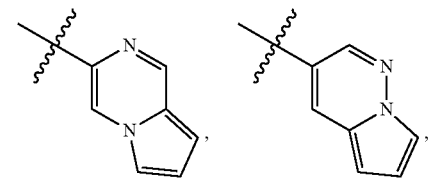
-continued
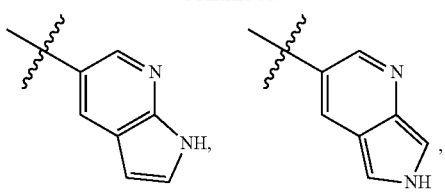
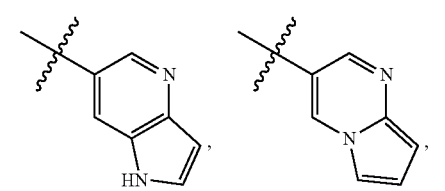
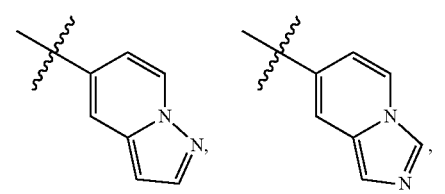
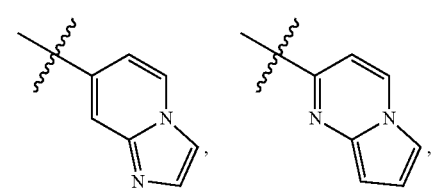
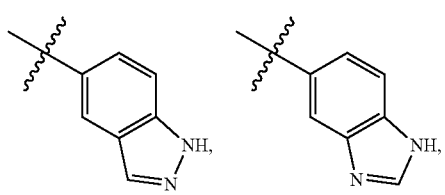
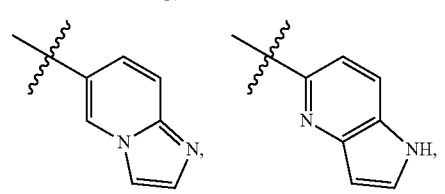
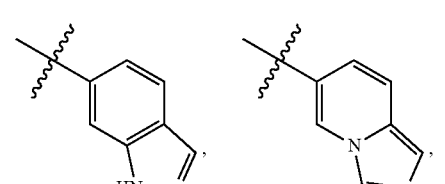
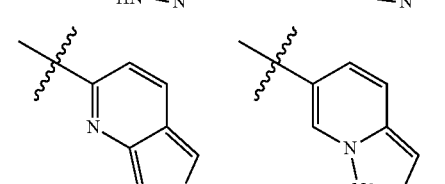
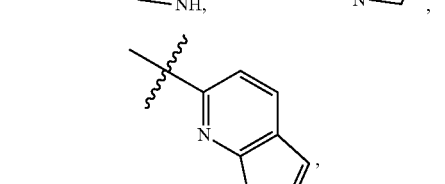

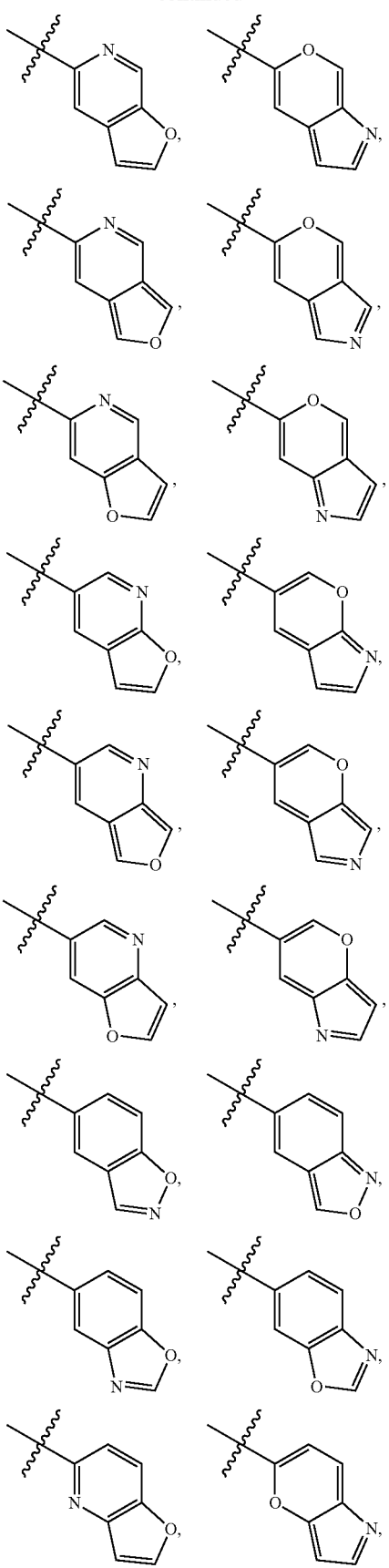
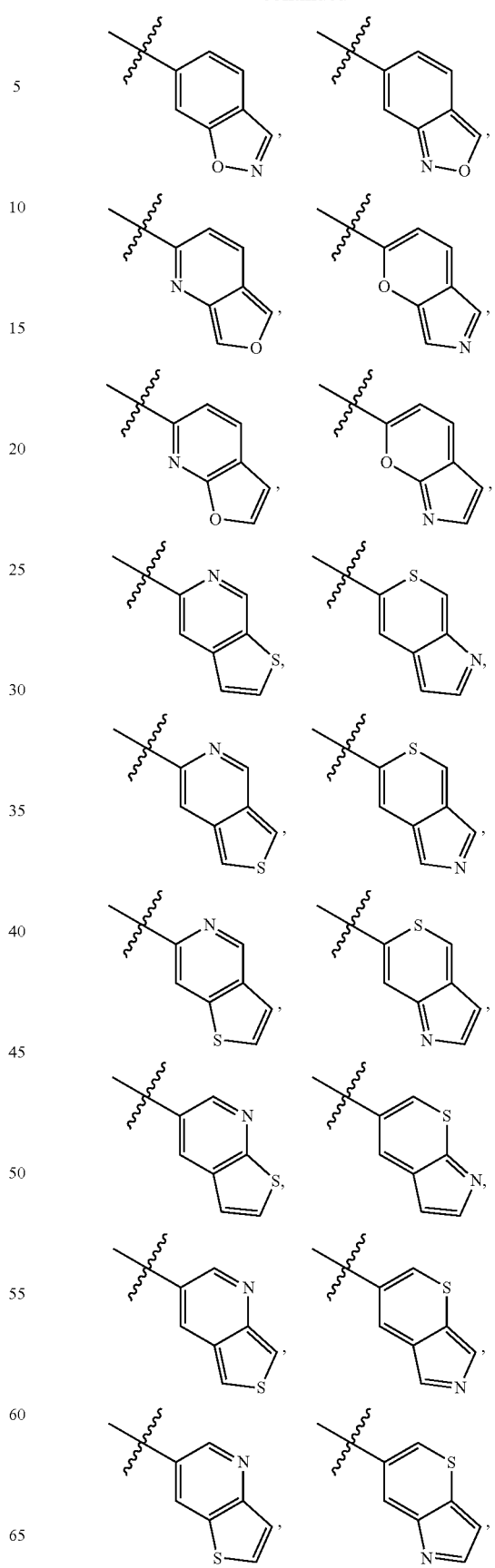

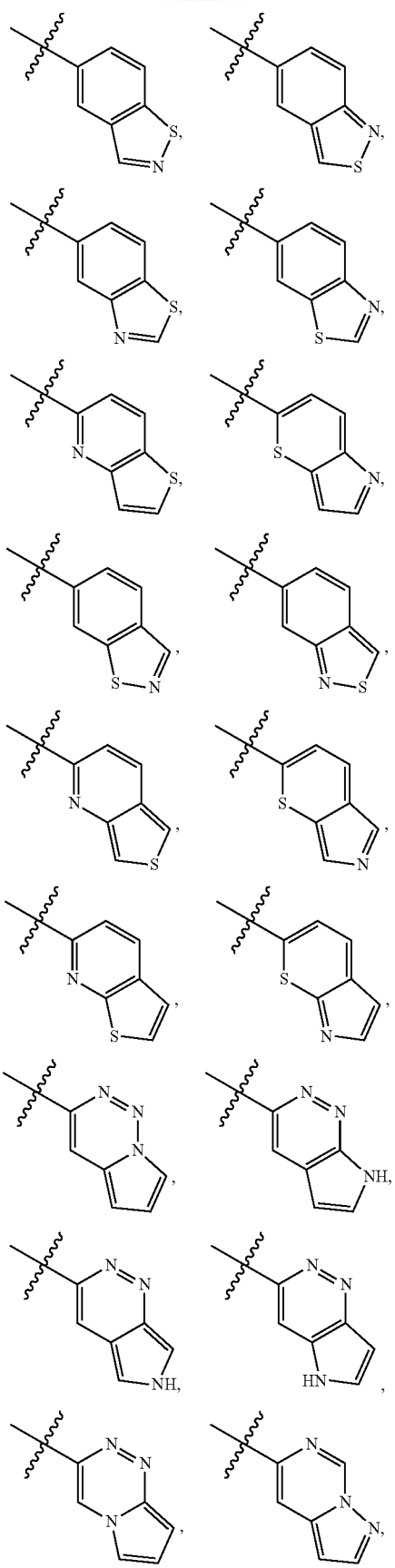
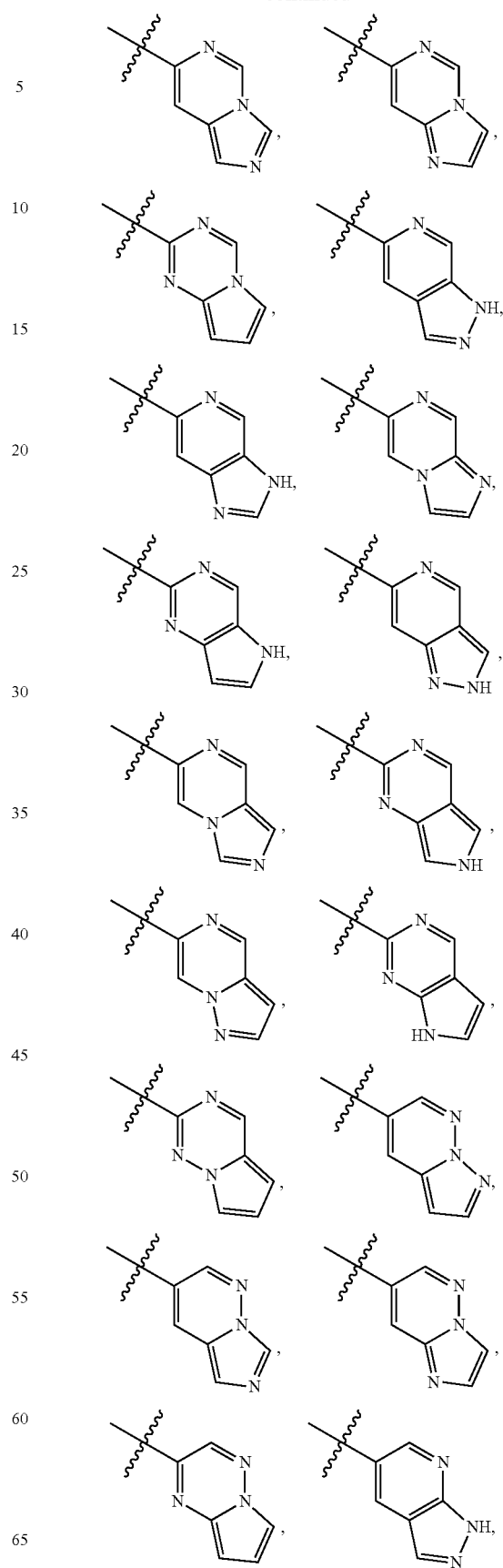

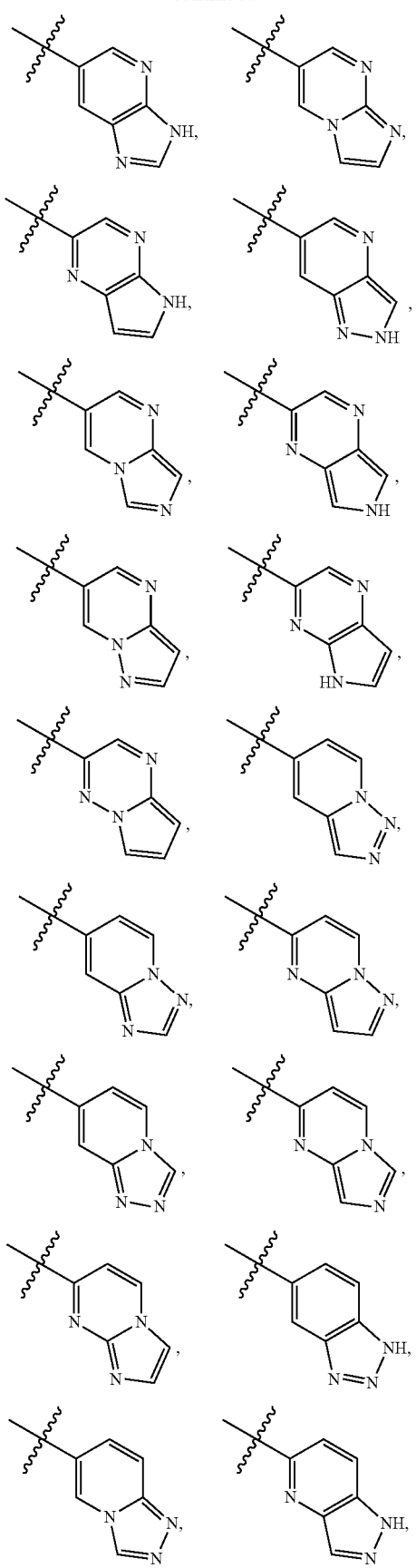
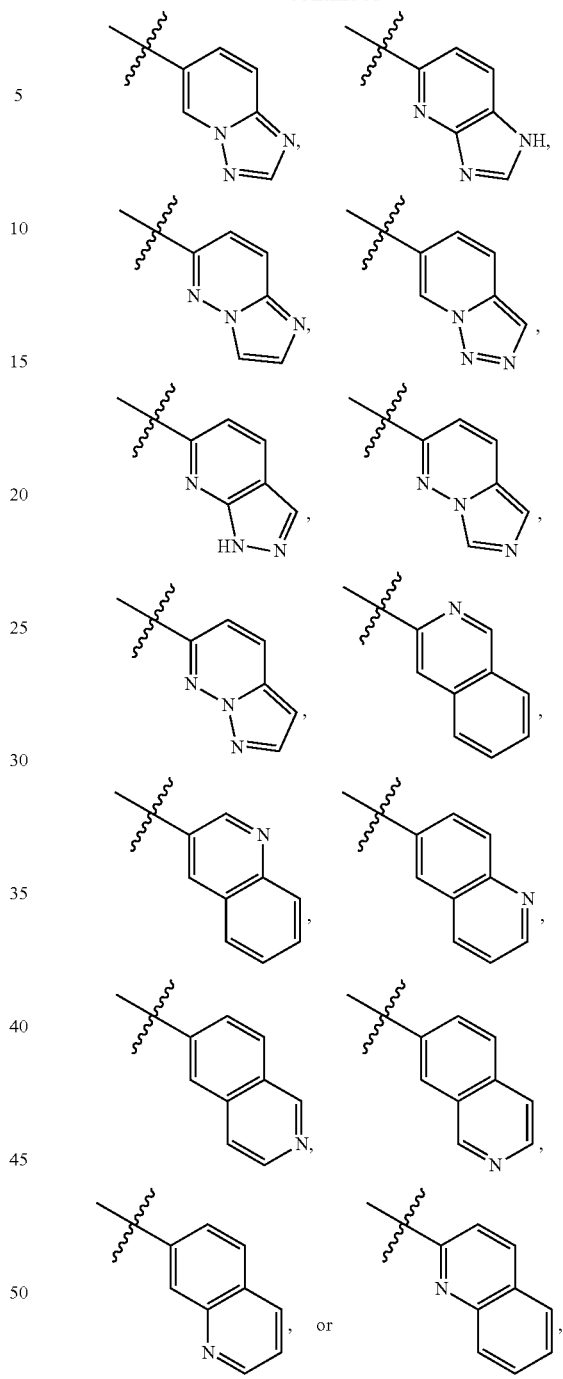

and is optionally substituted with one or more $R_A$;

each $R_A$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino;

X is C—CN;

$R_1$ is $C_1$-$C_6$ alkyl or $(CH_2)_{1-3}$-heterocyclyl comprising one 5- or 6-membered ring and 1-3 heteroatoms selected N and O and at least one N, wherein the alkyl is optionally substituted with one or more $R_B$' and the heterocyclyl is optionally substituted with one or more $R_B$;

m is 0, 1, or 2;

each $R_2$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, di-$C_1$-$C_6$ alkylamino, or $NHC(O)R_5$;

n is 0, 1, 2, 3, or 4;

each $R_3$ is independently $C_1$-$C_6$ alkyl, $C_1$-$C_6$ haloalkyl, $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino;

$R_4$ and $R_5$ are each independently $C_2$-$C_4$ alkenyl optionally substituted with one or more $R_x$;

each $R_x$ is independently $NH_2$, $C_1$-$C_3$ alkylamino, or di-$C_1$-$C_3$ alkylamino;

each $R_B'$ is independently $C_1$-$C_6$ alkoxy, $C_1$-$C_6$ haloalkoxy, halogen, OH, CN, $NO_2$, $NH_2$, $C_1$-$C_6$ alkylamino, or di-$C_1$-$C_6$ alkylamino; and each $R_B$ is independently $C_1$-$C_6$ alkyl, $C_1$-$C_6$ haloalkyl, or $R_B'$, wherein when A is 4-quinolinyl and n is 1, then $R_3$ is not halogen.

2. The compound of claim 1, wherein each $R_A$ is independently $C_1$-$C_6$ alkyl.

3. The compound of claim 1, wherein $R_1$ is $C_1$-$C_6$ alkyl optionally substituted with one or more $R_B'$.

4. The compound of claim 1, wherein $R_1$ is $(CH_2)_{1-3}$-heterocyclyl comprising one 5- or 6-membered ring and 1-3 heteroatoms selected N and O and at least one N, wherein the heterocyclyl is optionally substituted with one or more $R_B$.

5. The compound of claim 1, wherein m is 0.

6. The compound of claim 1, wherein n is 0, 1, or 2.

7. The compound of claim 1, wherein each $R_3$ is independently $C_1$-$C_6$ alkyl or halogen.

8. The compound of claim 1, wherein $R_4$ is $C_2$-$C_4$ alkenyl substituted with one or more R.

9. The compound of claim 1, wherein $R_4$ is

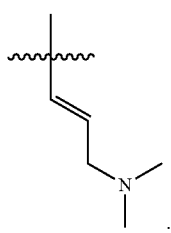 [SMILES: */C=C/CN(C)C]

10. The compound of claim 1, wherein each R, is independently $C_1$-$C_3$ alkylamino or di-$C_1$-$C_3$ alkylamino.

11. The compound of claim 1, wherein each $R_B'$ is independently $NH_2$, $C_1$-$C_6$ alkylamino, or di-$C_1$-$C_6$ alkylamino.

12. The compound of claim 1, wherein each $R_B$ is independently $C_1$-$C_6$ alkyl.

13. The compound of claim 1, being of any one of Formulae (Iba1)-(Iba3):

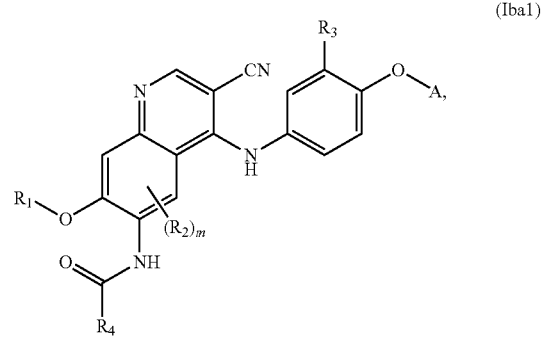
(Iba1)

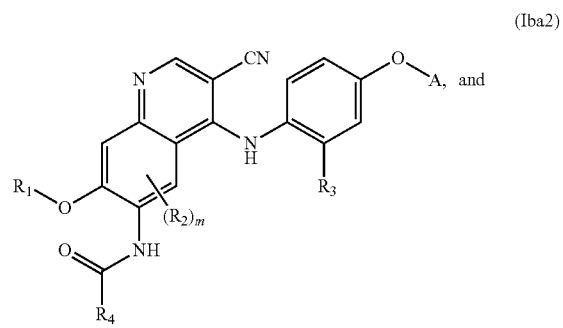
(Iba2), and

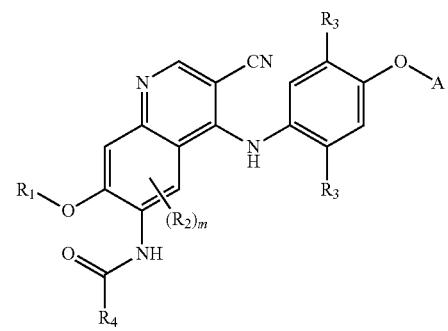
(Iba3)

or a pharmaceutically acceptable salt or solvate thereof.

14. The compound of claim 1, being of any one of Formulae (Ibc1)-(Ibc2):

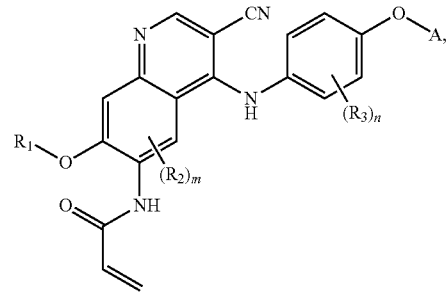
(Ibc1)

-continued
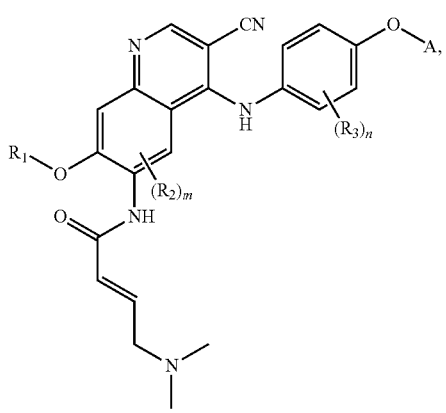
(Ibc2)
or a pharmaceutically acceptable salt or solvate thereof.
15. The compound of claim 1, being of any one of Formulae (Ibd1)-(Ibd4):
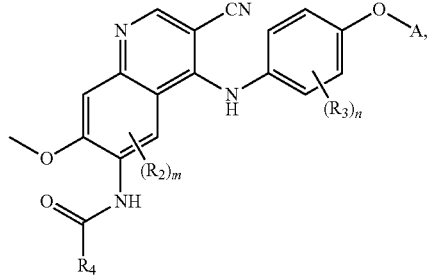
(Ibd1)
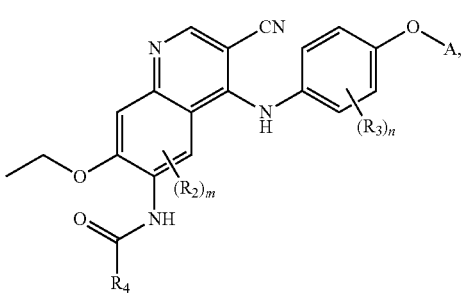
(Ibd2)
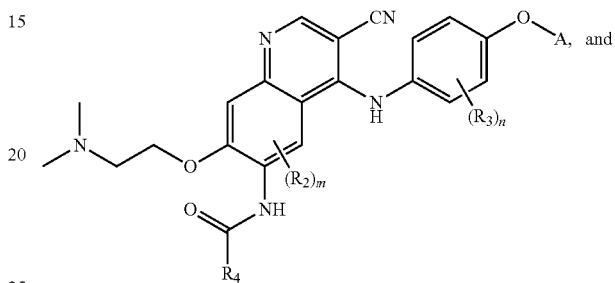
(Ibd3), and
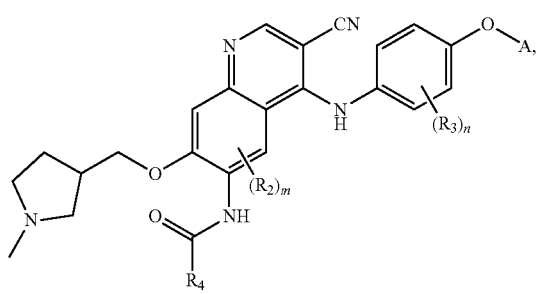
(Ibd4)
or a pharmaceutically acceptable salt or solvate thereof.
16. A compound selected from the group consisting of:
| Compound # | Structure |
|---|---|
| 1 | 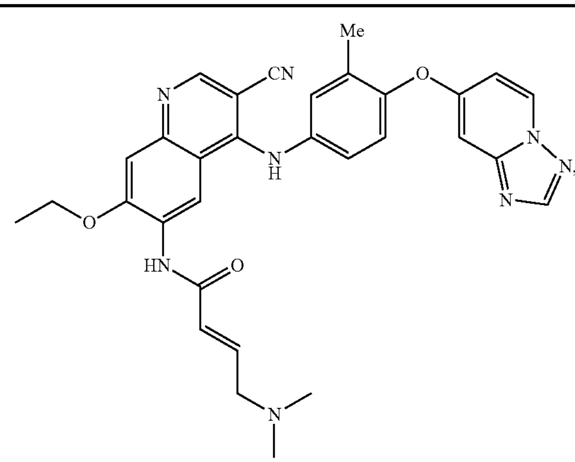 |

-continued
| Compound # | Structure |
|---|---|
| 2 | 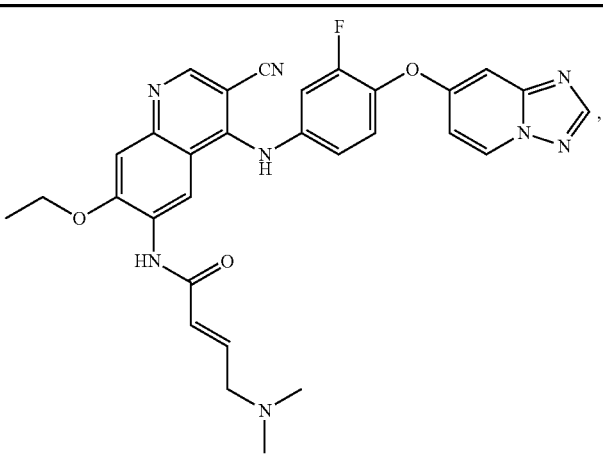 |
| 3 | 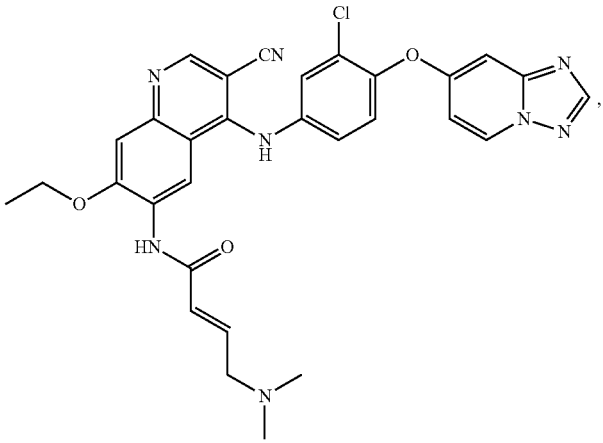 [SMILES: CCOc1cc2ncc(C#N)c(Nc3ccc(Oc4ccn5ncnc5c4)c(F)c3)c2cc1NC(=O)/C=C/CN(C)C] |
| 4 | 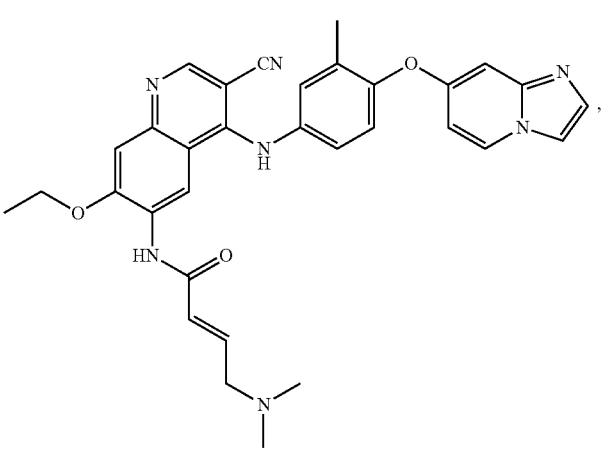 [SMILES: CCOc1cc2ncc(C#N)c(Nc3ccc(Oc4ccn5ccnc5c4)c(C)c3)c2cc1NC(=O)/C=C/CN(C)C] |

-continued
| Compound # | Structure |
|---|---|
| 5 | 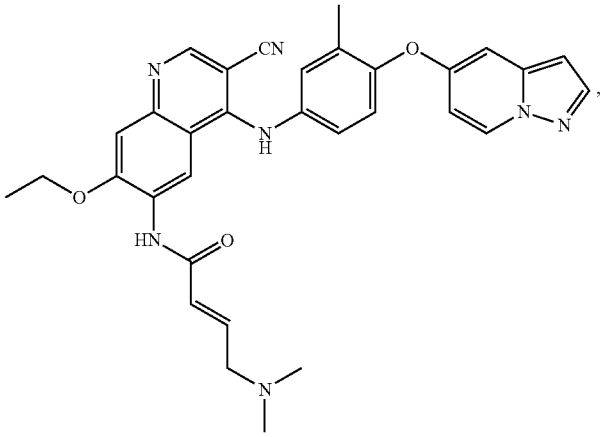 [SMILES: CCOc1cc2ncc(C#N)c(Nc3ccc(Oc4ccn5nccc5c4)c(C)c3)c2cc1NC(=O)/C=C/CN(C)C] |
| 6 | 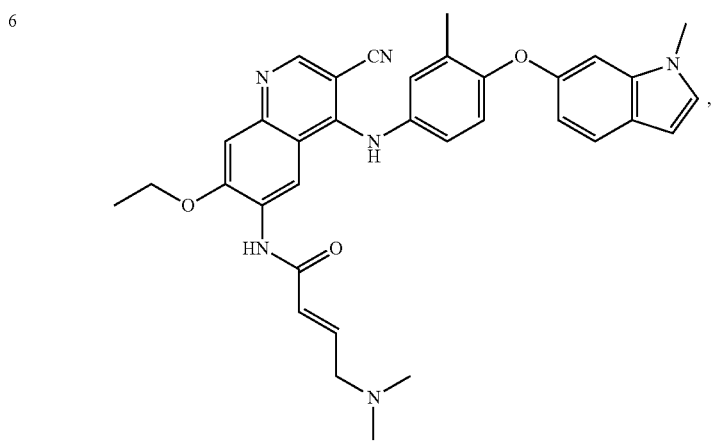 |
| 7 | 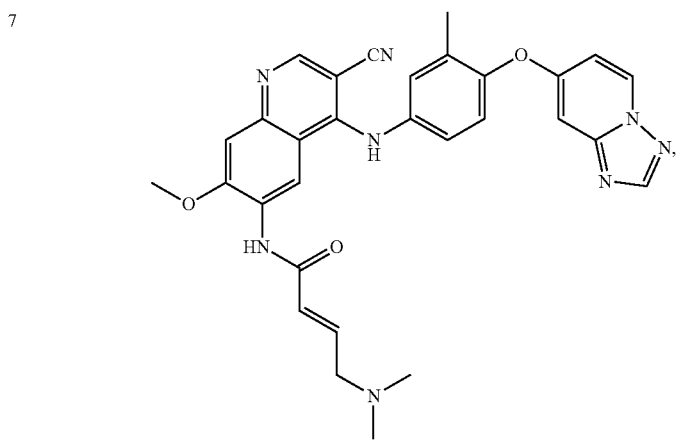 |

-continued

| Compound # | Structure |
|---|---|
| 8 | (structure) |
| 9 | (structure) |
| 10 | (structure) |

| Compound # | Structure |
|---|---|
| 11 | 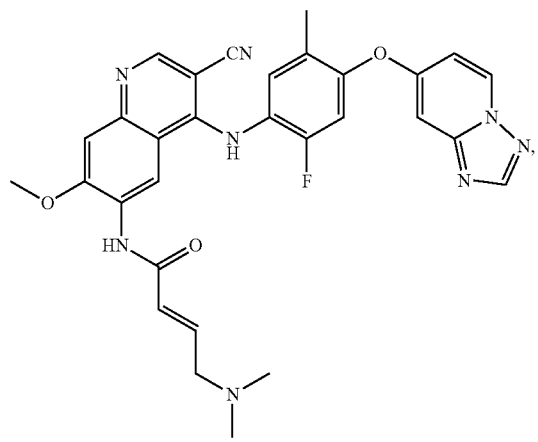 |
| 12 | 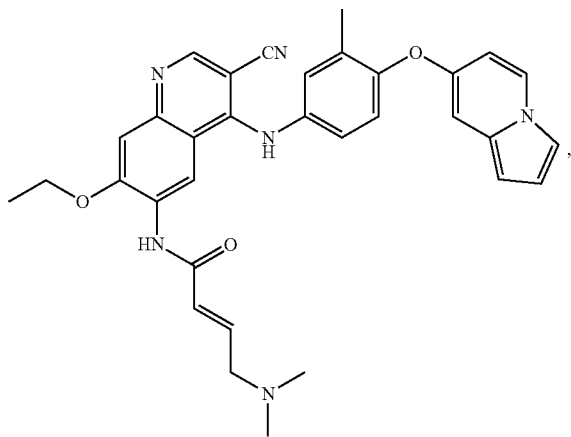 |
| 13 | 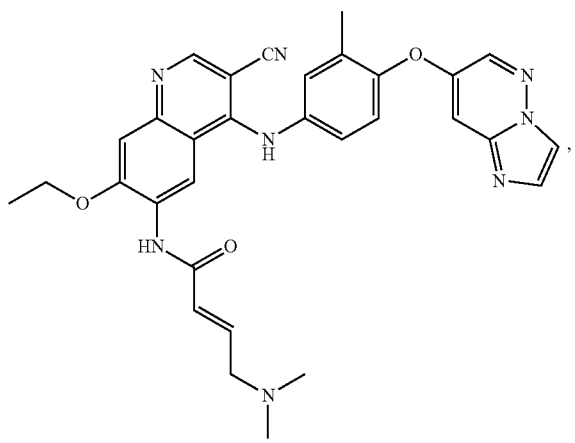 |

-continued
| Compound # | Structure |
|---|---|
| 14 | 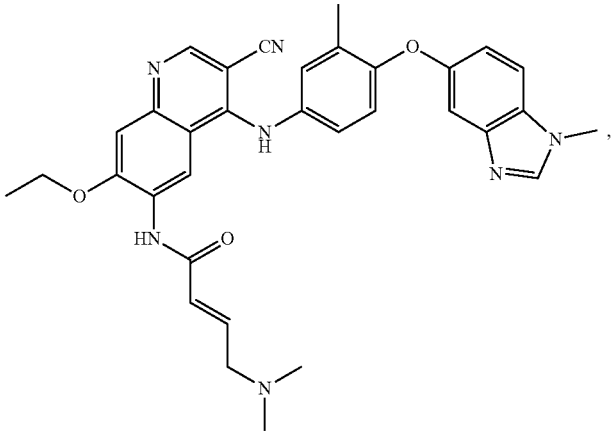 [SMILES: CCOc1cc2ncc(C#N)c(Nc3ccc(Oc4ccc5c(c4)ncn5C)c(C)c3)c2cc1NC(=O)/C=C/CN(C)C] |
| 15 | 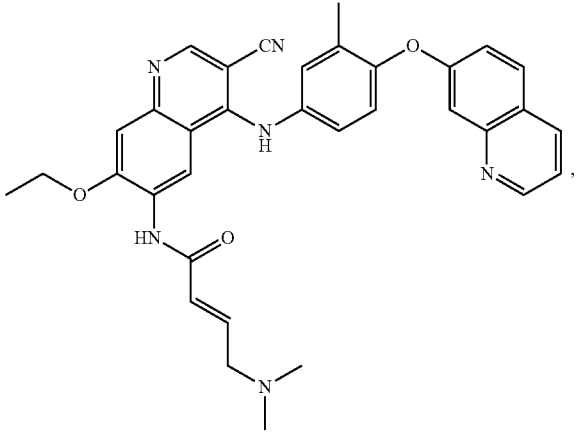 [SMILES: CCOc1cc2ncc(C#N)c(Nc3ccc(Oc4ccc5cccnc5c4)c(C)c3)c2cc1NC(=O)/C=C/CN(C)C] |
| 16 | 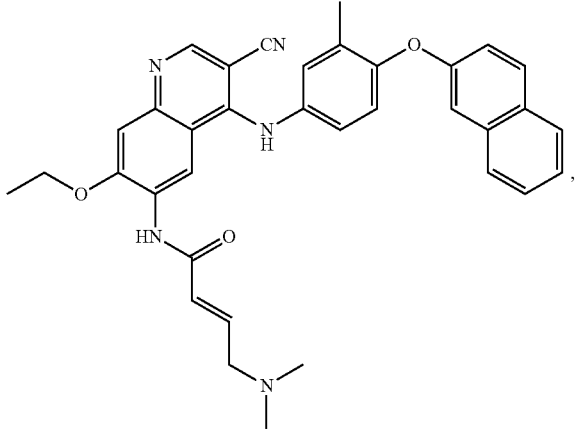 [SMILES: CCOc1cc2ncc(C#N)c(Nc3ccc(Oc4ccc5ccccc5c4)c(C)c3)c2cc1NC(=O)/C=C/CN(C)C] |

-continued
| Compound # | Structure |
|---|---|
| 17 | 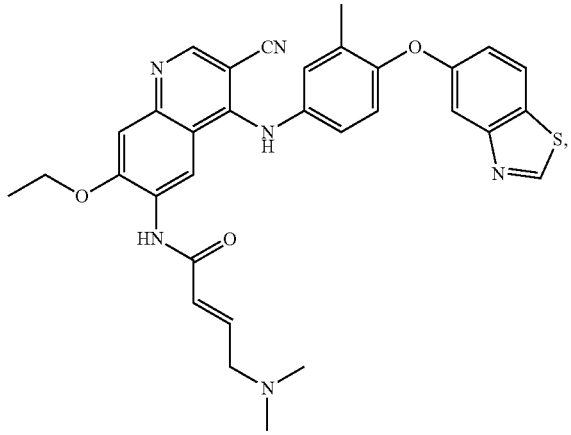 [SMILES: CCOc1cc2ncc(C#N)c(Nc3ccc(Oc4ccc5scnc5c4)c(C)c3)c2cc1NC(=O)/C=C/CN(C)C] |
| 18 | 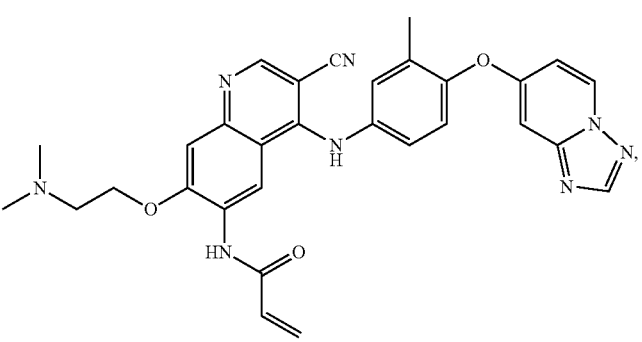 [SMILES: C=CC(=O)Nc1cc2c(Nc3ccc(Oc4ccn5ncnc5c4)c(C)c3)c(C#N)cnc2cc1OCCN(C)C] |
| 19 | 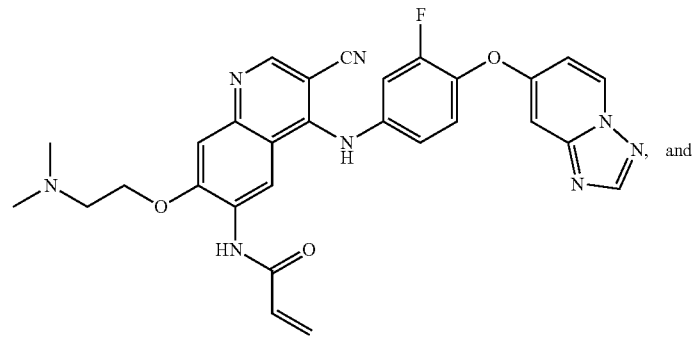 [SMILES: C=CC(=O)Nc1cc2c(Nc3ccc(Oc4ccn5ncnc5c4)c(F)c3)c(C#N)cnc2cc1OCCN(C)C], and |
| 20 | 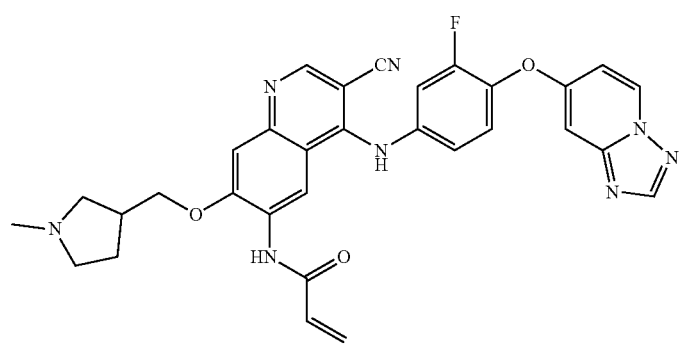 [SMILES: C=CC(=O)Nc1cc2c(Nc3ccc(Oc4ccn5ncnc5c4)c(F)c3)c(C#N)cnc2cc1OCC1CCN(C)C1] |
or a pharmaceutically acceptable salt or solvate thereof.
17. A pharmaceutical composition comprising the compound of claim 1 and a pharmaceutically acceptable carrier.
18. A pharmaceutical kit comprising the compound of claim 1.
19. The compound of claim 1, wherein the compound of Formula I is:

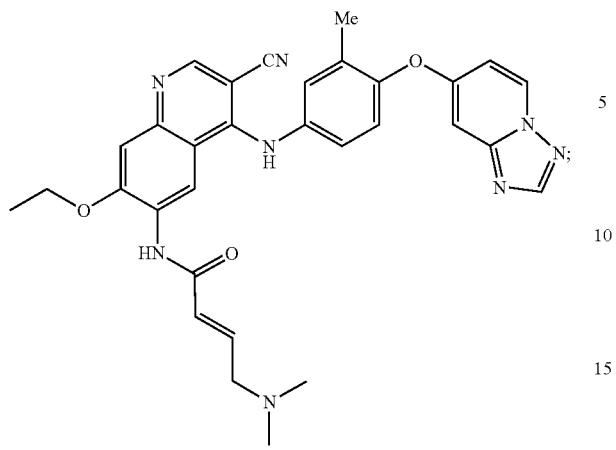
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 11,814,379 B2 | Page 1 of 1 |
| APPLICATION NO. | : 16/973276 | |
| DATED | : November 14, 2023 | |
| INVENTOR(S) | : Nathanael S. Gray et al. | |

It is certified that error appears in the above-identified patent and that said Letters Patent is hereby corrected as shown below:

In the Claims

Claim 8, Column 109, Line 41 should read:
-- substituted with one or more Rx. --

Claim 10, Column 109, Line 60 should read:
-- The compound of claim 1, wherein each Rx is inde- --

Signed and Sealed this
Sixteenth Day of April, 2024

Katherine Kelly Vidal
*Director of the United States Patent and Trademark Office*